United States Patent
Galbo et al.

(10) Patent No.: US 6,420,463 B1
(45) Date of Patent: Jul. 16, 2002

(54) HYDROXY-SUBSTITUTED N-ALKOXY HINDERED AMINES AND COMPOSITIONS STABILIZED THEREWITH

(75) Inventors: James P. Galbo, Wingdale, NY (US); Gerald A. Capocci, Greenwich, CT (US); Nancy N. Cliff, Ringwood, NJ (US); Robert E. Detlefsen, Putnam Valley, NY (US); Michael P. DiFazio, Mobile, AL (US); Ramanathan Ravichandran, Nanuet; Peter Solera, Suffern, both of NY (US)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 09/789,694

(22) Filed: Feb. 21, 2001

Related U.S. Application Data

(62) Division of application No. 09/257,711, filed on Feb. 25, 1999, now Pat. No. 6,271,377.

(51) Int. Cl.[7] .................................................. C08K 5/34
(52) U.S. Cl. .................... 524/102; 523/122; 524/90; 524/91; 524/96; 524/100; 524/101; 524/126; 524/128; 524/132; 524/144; 524/153; 524/291; 524/359; 524/371; 524/399; 524/404; 524/425; 524/432; 524/445; 524/449; 524/492; 524/494
(58) Field of Search .......................... 523/122; 524/90, 524/91, 96, 100, 101, 102, 126, 128, 132, 144, 153, 291, 359, 371, 399, 404, 425, 432, 445, 449, 492, 494

(56) References Cited

U.S. PATENT DOCUMENTS

| | | | |
|---|---|---|---|
| 4,972,009 A | 11/1990 | Suhadolnik et al. | 524/99 |
| 5,004,770 A | 4/1991 | Cortolano et al. | 524/99 |
| 5,096,950 A | 3/1992 | Galbo et al. | 524/99 |
| 5,204,473 A | 4/1993 | Winter et al. | 546/188 |
| 5,627,248 A | 5/1997 | Koster et al. | 526/217 |
| 5,844,025 A | 12/1998 | Cunkle et al. | 524/99 |
| 6,114,420 A | 9/2000 | Zedda et al. | 524/100 |

FOREIGN PATENT DOCUMENTS

| | | |
|---|---|---|
| EP | 0135280 | 3/1985 |
| EP | 0427672 | 5/1991 |
| WO | 00/78709 | 5/2000 |

OTHER PUBLICATIONS

D. Gravert et al., J. Am. Chem. Soc. (1998), vol. 120, pp. 9481–9495.
C. Hawker et al., JACS, vol. 118, No. 46, (1996), pp. 11467–11471.
Nigam et al, J. Chem. Soc., Trans. Faraday Soc., 1, 1976, 72, pp. 2324–2340.
Asmas et al., Int. J. Radiat. Biol., 1976, 29, pp. 211–219.

*Primary Examiner*—Kriellion A. Sanders
(74) *Attorney, Agent, or Firm*—Tyler A. Stevenson; Luther A. R. Hall

(57) ABSTRACT

Hindered amines substituted on the N-atom with an -O-E-OH moiety are particularly effective in stabilizing polyolefin and automotive coating compositions against the deleterious effects of oxidative, thermal and actinic radiation where the presence of the OH group on the compounds adds important properties not attainable by the use of normal -O-E moieties.

35 Claims, No Drawings

HYDROXY-SUBSTITUTED N-ALKOXY HINDERED AMINES AND COMPOSITIONS STABILIZED THEREWITH

This is a divisional of application Ser. No. 09/257,711, filed on Feb. 25, 1999 now U.S. Pat. No. 6,271,377.

The instant invention pertains to hindered amine compounds which are substituted on the N-atom by N-alkoxy moieties containing one to three hydroxyl groups. These materials are particularly effective in stabilizing polyolefins, especially thermoplastic polyolefins, against the deleterious effects of oxidative, thermal and actinic radiation. The compounds are also effective in stabilizing acid catalyzed and ambient cured coatings systems.

BACKGROUND OF THE INVENTION

4-Hydroxy-1-oxyl-2,2,6,6-tetramethylpiperidine and 4-oxo-1-oxyl-2,2,6,6-tetramethylpiperidine are reported to have been used to trap carbon centered radicals formed from methanol, ethanol, isopropanol and sec-butanol by S. Nigam et al., J. Chem. Soc., Trans. Faraday Soc. 1, 1976, 72, 2324 and by K.-D. Asmus et al., Int. J. Radiat. Biol., 1976, 29, 211.

U.S. Pat. No. 5,627,248 and European Patent Application No. 135,280 A2 describe, respectively, difunctional and monofunctional living free radical polymerization initiators, some of which contain hindered amine ethers substituted by hydroxy groups. These compounds differ substantially in structure and performance from the instant compounds.

European Patent Application No. 427,672 A1 and U.S. Pat. No. 4,972,009 mention, but do not exemplify, respectively, hydroxylamine and nitrone structures, some of which contain $C_1-C_4$ hydroxyalkoxy substituted 2,2,6,6-tetramethylpiperidine derivatives. Such structures are outside the scope of the instant invention.

U.S. Pat. No. 5,204,473 describes N-hydrocarbyloxy hindered amine derivatives that are prepared exclusively from organic compounds containing only carbon and hydrogen atoms. Such compounds are structurally quite different from the instant compounds.

U.S. Pat. No. 5,004,770 describes hindered amine compounds which are substituted on the N-atom by alkoxy moieties which alkoxy groups are themselves unsubstituted. These compounds are especially useful in polymers including polybutadiene, polystyrene, ABS, polyacetal, polyamide, polyester, polyurethane and polycarbonate.

U.S. Pat. No. 5,096,950 also describes hindered amine compounds which are substituted on the N-atom by alkoxy moieties which alkoxy groups are themselves unsubstituted. These compounds are found to be useful in polyolefins.

The instant compounds are N-alkoxy substituted derivatives of 2,2,6,6-tetraalkylpiperidines where the alkoxy group is substituted by one to three hydroxy moieties. The instant compounds also comprise N-alkoxy bridged derivatives of the 2,2,6,6-tetraalkylpiperidines where the alkoxy moiety, which is substituted by one to three hydroxy groups, is shared by two hindered amine molecules. The free hydroxy moieties of these compounds may be reacted with carboxylic acids, acid chlorides or esters to form simple esters or polyesters, or with isocyanates to form urethanes or polyurethanes.

The instant compounds, because of their low bascity which is shared by the simple unsubstituted N-alkoxy compounds cited in the two patents mentioned above, are of particular value in the stabilization of polyolefins and automotive coating compositions where the activity of the more basic hindered amine stabilizes is significantly reduced because of interaction with the polymer substrate or acid catalytic system needed for curing such substrate.

Examples of polyolefin compositions in which the instant compounds are effective include flame retardant polyolefins where acidic residues from the decomposition of the halogenated flame retardants deactivate hindered amines not having the N—OR group, greenhouse films and agricultural mulch films where acidic residues from pesticides interfere with the activity of "normal" hindered amine stabilizers, and in thermoplastic polyolefins where pigment interactions with basic hindered amine stabilizers interfere with painting the substrate surfaces. Examples of coating compositions in which the instant compounds are effective include melamine crosslinked thermoset acrylic resins, which are cured using strong acids that interact with basic hindered amine stabilizers. The instant compounds are also effective in acrylic alkyd or polyester resins with isocyanate crosslinking agents, and in epoxy resins with carboxylic acid, anhydride, or amine crosslinking agents.

While the unsubstituted N—OR compounds described in U.S. Pat. Nos. 5,004,770 and 5,096,950 also perform well in the compositions described in the paragraph above, the instant compounds differ significantly in both structure and in performance from the prior art compounds by virtue of the presence of the one to three free hydroxy groups present on the N-alkoxy moiety. These hydroxyl groups in the instant compounds provide said compounds with superior antistatic properties, compatibility in more polar environments such as polyurethane based and in water-bome automotive coating systems, and in stabilizing painted automotive thermoplastic olefin structures.

The instant compounds are particularly suited for (a) providing superior compatibility in polycarbonates and polycarbonate/ABS blends compared to the N-OE prior art compounds; and (b) providing superior compatibility in polyesters and polyamides compared to the prior art N-OE compounds.

OBJECTS OF THE INVENTION

There are two objects to the instant invention which are:

1. Novel compounds having on the 1-position of the hindered amine a moiety -O-E-OH where the OH group provides important properties; and 2. Compositions stabilized by the novel compounds described above.

DETAILED DISCLOSURE

The instant invention pertains to novel compounds having 1-alkoxy substituted hindered amine derivatives where the alkoxy moiety is substituted by one to three hydroxy groups as described in formulas (1) to (15); or to novel compounds having 1-alkoxy bridged hindered amine derivatives where the alkoxy moiety, substituted by one to three hydroxy groups, is shared by two hindered amine molecules as described in formulas (16) to (28); or to oligomeric or polymeric hindered amine molecules made from the reaction of dialkyl esters or isocyanates with hydroxy substituted N-alkoxy derivatives of 4-hydroxy-2,2,6,6-tetraalkylpiperidine as described in formula (29); or to simple diester or urethane derivatives of hydroxy substituted N-alkoxy derivatives of 4-hydroxy-2,2,6,6-tetramethylpiperidine as described in formula (30)

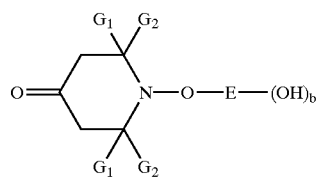 (1)
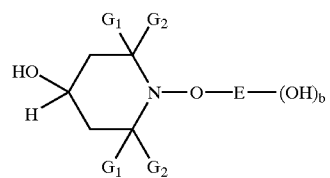 (2)
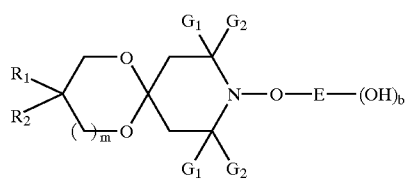 (3)
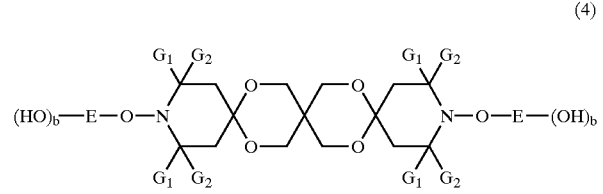 (4)
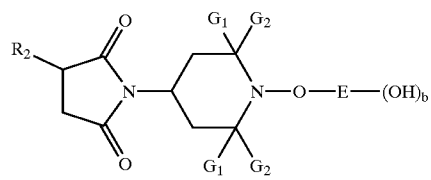 (5)
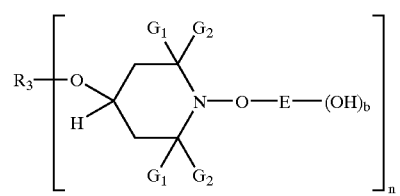 (6)
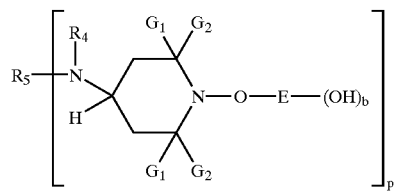 (7)
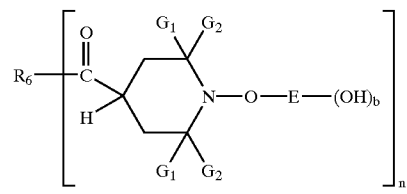 (8)
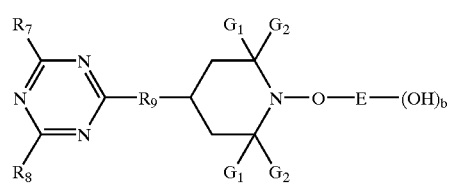 (9)
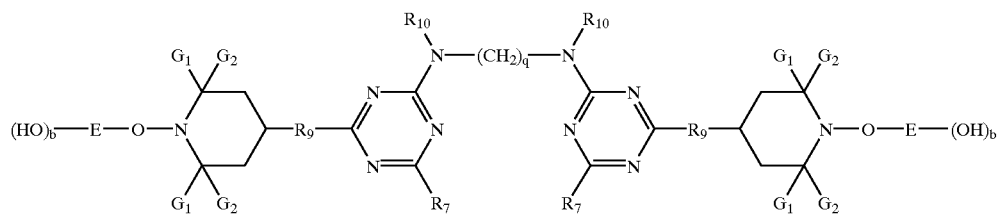 (10)

-continued
(11)
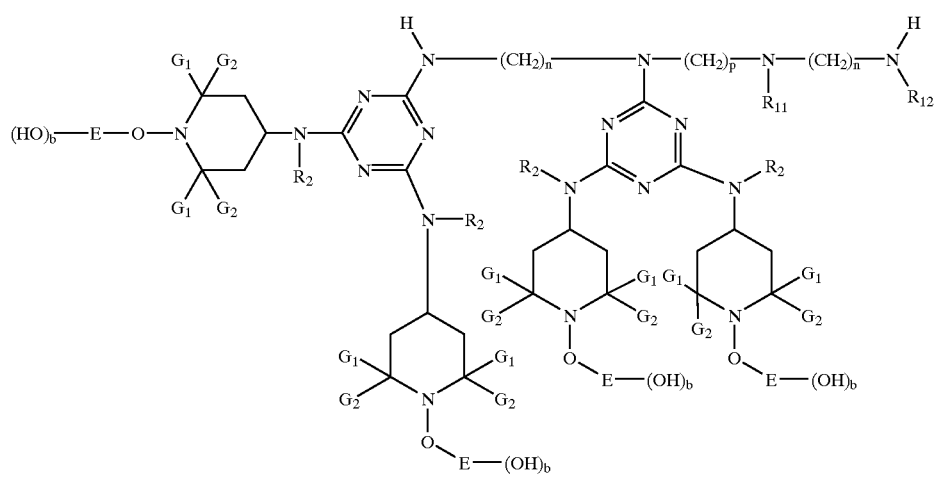
(12)
(13)
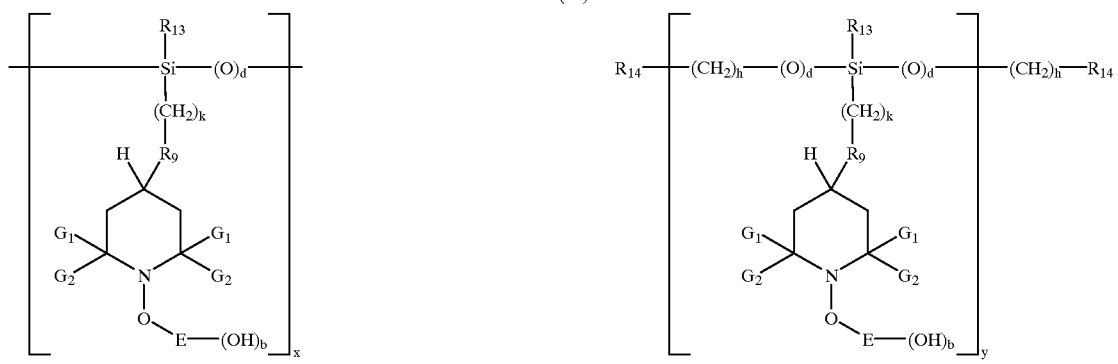
(14)
(15)
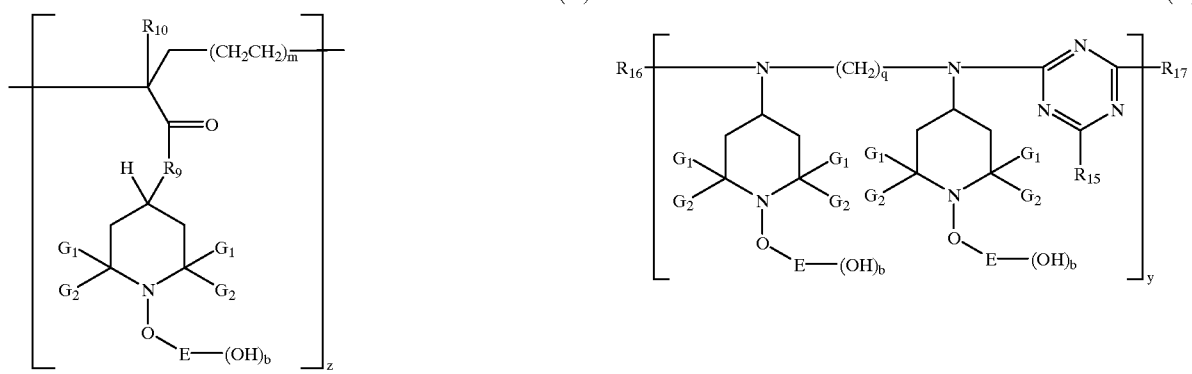
(16)
(17)
(18)
(19)
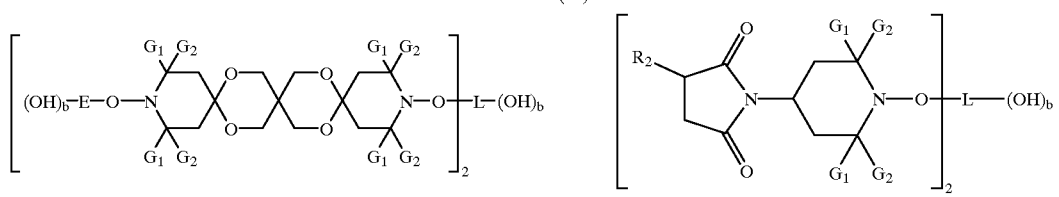

(20)
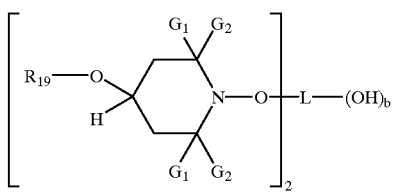

(21)
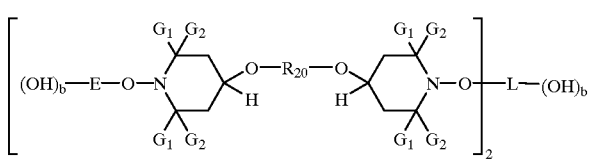

(22)
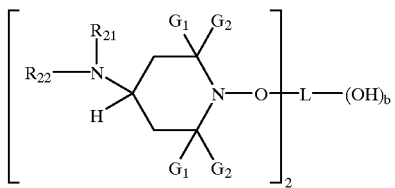

(23)
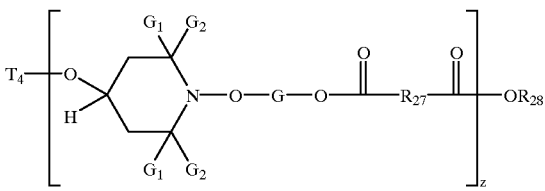

(26)
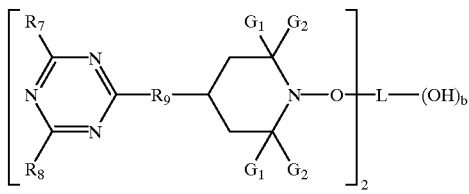

(27)
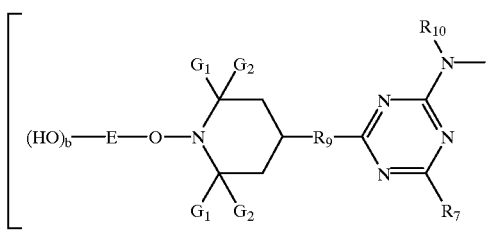

(28)
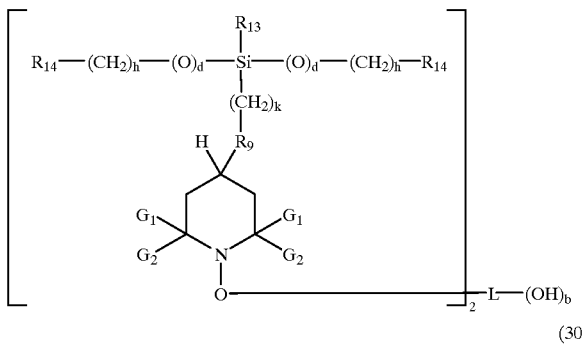

(29)
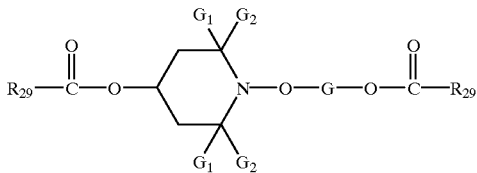

(30)
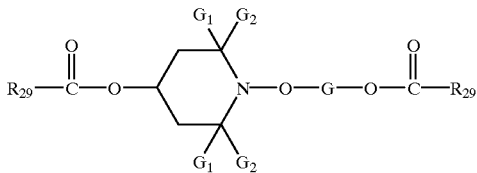

$G_1$ and $G_2$ are independently alkyl of 1 to 4 carbon atoms, or $G_1$ and $G_2$ together are pentamethylene; preferably $G_1$ and $G_2$ are each methyl;

E is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in E or L, and when b is 2 or 3, each hydroxyl group is attached to a different carbon atom of E or L; the two hindered amine groups are generally, but not always, attached to two different carbon atoms of L;

in each of the formulas (1) to (15)

m is 0 or 1;

$R_1$ is hydrogen, hydroxyl or hydroxymethyl;

$R_2$ is hydrogen, alkyl of 1 to 12 carbon atoms or alkenyl of 2 to 12 carbon atoms;

n is 1 to 4;

when n is 1, $R_3$ is alkyl of 1 to 18 carbon atoms, alkoxycarbonylalkylenecarbonyl of 4 to 18 carbon atoms, alkenyl of 2 to 18 carbon atoms, glycidyl, 2,3-dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;

when n is 2, $R_3$ is alkylene of 2 to 18 carbon atoms, a divalent acyl radical of an aliphatic or unsaturated aliphatic dicarboxylic or dicarbamic acid containing 2 to 18 carbon atoms, a divalent acyl radical of a cycloaliphatc dicarboxylic or dicarbamic acid containing 7 to 12 carbon atoms, or a divalent acyl radical of an aromatic dicarboxylic acid containing 8 to 15 carbon atoms;

when n is 3, $R_3$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;

when n is 4, $R_3$ is a tetravalent acyl radical of an aliphatic or unsaturated aliphatic tetracarboxylic acid, especially 1,2,3,4-butanetetracarboxylic acid, 1,2,3,4-but-2-enetetracarboxylic acid, 1,2,3,5-pentanetetracarboxylic acid and 1,2,4,5-pentanetetracarboxylic acid, or $R_3$ is a tetravalent acyl radical of an aromatic tetracarboxylic acid containing 10 to 18 carbon atoms;

p is 1 to 3, $R_4$ is hydrogen, alkyl of 1 to 18 carbon atoms or acyl of 2 to 6 carbon atoms;

when p is 1, $R_5$ is hydrogen, alkyl of 1 to 18 carbon atoms, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, an acyl radical of an aromatic carboxylic acid containing 7 to 15 carbon atoms, or $R_4$ and $R_5$ together are —$(CH_2)_5$CO—, phthaloyl or a divalent acyl radical of maleic acid;

when p is 2, $R_5$ is alkylene of 2 to 12 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

when p is 3, $R_5$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;

when n is 1, $R_6$ is alkoxy of 1 to 18 carbon atoms, alkenyloxy of 2 to 18 carbon atoms, —NHalkyl of 1 to 18 carbon atoms or —N(alkyl)$_2$ of 2 to 36 carbon atoms, when n is 2, $R_6$ is alkylenedioxy of 2 to 18 carbon atoms, alkenylenedioxy of 2 to 18 carbon atoms, —NH-alkylene-NH— of 2 to 18 carbon atoms or —N(alkyl)-alkylene-N(alkyl)— of 2 to 18 carbon atoms, or $R_6$ is 4-methyl-1,3-phenylenediamino, when n is 3, $R_6$ is a trivalent alkoxy radical of a saturated or unsaturated aliphatic triol containing 3 to 18 carbon atoms, when n is 4, $R_6$ is a tetravalent alkoxy radical of a saturated or unsaturated aliphatic tetraol containing 4 to 18 carbon atoms, $R_7$ and $R_8$ are independently chlorine, alkoxy of 1 to 18 carbon atoms, -O-$T_1$, amino substituted by 2-hydroxyethyl, —NH(alkyl) of 1 to 18 carbon atoms, —N(alkyl)$T_1$ with alkyl of 1 to 18 carbon atoms, or —N(alkyl)$_2$ of 2 to 36 carbon atoms, $R_9$ is a divalent oxygen atom, or $R_9$ is a divalent nitrogen atom substituted by either hydrogen, alkyl of 1 to 12 carbon atoms or $T_1$ $$T_1 = \begin{array}{c} G_1 \quad G_2 \\ \diagdown \diagup \\ \text{piperidine ring} \\ \diagup \diagdown \\ G_1 \quad G_2 \end{array} \!\!\!\!N\!\!-\!\!O\!\!-\!\!E\!\!-\!\!(OH)_b$$

$R_{10}$ is hydrogen or methyl, q is 2 to 8, $R_{11}$ and $R_{12}$ are independently hydrogen or the group $T_2$ $T_2 = $ [triazine-bis(piperidinyl) structure with substituents $R_2$, $G_1$, $G_2$, and —O—E—(OH)$_b$ groups]

$R_{13}$ is hydrogen, phenyl, straight or branched alkyl of 1 to 12 carbon atoms, alkoxy of 1 to 12 carbon atoms, straight or branched alkyl of 1 to 4 carbon atoms substituted by phenyl, cycloalkyl of 5 to 8 carbon atoms, cycloalkenyl of 5 to 8 carbon atoms, alkenyl of 2 to 12 carbon atoms, glycidyl, allyloxy, straight or branched hydroxyalkyl of 1 to 4 carbon atoms, or silyl or silyloxy substituted three times independently by hydrogen, by phenyl, by alkyl of 1 to 4 carbon atoms or by alkoxy of 1 to 4 carbon atoms;

$R_{14}$ is hydrogen or silyl substituted three times independently by hydrogen, by phenyl, by alkyl of 1 to 4 carbon atoms or by alkoxy of 1 to 4 carbon atoms;

d is 0 or 1;

h is 0 to 4;

k is 0 to 5;

x is 3 to 6;

y is 1 to 10;

z is an integer such that the compound has a molecular weight of 1000 to 4000 amu, $R_{15}$ is morpholino, piperidino, 1-piperizinyl, alkylamino of 1 to 8 carbon atoms, especially branched alkylamino of 3 to 8 carbon atoms such as tert-octylamino, —N(alkyl)$T_1$ with alkyl of 1 to 8 carbon atoms, or —N(alkyl)$_2$ of 2 to 16 carbon atoms, $R_{16}$ is hydrogen, acyl of 2 to 4 carbon atoms, carbamoyl substituted by alkyl of 1 to 4 carbon atoms, s-triazinyl substituted once by chlorine and once by $R_{15}$, or s-triazinyl substituted twice by $R_{15}$ with the condition that the two $R_{15}$ substituents may be different;

$R_{17}$ is chlorine, amino substituted by alkyl of 1 to 8 carbon atoms or by $T_1$, —N(alkyl)$T_1$ with alkyl of 1 to 8 carbon atoms, —N(alkyl)$_2$ of 2 to 16 carbon atoms, or the group $T_3$

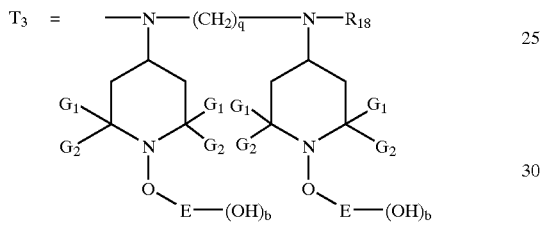

$R_{18}$ is hydrogen, acyl of 2 to 4 carbon atoms, carbamoyl substituted by alkyl of 1 to 4 carbon atoms, s-triazinyl substituted twice by —N(alkyl)$_2$ of 2 to 16 carbon atoms or s-triazinyl substituted twice by —N(alkyl)$T_1$ with alkyl of 1 to 8 carbon atoms;

L is straight or branched chain alkylene of 1 to 18 carbon atoms, cycloalkylene of 5 to 8 carbon atoms, cycloalkenylene of 5 to 8 carbon atoms, alkenylene of 3 to 18 carbon atoms, a straight or branched chain alkylene of 1 to 4 carbon atoms substituted by phenyl or by phenyl substituted by one or two alkyl of 1 to 4 carbon atoms, in formulas (16) to (28), $R_1$, $R_2$, $R_7$, $R_8$, $R_9$, $R_{10}$, $R_{13}$, $R_{14}$, d, h, k, m, q, and $T_1$ have the same meanings as in formulas (1) to (15);

$R_{19}$ is hydrogen, alkyl of 1 to 18 carbon atoms, alkenyl of 2 to 18 carbon atoms, glycidyl, 2,3dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;

$R_{20}$ is alkylene of 2 to 18 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

$R_{21}$ is hydrogen, alkyl of 1 to 18 carbon atoms or acyl of 2 to 6 carbon atoms;

$R_{22}$ is hydrogen, alkyl of 1 to 18 carbon atoms, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, an acyl radical of an aromatic carboxylic acid containing 7 to 15 carbon atoms, or $R_4$ and $R_5$ together are —(CH$_2$)$_5$CO—, phthaloyl or a divalent acyl radical of maleic acid;

$R_{23}$ is hydrogen, alkyl of 1 to 4 carbon atoms or acyl of 2 to 6 carbon atoms;

$R_{24}$ is alkylene of 2 to 18 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

$R_{25}$ is alkoxy of 1 to 18 carbon atoms, alkenyloxy of 2 to 18 carbon atoms, —NHalkyl of 1 to 18 carbon atoms or —N(alkyl)$_2$ of 2 to 36 carbon atoms, $R_{26}$ is alkylenedioxy of 2 to 18 carbon atoms, alkenylenedioxy of 2 to 18 carbon atoms, —NH-alkylene-NH— of 2 to 18 carbon atoms or —N(alkyl)-alkylene-N(alkyl)— of 3 to 18 carbon atoms, in formulas (29) and (30), G is a carbon centered diradical derived from a primary, secondary or tertiary alcohol G-OH, where z is as defined above, and G is straight or branched chain alkylene of 1 to 18 carbon atoms, cycloalkylene of 5 to 8 carbon atoms, cycloalkenylene of 5 to 8 carbon atoms, alkenylene of 3 to 18 carbon atoms, a straight or branched chain alkylene of 1 to 4 carbon atoms substituted by phenyl or by phenyl substituted by one or two alkyl of 1 to 4 carbon atoms, with the proviso that in formula (29) successive hindered amine moieties can be oriented in either a head to head or head to tail fashion;

$T_4$ is hydrogen or

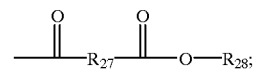

$R_{27}$ is a straight or branched chain alkylene of 1 to 18 carbon atoms, cycloalkylene or cycloalkenylene of 5 to 8 carbon atoms, phenylene or —NH-alkylene-NH— of 2 to 18 carbon atoms including 5-amino-1-aminomethy-1,3,3-trimethylcyclohexane and —NH-xylylene-NH—;

$R_{28}$ is alkyl of 1 to 4 carbon atoms;

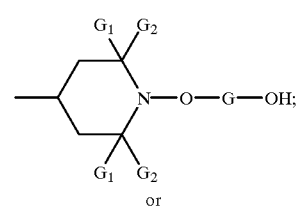

or

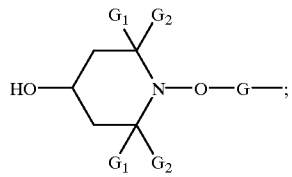

R$_{29}$ is a straight or branched chain alkyl or —NH-alkyl of 1 to 18 carbon atoms or —NH—cycloalkyl of 5 to 8 carbon atoms; and with the further proviso that in formulas (1) and (2), when b is 1, E is not methyl, ethyl, 2-propyl or 2-methyl-2-propyl.

Preferably, G$_1$ and G$_2$ are each methyl.

Preferably, in formulas (1) to (28), b is 1 or 2, most preferably 1.

When b is 1, E-OH and L-OH are respectively a carbon-centered radical or diradical formed preferably from 2-methyl-2-propanol, 2-propanol, 2,2-dimethyl-1-propanol, 2-methyl-2-butanol, ethanol, 1-propanol, 1-butanol, 1-pentanol, 1-hexanol, 1-nonanol, 1-decanol, 1-dodecanol, 1-octadecanol, 2-butanol, 2-pentanol, 2-ethyl-1-hexanol, cyclohexanol, cydooctanol, allyl alcohol, phenethyl alcohol or 1-phenyl-1-ethanol; most preferably E-OH and L-OH are formed from 2-methyl-2-propanol or cyclohexanol.

When b is 2, E-OH and L-OH are respectively a carbon-centered radical or diradical formed preferably from 1,2-ethanediol, 1,2-propanedial, 1,3-propanediol, 1,2-butanediol, 1,3-butanediol, 1,4-butanediol, 2,2-dimethyl-1,3-propanediol, 1,2-cyclohexanediol, 1,3-cyclohexanediol or 1,4-cyclohexanediol; most preferably E-OH and L-OH are formed from 1,4-butanediol, 2,2-dimethyl-1,3-propanediol, 1,2-cyclohexanediol, 1,3-cyclohexanediol or 1,4-cyclohexanediol.

When b is 3, E-OH and L-OH are respectively a carbon-centered radical or diradical formed from glycerol, 1,1,1-tris(hydroxymethyl)methane, 2-ethyl-2-(hydroxymethyl-1,3-propanediol, 1,2,4-butanetriol or 1,2,6-hexanetriol; most preferably E-OH and L-OH are formed from glycerol, 1,1,1-tris(hydroxymethyl)methane, 2-ethyl-2-(hydroxymethyl-1,3-propanediol.

Preferably in formulas (29) and (30), -G-O- is formed from ethanol, phenethyl alcohol, cyclohexanol or 2-methyl-2-propanol (=tert-butyl alcohol).

Preferably in formula (3), m is 0, R$_1$ is hydrogen or hydroxymethyl, and R$_2$ is hydrogen; or m is 1, R$_1$ is hydroxy or hydroxymethyl, and R$_2$ is hydrogen, methyl or ethyl.

Preferably in formula (5), R$_2$ is hydrogen or dodecyl.

Preferably in formula (6), n is 1 or 2, and when n is 1, R$_3$ is allyl, glycidyl, acryloyl, methacryloyl, octadecanoyl, hexadecanoyl, tetradecanoyl, methoxycarbonylpropionyl, methoxycarbonylbutyryl, methoxycarbonylpentanoyl or methoxycarbonylnonanoyl; or when n is 2, R$_3$ is succinyl, glutaryl, adipoyl, sebacoyl, 1,6-hexanedicarbamoyl or cis- or trans-5-carbamoyl-1-(carbamoylmethyl)-1,3,3-trimethylcyclohexane.

Preferably in formula (7), p is 1 or 2, and when p is 1, R$_4$ is hydrogen and R$_5$ is butyl; or R$_4$ and R$_5$ together are the divalent acyl radical of maleic acid; or when p is 2, R$_4$ is hydrogen or acetyl, and R$_5$ is 1,6-hexanediyl.

Preferably in formula (8), n is 1 or 2, and when n is 1, R$_6$ is ethoxy, 6methyl-1-heptyloxy, ethylamino, butylamino or octylamino; or when n is 2, R$_6$ is 1,2-ethanedioxy, 1,4-butanedioxy, ethylenediamino, hexamethylenediamino, or 4-methyl-1,3-phenylenediamino.

Preferably in formula (9), R$_7$ and R$_8$ are independently chlorine, octylamino, tert-octylamino or amino substituted by T$_1$ and ethyl, butyl or dodecyl; and R$_9$ is a divalent nitrogen atom substituted by ethyl, butyl or dodecyl.

Preferably in formula (10), q is 2, 4 or 6, R$_7$ is chlorine, octylamino, octadecylamino or amino substituted by T$_1$ and ethyl, butyl or dodecyl; and R$_{10}$ is hydrogen.

Preferably in formula (11), n is 3, p is 2, R$_2$ is ethyl, butyl or dodecyl; and one of R$_{11}$ or R$_{12}$ is T$_2$, and the other is hydrogen.

Preferably in formula (12), k is 3, R$_9$ is a divalent oxygen atom or is a divalent nitrogen atom substituted by ethyl, butyl or dodecyl, R$_{13}$ is hydrogen or methyl, and when d is 0, x is 5 or 6, and when d is 1, x is 3 or 4.

Preferably in formula (13), d is 0 or 1, h is 0–2, k is 0 or 3, y is 1–8, R$_9$ is a divalent oxygen atom or a divalent nitrogen atom substituted by ethyl, butyl or dodecyl, R$_{13}$ is hydrogen, methyl, ethyl, methoxy or ethoxy, and R$_{14}$ is hydrogen or trimethylsilyl.

Preferably in formula (14), R$_9$ is a divalent oxygen atom, R$_{10}$ is hydrogen or methyl, m is 0 and z is an integer such that the molecular weight of the compound is 1500–3000 amu.

Preferably in formula (15) q is 6, y is 1–7, R$_{15}$ is tert-octylamino, morpholino, amino substituted by T$_1$ and butyl, which may also be designated as T$_1$-butylamino, R$_{16}$ is hydrogen, acetyl, ethylcarbamoyl, 2,4-bis(dibutylamino)-s-triazinyl, 2,4-bis(diethylamino)-s-triazinyl, s-triazinyl substituted twice by T$_1$-butylamino or s-triazinyl substituted once by diethylamino or dibutylamino and once by T$_1$-butylamino, R$_{17}$ is dibutylamino, diethylamino, T$_1$-butylamino or R$_{17}$ is T$_3$ where R$_{18}$ is acetyl or ethylcarbamoyl.

Preferably in formula (17), m is 0, R$_1$ is hydrogen or hydroxymethyl, and R$_2$ is hydrogen; or m is 1, R$_1$ is hydroxy or hydroxymethyl, and R$_2$ is hydrogen or methyl.

Preferably in formula (19), R$_2$ is hydrogen or dodecyl.

Preferably in formula (20), R$_{19}$ is hydrogen, allyl, acryloyl, methacryloyl, octadecanoyl or hexadecanoyl.

Preferably in formula (21), R$_{20}$ is succinyl, glutaryl, adipoyl, sebacoyl, 1,6-hexanedicarbamoyl, or cis- or trans-5-carbamoyl-1-(carbamoylmethyl)-1,3,3-trimethylcyclohexane.

Preferably in formula (22), R$_{21}$ is hydrogen and R$_{22}$ is hydrogen or butyl; or R$_{21}$ and R$_{22}$ together are the divalent acyl radical of maleic acid.

Preferably in formula (23), R$_{23}$ is hydrogen or acetyl, and R$_{24}$ is ethylene or hexamethylene.

Preferably in formula (24), R$_{25}$ is ethoxy, 6-methyl-1-heptyloxy, ethylamino, butylamino or octylamino.

Preferably in formula (25), R$_{26}$ is 1,2-ethanedioxy, 1,4-butanedioxy, ethylenediamino or hexamethylenediamino.

Preferably in formula (26), R$_7$ and R$_8$ are independently chlorine, octylamino, tert-octylamino, octadecylamino, T$_1$-ethylamino, T$_1$-butylamino or T$_1$-dodecylamino, and R$_9$ is a divalent nitrogen atom substituted by ethyl, butyl or dodecyl.

Preferably in formula (27), q is 2, 4 or 6, R$_7$ is chlorine, octylamino, octadecylamino, T$_1$-ethylamino, T$_1$-butylamino or T$_1$-dodecylamino, and R$_{10}$ is hydrogen.

Preferably in formula (28), d is 0 or 1, h is 0–2, k is 0 or 3, R$_9$ is a divalent oxygen atom or a divalent nitrogen atom substituted by ethyl, butyl or dodecyl, R$_{13}$ is hydrogen, methyl, ethyl, methoxy or ethoxy, and R$_{14}$ is hydrogen or trimethylsilyl.

Preferably in formula (29), R$_{27}$ is ethylene, trimethylene, tetramethylene, octamethylene, 1,6-diaminohexane or 5amino-1-aminomethyl-1,3,3-trimethylcyclohexane; z is an integer such that the molecular weight of the compound is 1500–3000 amu, $R_{28}$ is methyl or ethyl, and G is ethylene, 1,2-cyclohexanediyl, 1,3-cyclohexanediyl, 1,4-cyclohexanediyl, —CH($C_6H_5$)CH2— or —$CH_2C(CH_3)_2$—.

Preferably in formula (30), $R_{29}$ is pentadecyl, heptadecyl, butylamino or cyclohexylamino.

Still more preferred embodiments of the instant invention are the compounds of formulas (1) to (30) where E-OH, L-OH and G-O- are formed from 2-methyl-2-propanol (=tert-butyl alcohol) or cyclohexanol.

Most preferably in formula (6), when n is 1, $R_3$ is acryloyl, methacrloyl, glycidyl, octadecanoyl, hexadecanoyl, methoxycarbonylpropionyl, methoxycarbonylbutyryl, methoxy-carbonylpentanoyl or methoxycarbonylnonanoyl; or when n is 2, $R_3$ is succinyl, glutaryl, adipoyl, sebacoyl, 1,6-hexanedicarbamoyl or cis- or trans-5carbamoyl-1-(carbamoylmethyl)-1,3,3-trimethylcyclohexane.

Most preferably in formula (7), p is 1 or 2, and when p is 1, $R_4$ is hydrogen and $R_5$ is hydrogen or butyl; or when p is 2, $R_4$ is hydrogen, and $R_5$ is 1,6-hexanediyl.

Most preferably in formula (9), $R_7$ is chlorine, octylamino or $T_1$-butylamino, $R_8$ is chlorine or $T_1$-butylamino, and $R_9$ is a divalent nitrogen atom substituted by butyl.

Most preferably in formula (10), q is 6, $R_7$ is $T_1$-butylamino; and $R_{10}$ is hydrogen.

Most preferably in formula (11), n is 3, p is 2, and one of $R_1$, or $R_{12}$ is $T_2$, and the other is hydrogen.

Most preferably in formula (12), k is 3, $R_9$ is a divalent oxygen atom, $R_{13}$ is hydrogen or methyl, and d is 0, x is 5 or 6, and when d is 1, x is 3 or 4.

Most preferably in formula (13), d is 0 or 1, h is 0–2, k is 0 or 3, y is 1–8, $R_9$ is a divalent oxygen atom, $R_{13}$ is hydrogen, methyl, ethyl, methoxy or ethoxy, and $R_{14}$ is hydrogen or trimethylsilyl.

Most preferably in formula (15) q is 6, y is 1–7, $R_{15}$ is $T_1$-butylamino, $R_{16}$ is hydrogen, acetyl, ethylcarbamoyl, 2,4-bis(dibutylamino)-s-triazinyl, 2,4-bis(diethylamino)-s-triazinyl, s-triazinyl substituted twice by $T_1$-butylamino or s-triazinyl substituted once by diethylamino or dibutylamino and once by $T_1$-butylamino, $R_{17}$ is dibutylamino, diethylamino, $T_1$-butylamino or $R_{17}$ is $T_3$ where $R_{18}$ is acetyl or ethylcarbamoyl.

Most preferably in formula (20), $R_{19}$ is hydrogen, octadecanoyl or hexadecanoyl.

Most preferably in formula (22), $R_{21}$ is hydrogen and $R_{22}$ is hydrogen or butyl.

Most preferably in formula (23), $R_{23}$ is hydrogen, and $R_{24}$ is hexamethylene.

Most preferably in formula (26), $R_7$ is chlorine, octylamino or $T_1$-butylamino, $R_8$ is chlorine or $T_1$-butylamino, and $R_9$ is a divalent nitrogen atom substituted by butyl.

Most preferably in formula (27), q is 6, $R_7$ is $T_1$-butylamino, and $R_9$ is a divalent nitrogen atom substituted by butyl.

Most preferably in formula (29), $R_{27}$ is ethylene, trimethylene, tetramethylene or octamethylene, z is an integer such that the molecular weight of the compound is 1500 to 2000 amu, and $R_{28}$ is methyl.

Most preferably in formula (30), $R_{29}$ is pentadecyl or heptadecyl.

Still more preferred embodiments of the instant invention are the compounds of formulas (1) to (30) where E-OH, L-OH and -G-O- are formed from 2-methyl-2-propanol (=tert-butyl alcohol).

Especially preferred compounds of formula (6) are those where n is 1, $R_3$ is acryloyl, methacryloyl, glycidyl, octadecanoyl, hexadecanoyl, methoxycarbonylpropionyl or methoxycarbonylbutyryl, and where n is 2, $R_3$ is succinyl, glutaryl, adipoyl or sebacoyl.

Especially preferred compounds of formula (7) are those where $R_4$ is hydrogen, and when p is 1, $R_5$ is hydrogen or butyl, or when p is 2, $R_5$ is hexamethylene.

Especially preferred compounds of formula (9) are those where $R_7$ is chlorine, octylamino or $T_1$-butylamino, $R_8$ is $T_1$-butylamino, and $R_9$ is a divalent nitrogen atom substituted by butyl.

Especially preferred compounds of formula (10) are those where q is 6, $R_7$ is $T_1$-butylamino and $R_{10}$ is hydrogen.

Especially preferred compounds of formula (11) are those where n is 3, p is 2, one of $R_{11}$ or $R_{12}$ is $T_2$ and the other is hydrogen.

Especially preferred compounds of formula (12) are those where d is 1, k is 3, x is 3 or 4, $R_9$ is divalent oxygen atom, and $R_{13}$ is methyl.

Especially preferred compounds of formula (13) are those where k is 3, y is 4–8. $R_9$ is a divalent oxygen atom, $R_{13}$ is hydrogen or methyl, d and h are 0, $R_{14}$ is hydrogen, or d is 1 and h is 0, and $R_{14}$ is trimethylsilyl.

Especially preferred compounds of formula (14) are those where m is 0, $R_9$ is a divalent oxygen atom, $R_{10}$ is hydrogen or methyl, and z is an integer such that the molecular weight of the compound is 1500–3000 amu.

Especially preferred compounds of formula (15) are those where q is 6, y is 1–7, $R_{15}$ is $T_1$-butylamino, $R_{16}$ is hydrogen, acetyl, ethylcarbamoyl, 2,4-bis(dibutylamino)-s-triazinyl, 2,4-bis(diethylamino)-s-triazinyl, s-triazinyl substituted twice by $T_1$-butylamino or s-triazinyl substituted once by diethylamino or dibutylamino and once by $T_1$-butylamino, $R_{17}$ is dibutyl-amino, diethylamino, or $T_3$ where $R_{18}$ is acetyl or ethylcarbamoyl.

Especially preferred compounds of formula (20) are those where $R_{19}$ is hydrogen, octadecanoyl or hexadecanoyl.

Especially preferred compounds of formula (21) are those where $R_{20}$ is succinyl, glutaryl, adipoyl or sebacoyl.

Especially preferred compound of formula (30) is that where $R_{29}$ is heptadecyl.

The instant invention also pertains to a polymer composition containing an effective stabilizing amount of one or more compounds selected from the compounds of formula (1) to formula (30) as described above.

Preferably, the organic material is a natural, semi-synthetic or synthetic polymer, especially a thermoplastic polymer.

Most preferably, the polymer is a polyolefin, especially a thermoplastic polyolefin useful in automotive coatings and applications or a urethane based automotive coating.

The compounds of this invention exhibit superior hydrolytic stability, handling and storage stability as well as good resistance to extractability when present in a stabilized composition.

In general polymers which can be stabilized include

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbomene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisabon medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylenelpropylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethyleneloctene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbomene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadienelalkyl acrylate, styrene/butadiene/alkyl methacrylate, styrene/maleic anhydride, styrene/-acrylonitrile/methyl acrylate; mixtures of high impact strength of styrene copolymers and another polymer, for example a polyacrylate, a diene polymer or an ethylene/propyleneldiene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrilel butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/-EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrenelbutadiene copolymers.

31. Polysiloxanes such as the soft, hydrophilic polysiloxanes described, for example, in U.S. Pat. No. 4,259,467; and the hard polyorganosiloxanes described, for example, in U.S. Pat. No. 4,355,147.

32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

33. Radiation curable compositions containing ethylenically unsaturated monomers or oligomers and a polyunsaturated aliphatic oligomer.

34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated Monophenols, for Example,
  2,6-di-tert-butyl-4-methylphenol
  2-tert-butyl-4,6-dimethylphenol
  2,6-di-tert-butyl-4-ethylphenol
  2,6-di-tert-butyl-4-n-butylphenol
  2,6-di-tert-butyl-4-i-butylphenol
  2,6-di-cyclopentyl-4-methylphenol
  2-(α-methylcyclohexyl)-4,6-dimethylphenol
  2,6-di-octadecyl-4-methylphenol
  2,4,6-tri-cyclohexylphenol
  2,6-di-tert-butyl-4-methoxymethylphenol 1.2. Alkylated Hydroquinones, for Example
  2,6-di-tert-butyl-4-methoxyphenol
  2,5-di-tert-butyl-hydroquinone
  2,5-di-tert-amyl-hydroquinone
  2,6-diphenyl-4-octadecyloxyphenol 1.3. Hydroxylated Thiodiphenyl Ethers, for Example
  2,2'-thio-bis-(6-tert-butyl-4-methylphenol)
  2,2'-thio-bis-(4-octylphenol)
  4,4'-thio-bis-(6-tert-butyl-3-methylphenol)
  4,4'-thio-bis-(6-tert-butyl-2-methylphenol)

1.4. Alkylidene-bisphenols, for Example
  2,2'-methylene-bis-(6-tert-butyl-4-methylphenol)
  2,2'-methylene-bis-(6-tert-butyl-4-ethylphenol)
  2,2'-methylene-bis-[4-methyl-6-(α-methylcyclohexyl)-phenol]
  2,2'-methylene-bis-(4-methyl-6-cyclohexylphenol)
  2,2'-methylene-bis-(6-nonyl-4-methylphenol)
  2,2'-methylene-bis-[6-(α-methylbenzyl)-4-nonylphenol]
  2,2'-methylene-bis-[6-(α,α-dimethylbenzyl)-4-nonylphenol]
  2,2'-methylene-bis-(4,6-di-tert-butylphenol)

2,2'-ethylidene-bis-(4,6-di-tert-butylphenol)

2,2'-ethylidene-bis-(6-tert-butyl-4-isobutylphenol)

4,4'-methylene-bis-(2,6-di-tert-butylphenol)

4,4'-methylene-bis-(6-tert-butyl-2-methylphenol)

1,1-bis-(5-tert-butyl-4-hydroxy-2-methylphenyl)-butane 2,6-di-(3-tert-butyl-5-methyl-2-hydroxybenzyl)-4-methylphenol 1,1,3-tris-(5-tert-butyl-hydroxy-2-methylphenyl)-butane 1,1-bis-(5-tert-butyl-4-hydroxy-2-methylphenyl)-3-n-dodecylmercaptobutane ethyleneglycol bis-[3,3-bis-(3'-tert-butyl-4'-hydroxyphenyl)-butyrate]

di-(3-tert-butyl-4-hydroxy-5-methylphenyl)-dicyclopentadiene di-[2-(3'-tert-butyl-2'-hydroxy-5'-methylbenzyl)-6-tert-butyl-4-methylpheny]terephthalate.

1.5. Benzyl Compounds, for Example, 1,3,5-tri-(3,5-di-tert-butyl-4-hydroxybenzyl)-2,4,6trimethylbenzene di-(3,5-di-tert-butyl-4-hydroxybenzyl)sulfide 3,5-di-tert-butyl-4-hydroxybenzyl-mercapto-acetic acid isooctyl ester bis-(4-tert-buty-3-hydroxy-2,6-dimethylbenzyl)dithiol terephthalate 1,3,5-tris-(3,5-di-tert-butyl-4-hydroxybenzyl) isocyanurate 1,3,5-tris-(4-tert-butyl-3-hydroxy-2,6-dimethylbenzyl) isocyanurate 3,5di-tert-butyl-4-hydroxybenzyl-phosphoric acid diocta-decyl ester 3,5-di-tert-butyl-4-hydroxybenzyl-phosphoric acid monoethyl ester, calcium-salt 1.6. Acylaminoghenols, for Example, 4-hydroxy-lauric acid anilide 4-hydroxy-stearic acid anilide 2,4-bis-octylmercapto-6-(3,5-tert-butyl-4-hydroxyanilino)-s-triazine octyl-N-(3,5-di-tert-butyl-4-hydroxyphenyl)-carbamate 1.7. Esters of β-(3,5-di-tert-butyl-4-hydroxyphenyl)-propionic Acid with Monohydric or Polyhydric Alcohols, for Example,

| methanol | diethylene glycol |
|---|---|
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methvlphenyl)-propionic Acid with Monohydric or Polyhydric Alcohols, for Example,

| methanol | diethylene glycol |
|---|---|
| octadecanol | triethylene glycol |
| 1,6-hexanediol | pentaerythritol |
| neopentyl glycol | tris-hydroxyethyl isocyanurate |
| thiodietnylene glycol | di-hydroxyethyl oxalic acid diamide |
| triethanolamine | triisopropanolamine |

1.9. Amides of β-(3,5-di-tert-butyl-4-hydroxyphenyl)-propionic Acid for Example, N,N'-di-(3,5-di-tert-butyl-4-hydroxyphenylpropionyl)-hexamethylenediamine N,N'-di-(3,5-di-tert-butyl-4-hydroxyphenylpropionyl)-trimethylenediamine N,N'-di-(3,5-di-tert-butyl-4-hydroxyphenylpropionyl)-hydrazine 1.10 Diarylamines, for Example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV Absorbers and Light Stabilizers 2.1. 2-(2'-Hydroxyphenyl)-benzotriazoles, for Example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-,3'-dodecyl-5'-methyl-, 3'-tert-butyl-5'-(2-octyloxycarbonyl)ethyl-, dodecylated-5'-methyl derivatives; and 2-(2-hydroxy-3-α-cumyl-5-tert-octylphenyl)-2H-benzotriazole.

2.2. 2-Hydroxy-benzophenones, for Example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivabves.

2.3. Esters of Optionally Substituted Benzoic Acids for Example, phenyl salicylate, 4-tert-butylphenyl salicylate, octylphe-nyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel Compounds, for Example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically Hindered Amines, for Example bis-(2,2,6,6-tetramethylpiperidyl)sebacate, bis-(1,2,2,6,6-pentamethylpiperidyl)sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)- nitrilotriacetate, tetrakis-(2,2,6,6-tetramethyl-4-piperidyl)1,2,3,4-butanetetracarboxylate, 1,1'(1,2-ethanediyl)-bis-(3,3,5,5-tetramethylpiperazinone), bis (1-octyloxy-2,2,6,6-tetramethylpiperidin-4-yl) sebacate. 2-(2-hydroxyethylamino)-4,6-bis{N-[1-(cyclohexyloxy)-2,2,6,6-tetramethylpiperidin-4-yl]-butylamino-s-triazine, oligomer of N-{[2-(N-2,2,6,6-tetramethylpiperidin-4-yl)butylamino]-s-triazin-4-yl}-N,N'-bis(2,2,6,6-tetramethylpiperidin-4-yl)-1,6-hexanediamine terminated with 2,4-bis(dibutylamino)-s-triazin-6-yl, N,N',N"-tris{2,4-bis[N-(1,2,2,6,6-pentamethylpiperidin-4-yl)butylamino]-s-triazin-6-yl}-3,3'-ethylenediiminodipropylamine, N,N',N'''-tris{2,4-bis[N-(1,2,2,6,6-pentamethylpipeddin-4-yl) butylamino]-s-triazin-6-yl}-3,3'-ethylenediiminodipropylamine and N,N',N",N'''-tetrakis{2,4-bis[N-(1,2,2,6,6-pentamethylpiperidin-4-yl)butylamino]-s-triazin-6-yl}-3,3'-ethylenediiminodipropylamine; N,N',N'''-tris{2,4-bis [N-(1-cyclohexyloxy-2,2,6,6-tetramethypipeddin-4-yl) butylamino]-s-triazin-6-yl}-3,3'-ethylenediiminodipropylamine, N',N,N'''-tris{2,4-bis [N-(1-cyclohexyloxy-2,2,6,6-tetramethylpiperidin-4-yl)butylamino]-s-triazin-6-yl}-3,3'-ethylenediiminodipropylamine and N,N',N",N'''-tetrakis{2,4-bis[N-(1-cyclohexyloxy-2,2,6,6-tetramethylpiperdin-4-yl)butylamino]-s-triazin-yl}-3,3'-ethylenediiminodipropylamine.

2.7. Oxalic Acid Diamides, for Example, 4,4'-di-octyloxy-oxanilide, 2,2'-di-octyloxy-5,5'-di-tert-butyl-oxanilide, 2,2'-di-dodecyloxy-5,5'-di-tert-butyl-xanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for Example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal Deactivators, for Example

N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl) hydrazine, 3-salicyloylamino-1,2,4-triazole, bis-benzylidene-oxalic acid dihydrazide.

4. Phosphites and Phosphonites, for Example triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl)phosphite, di-isodecylpentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which Destroy Peroxide, for Example esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for Example

N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyt-N-octadecylhydroxylamine, N,N-dialkylhydroxylamine derived from hydrogenated tallow amine.

7. Nitrones, for Example

N-benzyl-alpha-phenyl nitrone, N-ethyl-alpha-methyl nitrone, N-octylalpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecyinitrone, N-hexadecyl-alpha-heptadecyl nitrone, N-octadecyl-alpha-pentadecyl nitrone, N-heptadecylalpha-heptadecyl nitrone, N-octadecyl-alpha-hexadecyl nitrone, nitrone derived from N,N-dialkylhydroxylamine derived from hydrogenated tallow amine.

8. Polyamide Stabilizers, for Example copper salts in combination with iodides and/or phosphorus compounds and salts of divalent manganese.

9. Basic co-stabilizers, for Example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating Agents, for Example 4-tert-butyl-benzoic acid, adipic acid, diphenylacetic acid.

11. Fillers and Reinforcing Agents, for Example calcium carbonate, silicates, glass fibers, asbestos, talc, kaolin, mica, barium sulfate, metal oxides and hydroxides, carbon black, graphite.

12. Other Additives, for Example plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and Indolinones, for Example those disclosed in U.S. Pat. No. 4,325,863, U.S. Pat. No. 4,338,244 or U.S. Pat. No. 5,175,312, or 3-[4-(2-acetoxyethoxy)phenyl]-5,7-di-tert-butyl-benzofuran-2-one, 5,7-di-tert-butyl-3-[4-(2-stearoyloxyethoxy) phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The co-stabilizers, with the exception of the benzofuranones listed under 11, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list) and peroxide-destroying compounds (item 5.) of the list.

Additional additives (stabilizers) which are also particularly preferred are benzofuran-2-ones, such as described, for example, in U.S. Pat. No. 4,325,863, U.S. Pat. No. 4,338,244 or U.S. Pat. No. 5,175,312.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl) benzene, 3,6-dioxaoctamethylene bis(3-methyl-5-tert-butyl-4-hydroxyhydrocinnamate), 2,6-di-tert-buty-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3,-tris(2-methyl-4-hydroxy-5-tert-butylphenyl)butane, 1,3,5-tris-[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis [2-(3,5-di-tert-butyl-4-hydroxyhydrocinnamoyloxy)-ethyl]-oxamide.

A most preferred phenolic antioxidant is neopentanetetrayl tetrakis(3,5-di-tert-buty-4-hydroxyhydrocinnamate), n-octadecyl 3,5-di-tert-butyl-4-hydroxyhydrocinnamate, 1,3,5-tri-methyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl)nitrilotriacetate, 1,2-bis(2,2,6,6-tetramethyl-3-oxopiperazin-4-yl)ethane, 2,2,4,4-tetramethyl-7-oxa-3,20diaza-21-oxodispiro[5.1.11.2] heneicosane, polycondensation product of 2,4-dichloro-6-tert-octylamino-s-triazine and 4,4'-hexamethylenebis (amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-1,2,2,6,6-pentamethylpiperidin-4-yl)-amino-s-triazin-2-yl]-1,10-diamino-4,7-diazadecane, polycondensation product of 2,4-dichloro-6-morpholino-s-triazine and 4,4'-hexamethylenebis(amino-1,2,2,6,6-pentamethylpiperidine), mixed [2,2,6,6-tetramethylpiperidin-4-yl/β,β,β',β'-tetramethyl-3,9-(2,4,8,10-tetraoxaspiro[5.5]-undecane) diethyl]1,2,3,4-butanetetracarboxylate, mixed [1,2,2,6,6-pentamethylpiperdin-4-yl/β,β,β',β'-tetramethyl-3,9-(2,4,8,10-tetraoxaspiro[5.5]undecane)diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,8,6-tetramethylpiperidin-4-yl-n-dodecylsuccinimide, 1-acetyl-3-dodecyl-7,7,9,9-tetramethyl-1,3,8triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2 2,6,6-tetramethylpiperidin-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine, 2-(2-hydroxyethylamino)-4,6-bis{N-[1-(cyclohexyloxy)-2,2,6,6-tetramethylpiperidin-4-yl]-butylamino-s-triazine, oligomer of N-{[2-(N-2,2,6,6-tetramethylpiperidin-4-yl) butylamino]-s-triazin-4-yl}-N,N'-bis(2,2,6,6-tetramethylpiperidin-4-yl)-1,6-hexanediamine terminated with 2,4-bis(dibutylamino)-s-triazinlyl, N,N',N''-tris{2,4-bis [N-(1,2,2,6,6pentamethylpiperidin-4-yl)butylamino]-s-triazin-6-yl}-3,3'-ethylenediiminodipropylamine, N,N',N'''-tris{2,4-bis[N-(1,2,2,6,6-pentamethylpipeddin-4-yl) butylamino]-s-triazin-6-yl}-3,3'-ethylenediiminodipropylamine and N,N',N'',N'''-tetrakis{2,4-bis[N-(1,2,2,6,6-pentamethylpiperidin-4-yl)butylamino]-s-triazin-yl}-3,3'-ethylenediiminodipropylamine; N,N',N''-tris{2,4-bis[N-(1-cyclohexyloxy- 2,2,6,6-tetramethylpiperidin-4-yl)butylamino]-s-triazin-6-yl}-3,3'-ethylenediiminodipropylamine, N,N',N'''-tris{2,4-bis[N-(1-cyclohexyloxy-2,2,6,6-tetramethylpipeddin-4-yl) butylamino]-s-triazin-6-yl}3,3'-ethylenediiminodipropylamine, N,N',N'',N'''-tetrakis{2,4-bis[N-(1-cyclohexyloxy-2,2,6,6-tetramethylpipeddin-4-yl) butylamino]-s-triazin-6-yl}-3,3'-ethylenediiminodipropylamine, oligomer of N-{2-[(1-propoxy-2,2,6,6-tetramethylpiperidin-4-yl)butylamino]-s- triazin4-yl}-N,N'-bis(1-propoxy-2,2,6,6-tetramethylpiperidin-4-yl)-1,6-hexanediamine terminated with 2,4-bis(dibutylamino)-s-triazin-6-yl, or the condensation product of 2-morpholino-4,6-dichloro-s-triazine with N,N'-bis(1,2,2,6,6-pentamethylpiperidin-4-yl)-1,6-hexanediamine.

A most preferred hindered amine compound is bis(2,2,6,6-tetramethylpiperidin-4-yl) sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-tert-octylamino-s-triazine and 4,4'-hexamethylenebis(amino-2,2,6,6-tetramethylpiperidine), N,N',N",N'''-tetrakis[(4,6-bis(butyl-(1,2,2,6,6-pentamethylpiperidin-4-yl)amino)-s-triazine-2-yl]-1,10-diamino-4,7-diazadecane di-(1-octyloxy-2,2,6,6-tetramethylpiperidin-4-yl)sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cydohexyloxy-2,2,6,6-tetramethylpiperidin-4-yl)imino], or 2,4,6-tris[N-(1-cyclohexyloxy-2,2,6,6-tetramethylpiperidin-4-yl-n-butylamino]-s-triazine.

The instant composition can additionally contain another UV absorber selected from the group consisting of the s-triazines, the oxanilides, the hydroxybenzophenones, benzoates and the α-cyanoacrylates.

Particularly, the instant composition may additionally contain an effective stabilizing amount of at least one other 2-hydroxyphenyl-2H-benzotriazole; another tris-aryl-s-triazine; or hindered amine or mixtures thereof.

Preferably, the 2-hydroxyphenyl-2H-benzotriazole is selected from the group consisting of 2-(2-hydroxy-3,5-di-tert-amylphenyl)-2H-benzotriazole;

2-[2-hydroxy-3,5-di(α,α-dimethylbenzyl)phenyl]-2H-benzotiazole;

2-[2-hydroxy-3-(α,α-dimethylbenzyl)-5-tert-octylphenyl]-2H-benzotriazole;

2-{2-hydroxy-3-tert-butyl-5-[2-(omega-hydroxy-octa(ethyleneoxy)carbonyl)ethyl]phenyl}-2H-benzotriazole; and 2-{2-hydroxy-3-tert-butyl-5-[2-(octyloxy)carbonyl)ethyl]phenyl}-2H-benzotriazole.

Preferably the 2-hydroxyphenyl-2H-benzotriazole may also be selected from the group consisting of (a) 5-trifluoromethyl-2-(2-hydroxy-3-α-cumyl-5-tert-octylphenyl)-2H-benzotriazole;

(b) 5-trifluoromethyl-2-(2-hydroxy-5-tert-octylphenyl)-2H-benzotriazole;

(c) 5-trifluoromethyl-2-(2-hydroxy-3,5-di-tert-octylphenyl)-2H-benzotriazole;

(d) 2,2'-methylene-bis[6-(5-trifluoromethyl-2H-benzotriazol-2-yl)-4-tert-octylphenol];

(e) methylene-2-[4-tert-octyl-6-(2H-benzottiazol-2-yl)phenol]2'-[4-tert-octyl-6-(5-trifluromethyl-2H-benzotriazol-2-yl)phenol];

(f) 3-(5-trifluoromethyl-2H-benzotazol-2-y)-5-tert-butyl-4-hydroxyhydrocinnamic acid;

(g) methyl 3-(5-trifluoromethyl-2H-benzotriazol-2-yl)-5-tert-butyl-4-hydroxyhydrocinnamate;

(h) isooctyl 3-(5-trifluoromethyl-2H-benzotriazol-2-yl)-5-tert-butyl-4-hydroxyhydrocinnamate;

(i) 5-trifluoromethyl-2-[2-hydroxy-5-(3-hydroxypropyl)phenyl]-2H-benzotriazole;

(j) 5-trifluoromethyl-2-[2-hydroxy-5-(3-acryloyloxypropyl)phenyl]-2H-benzotriazole;

(k) 5-trifluoromethyl-2-[2-hydroxy-5-(3-methacryloyloxypropyl)phenyl]-2H-benzotriazole;

(l) 5-trifluoromethyl-2-[2-hydroxy-5-(3-acrylylaminopropyl)phenyl]-2H-benzotriazole;

(m) 5-trifluoromethyl-2-[2-hydroxy-5-(3-methacrylylaminopropyl)phenyl]-2H-benzotriazole;

(n) 5-trifluoromethyl-2-(2-hydroxy-3-α-cumyl-5-tert-butylphenyl)-2H-benzotriazole;

(o) 5-trifluoromethyl-2-(2-hydroxy-3-α-cumyl-5-nonylphenyl)-2H-benzotriazole;

(p) 5-trifluoromethyl-2-[2-hydroxy-3-α-cumyl-5-(2-hydroxyethyl)phenyl]-2H-benzotriazole;

(q) 5-trifluoromethyl-2-[2-hydroxy-3-α-cumyl-5-(3-hydroxypropyl)phenyl]-2H-benzotriazole;

(r) 5-trifluoromethyl-2-(2-hydroxy-3,5-di-tert-amylphenyl)-2H-benzotriazole;

(s) 5-trifluoromethyl-2-(2-hydroxy-3,5-di-tert-butylphenyl)-2H-benzotriazole;

(t) 5-trifluoromethyl-2-(2-hydroxy-3-dodecyl-5-methylphenyl)-2H-benzotriazole;

(u) 5-trifluoromethyl-2-[2-hydroxy-3-tert-butyl-5-(3-hydroxypropyl)phenyl]-2H-benzotriazole;

(v) 5-trifluoromethyl-2-[2-hydroxy-3-tert-butyl-5-(2-hydroxyethyl)phenyl]-2H-benzotriazole;

(w) 5-trifluoromethyl-2-[2-hydroxy-5-(2-hydroxyethyl)phenyl]-2H-benzotriazole;

(x) 5-trifluoromethyl-2-(2-hydroxy-3,5-di-α-cumylphenyl)-2H-benzotriazole;

(y) 5-fluoro-2-(2-hydroxy-3,5-di-α-cumylphenyl)-2H-benzotriazole;

(z) 5-butylsulfonyl-2-(2-hydroxy-3,5-di-α-cumylphenyl)-2H-benzotriazole;

(aa) 5-butylsulfonyl-2-(2-hydroxy-3,5-di-tert-butylphenyl)-2H-benzotriazole;

(bb) 5-butylsulfonyl-2-(2-hydroxy-3,5-di-tert-octylphenyl)-2H-benzotriazole; and (cc) 5-phenylsulfonyl-2-(2-hydroxy-3,5-di-tert-butylphenyl)-2H-benzotriazole.

Preferably, the other tris-aryl-s-triazine is selected from the group consisting of 2,4-bis(2,4-dimethylphenyl)-6-(2-hydroxy-4-octyloxyphenyl)-s-triazine;

2,4-diphenyl-6-(2-hydroxy-4-hexyloxyphenyl)-s-triazine;

2,4-bis(2,4-dimethylphenyl)-6-[2-hydroxy-4-(3-do-/tri-decyloxy-2-hydroxypropoxy)phenyl]-s-triazine; and 2-(2-hydroxyethylamino)-4,6-bis[N-butyl-N-(1-cyclohexyloxy-2,2,6,6-tetramethylpiperidin-4-yl)amino]-s-triazine.

The acrylic resin lacquers which can be stabilized against light, moisture and oxygen in accordance to the instant invention are conventional acrylic resin stoving lacquers or thermosetting resins including acrylic/melamine systems which are described, for example, in H. Kittel's "Lehrbuch and Beschichtungen", Vol. 1, Part 2 on pages 735 and 742 (Berlin 1972), "Lackkunstharze" (1977) by H. Wagner and H. F. Sarx on pages 229–238, and in S. Paul's "Surface Coatings: Science and Technology", (1985).

The polyester lacquers which can be stabilized against the action of light and moisture are conventional stoving lacquers described e.g. in H. Wagner and H. F. Sarx, op. cit., on pages 86–99.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycoluril resins, blocked or unblocked isocyanates or epoxy resins. Other lacquers which can be stabilized include those with crosslinkable functionalities such as carbamate and siloxane.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

Although major emphasis in this application is directed to acid-catalyzed baked finishes, it is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

The amount of instant stabilizer compound used is 0.1 to 5% by weight, based on the solvent-free binder, preferably 0.5 to 2% by weight. The binders can be dissolved or dispersed in customary organic solvents or in water or can be solvent-free.

When used in two-coat finishes, the compounds of the instant invention can be incorporated in the clear coat or both in the clear coat and in the pigmented base coat.

To attain maximum light stability, the concurrent use of other conventional light stabilizers can be advantageous. Examples are UV absorbers of the benzophenone, benzotriazole, acrylic acid derivatives, oxalanilide, aryl-s-triazine or metal-containing types (e.g. organic nickel compounds). In two-coat systems, these additional light stabilizers can be added to the clear coat and/or the pigmented base coat.

If such combinations of stabilizers are used, the sum of all light stabilizers is 0.2 to 20% by weight, preferably 0.5 to 5% by weight, based on the film-forming resin.

When water-soluble, water miscible or water dispersible coating are desired ammonium salts of acid groups present in the resin are formed. Powder coating composition can be prepared by reacting glycidyl methacrylate with selected alcohol components.

It is also contemplated that the instant compounds would find particular value when used with water-soluble inks and related polar oriented utilities where the presence of the OH moiety would provide for better compatibility and properties related to such aqueous environments.

The instant compounds are also useful in the stabilization of acid catalyzed thermoset resins which are disclosed in U.S. Pat. No. 5,112,890, the relevant parts of which are incorporated herein by reference.

These resins are used in baked enamels or stoving lacquers. Hindered amine light stabilizaers are well known to be effective in stabilizing a host of organic substrates including polymers from the deleterious effects of oxygen and light. Such hindered amine light stabilizers have been used in the stabilization of hot-crosslinkable alkyd or acrylic metallic stoving lacquers (see U.S. Pat. No. 4,426,472) and in stabilizing acid-catalyzed stoving lacquers based on hot-crosslinkable acrylic polyester or alkyl resins (see U.S. Pat. Nos. 4,344,876 and 4,426,471). None of the hindered amine light stabilizers of these patents possess structures having an O-substituted hydroxyl group substituted directly on the N-atom of the hindered amine. The instant compounds have such substitution and additionally are even less basic than the NOR compounds described in U.S. Pat. No. 5,112,890 as is seen in instant working Example 114.

In their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and recipitation of the salt and to a reduced level of cure and to reduced light protective action and poor resistance to moisture.

The acid catalyzed thermoset enamels must be stabilized in order to function acceptably in end-use applications. The stabilizers used are hindered amines, preferably those substituted on the N-atom by an inert blocking group in order to prevent precipitation of the basic amine with the acid catalyst with a concomitant retardation in cure, optionally in combination with UV absorbers as described above.

The stabilizers are needed to impart greater retention of durability to the cured enamels (as measured by 20° gloss, distinction of image, cracking or chalking); the stabilizers must not retard cure (normal bake for auto finishes at 121° C.; and low bake repair at 82° C.) as measured by hardness, adhesion, solvent resistance and humidity resistance; the enamel should not yellow on curing and further color change on exposure to light should be minimized; the stabilizers should be soluble in the organic solvents normally used in coating applications, such as methyl amyl ketone, xylene, n-hexyl acetate, alcohol and the like.

The instant hindered amine light stabilizers on the N-atom by an O-substituted moiety containing a free hydroxyl group fulfill each of these requirements and provide alone or in combination with a UV absorber outstanding light stabilization protection to the cured acid catalyzed thermoset enamels.

The instant invention also pertains to resin systems capable of being fully cured under ambient conditions. For example, applicable resins include alkyd, acrylic, polyester and epoxide resins as described in S. Paul's "Surface Coatings: Science and Technology" (1985), pages 70–310. Various acrylic and modified acrylic resins are described in H. Kittel's "Lehrbuch der Lacke unde Beschichtungen", Vol. 1, Part 2, on pages 735 and 742 (Berlin 1972), and in "Lack-kunstharze" (1977) by H. Wagner and H. F. Sarx, op. cit, on pages 229–238. Typical crosslinkable polyester resins which can be stabilized against the action of light and moisture are described e.g. in H. Wagner and H. F. Sarx, op. cit., on pages 86–99. The unmodified and modified alkyd resins which can be stabilized are conventional resins which are used in trade sales, maintenance and automotive refinish coatings. For example, such coatings are based on alkyd resins, alkyd/acrylic resins and alkyd/silicon reins (see H. Wagner and H. F. Sarx, op. cit., pages 99–123) optionally crosslinked by isocyanates or epoxy resins.

In addition various acrylic lacquer coating compositions are disclosed in U.S. Pat. No. 4,162,249. Other acrylic/alkyd resins with polyisocyanate additives are disclosed in U.S. Pat. No. 4,471,083; and acrylic resins containing either pendant amino ester groups or glycidyl groups are described in U.S. Pat. No. 4,525,521.

The ambient cured coatings stabilized by the instant compounds are suitable both for metal finish coatings and solid shade finishes, especially in the case of retouching finishes. The lacquers stabilized by the instant compounds are preferably applied in a conventional manner by two methods, either by the single-coat method or by the two-coat method. In the latter method, the pigment-containing base coat is applied first and a covering coat of clear lacquer applied over it. When used in two-coat finishes, the instant hindered amine compound can be incorporated in the clear coat or both in the clear coat and in the pigmented base coat.

The instant invention also pertains to abrasion-resistant coating compositions suitable for coating over polycarbonates. Such coatings as described in U.S. Pat. No. 5,214,085 comprise a silyl acrylate, aqueous colloidal silica, a photo-initiator and optionally a polyfunctional acrylate as well as UV absorbers. Such coatings provide resistance after prolonged outdoor exposure to sunlight, moisture, thermal cycling causing yellowing, delamination and formation of microcracks and decreasing transparency.

Related hindered amine stabilizers have been utilized individually and in combination with UV absorbers to improve the performance characteristics of ambient cured coating systems. Notwithstanding such improvements, there still exists a need to further retard the photooxidation and photodegradation of such ambient cured systems and thereby provide increased effectiveness by maintaining the physical integrity of the coatings. Such effectiveness can be manifested by prevention of embrittlement, cracking, corrosion, erosion, loss of gloss, chalking and yellowing of the coating.

It has now been determined that the aforementioned improvements can be achieved by substitution of the N-atom of the hindered amines with an -OR moiety and by the utilization of such derivatives in ambient cured coating systems as is taught in U.S. Pat. No. 5,124,378, the relevant parts of which are incorporated herein by reference. The instant compounds are even less basic than the compounds of U.S. Pat. No. 5,124,378 and are particularly well suited for this task. In particular, the physical integrity of the coatings is maintained to a higher degree with significant reduction in loss of gloss and in yellowing. Accordingly, the instant invention relates to the use of the instant NOR compounds, where the R moiety is further substituted by a hydroxyl group, optionally together with further stabilizers, for stabilizing ambient cured coatings based on alkyd resins; thermoset acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

The instant invention also relates to electrodeposited coatings applied to metal substrates where various top coats may be applied thereover. The inclusion of the instant compounds in the E-coat provides delamination resistance to said E-coats. The primary resins in said E-coats are acrylic or epoxy resins. These E-coats are described in European patent application EP 0 576 943 A1.

The instant invention also pertains to UV-cured coating systems using unsaturated acrylic resins, polyurethane acrylates, epoxy acrylates, polyester acrylates, unsaturated polyester/styrene resins and silyl acrylates.

Synthesis of Compounds

The instant compounds may be prepared by the reaction of tributyltin hydride and a halogen substituted alcohol to produce carbon centered radicals that are trapped by nitroxyl compounds.

The instant compounds may also be prepared by coupling an N-oxyl hindered amine with a carbon centered radical generated by the photochemical or thermal decomposition of a perester or dialkyl peroxide in the presence of an alcohol. The bridge compounds described above can be formed when two nitroxyl radicals couple with the same solvent molecule, especially when the amount of solvent is reduced.

The preferred method of preparation of the instant compounds is to react an N-oxyl hindered amine with a carbon centered radical generated by mixing an aqueous or alcoholic solution. of a metal ion such as $Fe^{2+}$, $Fe^{3+}$, $Cu^{2+}$ or $Cu^{+}$ and a peroxide such as tert-butyl hydroperoxide or hydrogen peroxide in the presence of an alcohol solvent at a temperature of 20–80° C. Especially effective is the combination of ferrous chloride, ferric chloride or ferrous sulfate, particularly ferrous chloride, or ferric chloride, and hydrogen peroxide. Water may be added to the alcohol at the beginning of the reaction to improve solubility of the metal salt or to dissolve an alcohol which is solid at the reaction temperature. A ligand such as 2,2'-dipyridyl, 2,2':6',2''-terpyridyl, may be added to the reaction mixture. Two nitroxyl radicals can sometimes couple with the same solvent molecule to produce bridged compoundsdescribed in some formulas listed earlier. The formation of bridge compounds is more favored when the amount of solvent is reduced.

Some of the instant hydroxy-substituted N-alkoxy compounds may be reacted with monofunctional or difunctional esters, acids or acid chlorides or isocyanates to form polymeric ester or urethane derivatives.

The following examples are for illustrative purposes only and are not to be construed to limit the instant invention in any manner whatsoever.

EXAMPLE 1

Reaction of 1-Oxyl-2,2,6,6-tetramethylpiperidin-4-one with Cyclohexanol

A solution of 55 g (0.49 mol) of 30% aqueous hydrogen peroxide is added dropwise over a 4.25 hour period to a mixture of 23.5 g (0.14 mol) of 1-oxyl-2,2,6,6-tetramethylpiperidin-4-one and 4.0 g (0.020 mol) of ferrous chloride tetrahydrate in 14 g (0.14 mol) of cyclohexanol and 150 g of cyclohexane. The reaction temperature is maintained at approximately 40° C. throughout the addition. The reaction mixture is stirred at 40° C. for three hours after the peroxide addition is complete. A second portion of 30% aqueous hydrogen peroxide (10 g, 0.09 mol) is added and the reaction mixture is heated at 40° C. for seven hours. After the mixture is cooled to room temperature, sodium sulfite (5 g) is added. The reaction temperature is carefully brought to 60° C. for one hour to decompose excess peroxide. Upon cooling, the organic layer is separated, dried over anhydrous magnesium sulfate, and concentrated to give 22.6 g of a brown oil. The oil is dissolved in cyclohexane and passed through silica gel with cyclohexane and then 1:2 (v/v) ethanol/cyclohexane to afford 16.5 g of a yellow oil.

Analysis by gass chromatography and mass spectrometry shows the product to be a mixture which contains at least four isomers of 1-(hydroxycyclohexyloxy)-2,2,6,6-tetramethylpiperidin-4-one.

EXAMPLE 2

Bis[-(2-hydroxy-2-methylpropoxy)-2,2,6,6-tetramethylpiperidin-4-yl)]Sebacate

A solution of 73 g (0.64 mol) of 30% aqueous hydrogen peroxide is added dropwise over a 3.5 hour period to a mixture of 30.0 g (0.059 mol) of bis(1-oxyl-2,2,6,6-tetramethylpiperidin-yl)sebacate and 4.7 g (0.024 mol) of ferrous chloride tetrahydrate in 150 g of tert-butyl alcohol and 6 g of water. The reaction temperature is kept at approximately 40° C. throughout the peroxide addition. The reaction mixture is stirred at 40° C. for four hours after the addition is complete. The reaction mixture is diluted with 150 g of ethyl acetate. A colution of 100 g of 20% aqueous sodium sulfite solution is added and the reaction mixture is stirred for 1.5 hours at 45–60° C. to decompose excess peroxide. The aqueous layer is extracted with 100 g of ethyl acetate, and the combined organic layers are washed with 200 g of 5% sulfuric acid. Solvent is evaporated to obtain 39.4 g of a pale yellow liquid which is purified by flash chromatography on silica gel with a 4:1:5 part mixture (by volume) of ethyl acetate:isopropanol:hexane to afford 19.1 g (49% yield) of the title compound as a pale yellow oil.

$^1$Hnmr (CDCl$_3$): δ=3.65 ppm (4H, —NOCH$_2$—)

EXAMPLE 3

Reaction of Bis(1-oxyl-2,2,6,6-tetramethylpiperidin-4-yl)Sebacate with Cyclohexanol A solution of 70 g (0.62 mol) of 30% aqueous hydrogen peroxide is added dropwise over 2.75 hours to a mixture of 32.4 g (0.063 mol) of bis(1-oxyl-2,2,6,6-tetramethylpiperidin-yl)sebacate and 5.0 g (0.025 mol) of ferrrous chloride tetrahydrate in 100 g of cyclohexanol. The reaction temperature is maintained at 40–45° C. during the addition. The reaction mixture is then stirred at 40° C. for five hours and during this time, fresh 50% aqueous hydrogen peroxide (5.0 g, 0.074 mol) is added to the reaction mixture in two equal portions. The following day, the reaction mixture is heated to 40° C., another portion of 50% aqueous hydrogen peroxide (2.5 g, 0.037 mol) is added, and the mixture is maintained at 40° C. for another five hours. A solution of 100 g of 20% aqueous sodium sulfite is added to the mixture and the reaction temperature is maintained at 70° C. for 45 minutes to decompose excess hydrogen peroxide. The combined organic layers are concentrated to give 151 g of crude product. Water is added, and residual cyclohexanol is removed by steam distillation. The remaining 50 g of crude product is purified by flash chromatography on silica gel with a 10:1:10 part mixture of ethyl acetate:ethanol:hexane to afford 32.9 g of an oil. NMR analysis shows that the oil contains bis[1-(trans-2-hydroxycyclohexyloxy)-2,2,6,6-tetramethylpiperidin-4-yl] sebacate in addition to other structural isomers of said sebacate compound.

EXAMPLE 4

Reaction of 4-Hydroxy-1-oxyl-2,2,6,6-tetramethylpiperidine with Cyclohexanol

A solution of 50 g (0.74 mol) of 50% aqueous hydrogen peroxide is added dropwise over a 1.75 hour period to a mixture of 35.0 g (0.20 mol) of 4-hydroxy-1-oxyl-2,2,6,6-tetramethylpiperidine and 10.0 gr (0.050 mol) of ferrous chloride tetrahydrate in 100 g of cyclohexanol. The reaction temperature is maintained at approximately 40–45° C. throughout the addition. After the peroxide addition is complete, the reaction mixture is stirred at 40° C. for five hours. The mixture is cooled to room temperature and a solution of 100 g of 20% aqueous sodium sulfite is added. The reaction mixture is carefully heated at 60° C. for one hour to decompose excess peroxide. After acetone is added to the organic layer, the crude product mixture is filtered to remove solids and the filtrate is concentrated. Water is added and residual cyclohexanol is removed by steam distillation. The crude product is purified by flash chromatography on silica gel with 2:1 (v/v) hexane/ethyl acetate to afford 36.3 g of a yellow oil.

Analysis by mass spectrometry shows the oil to be a mixture of isomers of 1-(hydroxycyclohexyloxy)-4-hydroxy-2,2,6,6-tetramethylpiperidine and 1-(dihydroxycyclohexyloxy)-4-hydroxy-2,2,6,6-tetramethylpiperidine.

EXAMPLE 5

Reaction of 2,4-Bis[N-(1-oxyl-2,2,6,6-tetramethylpiperidin-4-yl)butylamino-6-chloro-s-triazine with Cyclohexanol A solution of 30 g (0.44 mol) of 50% aqueous hydrogen peroxide is added over a 2 hour period to a mixture of 39.4 g (0.070 mol) of 2,4-bis[N-(1-oxyl-2,2,6,6-tetramethylpiperidin-4-yl)butylamino-6-chloro-s-triazine and 7.0 g (0.035 mol) of ferrous chloride tetrahydrate in 150 g of cyclohexanol at a temperature of 40–45° C. The reaction mixture is stirred at 40° C. for ten hours after the peroxide addition is complete, and during this time, another 19 g (0.28 mol) portion of 50% aqeuous hydrogen peroxide is added. Another portion of 50% aqueous hydrogen peroxide (25 g, 0.37 mol) is added while the reaction mixture is heated at 50–65° C. for four hours. The reaction mixture is treated with a solution of 100 9 of 20% aqueous sodium sulfite at 60° C. for one hour to decompose residual peroxide. The organic layer is concentrated to a brown oil which is extracted thrice with cyclohexane and once with ethyl acetate. The combined extracts are concentrated to afford 43.4 g of a yellow solid.

EXAMPLE 6

2,4-Bis{N-[1-(trans-2-hydroxycyclohexyloxy)-2,2,6,6-tetramethylpiperidin-4-yl]butylamino}-6-(2-hydroxyethyl)amino-s-triazine The product obtained in Example 5 is reacted with ethanolamine and sodium hydroxide solution. The crude reaction mixture is duluted with ethyl acetate and washed with water. The aqueous layer is extracted with ethyl acetate, and the combined organic layers are concentrated. The residue is dissolved in ethyl acetate and cyclohexane is added. A brown oil is removed. The remaining solution is concentrated to give 13.7 g of crude product. The crude product is purified by flash chromatography on silica gel with 2:1 (v/v) ethyl acetate/hexane and then 8:1 (v/v) ethyl acetate/methanol to afford 6.4 g of a yellow oil. The oil is dissolved in ethanol and treated with decolorizing carbon at 60° C. for one hour. Solids are removed by filtration and the solvent is evaporated to give 6.5 g of an off-white solid, melting at 67–80° C.

NMR analysis shows the solid contains the title compound in addition to a mixture of hydroxycyclohexyloxy and dihydroxycyclohexyloxy structural isomers.

EXAMPLE 7

Bis[1-(2-hydroxy-2-methylpropoxy)-2,2,6,6-tetramethylpiperidin-4-yl]Adipate

Aqueous hydrogen peroxide is added to a mixture of bis(1-oxyl-2,2,6,6-tetramethylpieridin-4-yl)adipate and ferrous chloride tetrahydrate in tert-butyl alcohol at 30–50° C. Excess peroxide is decomposed with aqeuous sodium sulfite solution. The organic layer is concentrated and the crude product is purified by flash chromatography on silica gel to afford the title compound.

EXAMPLE 8

Bis[1-(2-hydroxy-2-methylpropoxy)-2,2,6,6-tetramethylpiperidin-4-yl]Glutarate

Aqueous hydrogen peroxide is added to a mixture of bis(1-oxyl-2,2,6,6-tetramethylpieridin-4-yl)glutarate and ferrous chloride tetrahydrate in tert-butyl alcohol at 30–50° C. Excess peroxide is decomposed with aqeuous sodium sulfite solution. The organic layer is concentrated and the crude product is purified by flash chromatography on silica gel to afford the title compound.

EXAMPLE 9

Bis[1-(2-hydroxy-2-methylpropoxy)-2,2,6,6-tetramethylpiperidin-4-yl]Succinate

Aqueous hydrogen peroxide is added to a mixture of bis(1-oxyl-2,2,6,6-tetramethylpieridin-4-yl)succinate and ferrous chloride tetrahydrate in tert-butyl alcohol at 30–50° C. Excess peroxide is decomposed with aqeuous sodium sulfite solution. The organic layer is concentrated and the crude product is purified by flash chromatography on silica gel to afford the title compound.

EXAMPLE 10

Bis[1-(2-hydroxy-1-phenethoxy)-2,2,6,6-tetramethylpiperidin-4-yl]Sebacate

Aqueous hydrogen peroxide is added to a mixture of bis(1-oxyl-2,2,6,6-tetramethylpieridin-4-yl)sebacate and ferrous chloride tetrahydrate in phenethyl alcohol at 30–50° C. Excess peroxide is decomposed with aqeuous sodium sulfite solution. The organic layer is concentrated and the crude product is purified by flash chromatography on silica gel to afford the title compound.

EXAMPLE 11

2,4-Bis{N-[1-(2-hydroxy-2-methylpropoxy)-2,2,6,6-tetramethylpiperidin-4-yl]butylamino}-6-chloro-s-triazine A total of 40 g (0.59 mol) of 50% aqueous hydrogen peroxide is added in two portions over five hours to a mixture of 43.2 g (0.076 mol) of 2,4-bis[N-(1-oxyl-2,2,6,6-tetramethylpiperidin-4-yl)butylamino-6-chloro-s-triazine and 7.0 g (0.035 mol) of ferrous chloride tetrahydrate in 150 g of tert-butyl alcohol and 15 g of water. Another portion of 50% aqueous hydrogen peroxide (3 g, 0.044 mol) is added to the reaction mixture while the temperature is maintained at 40–45° C. for 2.25 hours. The reaction mixture is diluted with 100 g of ethyl acetate. A solution of 100 g of 20% aqueous sodium sulfite is added and the reaction mixture is heated at 60° C. for one hour to decompose residual peroxide. The aqueous layer is extracted with ethyl acetate, and the combined organic layers are concentrated. The crude product is purified by flash chromatography on silica gel with 1:1 (v/v) hexane/ethyl acetate to afford 54.1 g of the title compound.

EXAMPLE 12

2,4-Bis{N-[1-(2-hydroxy-2-methylpropoxy)-2,2,6,6-tetramethylpiperidin-4-yl]butylamino}-6-(2-hydroxyethyl)amino-s-triazine The title compound is prepared by the reaction of the intermediate prepared in Example 11 with ethanolamine and sodium hydroxide. The aqueous layer is removed, and the remaining layer is extracted with cyclohexane. Solvent is evaporated at reduced pressure, and the crude product is purified by flash chromatography on silica gel with 1:2 (v/v) hexane/ethyl acetate to afford 4.1 g of the title compound as a white solid, melting at 110–120° C.

$^1$Hnmr (CDCl$_3$): δ=3.54 ppm (q,2H, NCH$_2$); 3.59 ppm (s,4H, NOCH$_2$).

EXAMPLE 13

Reaction of the Product of Example 11 with N,N'-Bis(3-aminopropyl)Ethylenediamine The product prepared in Example 11 is reacted with N,N'-bis(3-aminopropyl)ethylenediamine in a 3:1 molar ratio. The product mixture includes N,N',N"-tris{2,4-bis[N-[1-(2-hydroxy-2-methylpropoxy)-2,2,6,6-tetramethylpiperidin-4-yl]butylamino]-s-triazin-6-yl}-3,3'-ethylenediiminodipropylamine and N,N',N'''-tris{2,4-bis[N-[1-(2-hydroxy-2-methylpropoxy)-2,2,6,6-tetramethylpiperidin-4-yl]butylamino]-s-triazin-6-yl}-3,3'-ethylenediiminodipropylamine.

EXAMPLE 14

2,4-Bis{N-[1-(2-hydroxy-2-methylpropoxy)-2,2,6,6-tetramethylpiperidin-4-yl]butylamino}-6-octylamino-s-triazine The reaction of the compound prepared in Example 11 with excess octylamine yields the title compound as an off-white glass melting at 68–86° C.

EXAMPLE 15

N,N'-Bis{4,6bis{N-[1-(2-hydroxy-2-methylpropoxy)-2,2,6,6-tetramethylpiperidin-4-yl]butylamino}-s-triazin-2-yl}-1,6-diaminohexane The title compound is prepared by the reaction of the compound prepared in Example 11 with hexamethylenediamine.

EXAMPLE 16A

Reaction of 4Hydroxy-1-oxyl-2,2,6,6-tetramethylpiperidine with tert-Butyl Alcohol A solution of 50% aqueous hydrogen peroxide is added to a mixture of 4-hydroxy-1-oxyl-2,2,6,6-tetramethylpiperidine and ferrous chloride tetrahydrate in tert-butyl alcohol at 30–60° C. Excess peroxide is decomposed with aqeuous sodium sulfite. The organic layer is concentrated and the crude product is purified by flash chromatography on silica gel to afford a sample of 4-hydroxy-1-(2-hydroxy-2-methylpropoxy)-2,2,6,6-tetramethylpiperidine.

EXAMPLE 16B 1-(2-Hydroxy-2-methylpropoxy)-2,2,6,6-tetramethylpiperidin-4-yl Methacrylate The title compound is prepared by reaction of the compound prepared in Example 16A with methyl methacrylate.

EXAMPLE 17

4-Allyloxy-1-(2-hydroxy-2-methylpropoxy)-2,2,6,6-tetramethylpiperidine

The title compound is prepared by the reaction of the compound prepared in Example 16A with allyl bromide.

EXAMPLE 18

4-(2,3-Epoxypropoxy-1-(2-hydroxy-2-methylpropoxy)-2,2,6,6-tetramethylpiperidine

The title compound is prepared by the reaction of the compound prepared in Example 16A with epichlorohydrin.

EXAMPLE 19

1-(2-Hydroxy-2-methylpropoxy)-2,2,6,6-tetramethylpiperidin-4-yl 3-{[[[1-(2-hydroxy-2-methylpropoxy)-2,2,6,6-tetramethylpiperidin-4-yloxy]carbonyl]-amino]methyl}-3,5,5-trimethylcyclohexylcarbamate The title compound is prepared by the reaction of the compound prepared in Example 16A with 5-isocyanato-1-(isocyanatomethyl)-1,3,3-trimethylcyclohexane (=isophorone diisocyanate).

EXAMPLE 20

Bis[1-(2-hydroxy-2-methylpropoxy)-2,2,6,6-tetramethylpiperidin-4-yl]1,6-Hexanedicarbamate The title compound is prepared by the reaction of the compound prepared in Example 16A with hexamethylene diisocyanate.

EXAMPLE 21

1-(2-Hydroxy-2-methylpropoxy)-2,2,6,6-tetramethylpiperidin-4-yl Acrylate

The title compound is prepared by the reaction of the compound prepared in Example 16A with methyl acrylate.

EXAMPLE 22

2,4,6-Tris{N-[1-(2-hydroxy-2-methylpropoxy)-2,2,6,6-tetramethylpiperidin-4-yl]butylamino}-s-triazine A solution of 40 g (0.35 mol) of 30% aqueous hydrogen peroxide is added over 1.25 hours to a mixture of 11.7 g (0.011 mol) of 2,4,6-tris[N-(1-oxyl-2,2,6,6-tetramethylpiperidin-4-yl]butylamino}-s-triazine and 3.0 g (0.015 mol) of ferrous chloride tetrahydrate in 100 g of tert-butyl alcohol and 9 g of water. The reaction temperature is maintained at 60–65° C. during the peroxide addition. Two equal portions (2 g, 0.29 mol) of 50% aqueous hydrogen peroxide are added to the reaction mixture while the temperature is maintained at 60° C. for 9.5 hours. After the reaction mixture is diluted with ethyl acetate and cooled to room temperature, a solution of 100 g of 20% aqueous sodium sulfite is added. The reaction mixture is heated at 60° C. for one hour to decompose the excess peroxide. The aqueous layer is extracted with ethyl acetate, and the combined organic layers are concentrated. The crude product is purified by flash chromatography on silica gel with 2:1 (v/v) cyclohexane/ethyl acetate to afford a material which is triturated with 1:1 (v/v) cyclohexane/acetone to give 4.0 g of the title compound as a white solid, melting at 172–176° C.

EXAMPLE 23A

Reaction of 1-Oxyl-2,2,6,6-tetramethylpiperidin-4-one with tert-Butyl Alcohol

Aqueous hydrogen peroxide is added to a mixture of 1-oxyl-2,2,6,6-tetramethylpiperidin-4-one and ferrous chloride in tert-butyl alcohol at 30–60° C. Excess peroxide is decomposed with aqueous sodium sulfite. The organic layer is concentrated and the residue is purified by flash chromatography to afford the desired 1-(2-hydroxy-2-methylpropoxy)-2,2,6,6-tetramethylpiperidin-4-one.

EXAMPLE 23B

4-Butylamino-1-(2-hydroxy-2-methylpropoxy)-2,2,6,6-tetramethylpiperidine

A mixture of butylamine, the compound prepared in Example 23A and a catalytic amount of 5% platinum on carbon is hydrogenated at 3 atmospheres using a Parr apparatus. The catalyst is removed by filtration, and the solvent is evaporated to afford the title compound.

EXAMPLE 24

4-Trimethylsilyloxy-1-(2-hydroxy-2-methylpropoxy)-2,2,6,6-tetramethylpiperidine

The title compound is prepared by the reaction of the compound prepared in Example 16A with chlorotrimethylsilane.

EXAMPLE 25

4-Benzoyloxy-1-(2-hydroxy-2-methylpropoxy)-2,2,6,6-tetramethylpiperidine

A solution of 50% aqueous hydrogen peroxide is added slowly to a mixture of 4-benzoyloxy-1-oxyl-2,2,6,6-tetramethylpiperidine and ferrous chloride tetrahydrate in tert-butyl alcohol at 30–60° C. Excess peroxide is decomposed by aqueous sodium sulfite solution. The organic layer is concentrated and the residue is purified by flash chromatography to afford the title compound.

EXAMPLE 26

1-(2-Hydroxy-2-methylpropoxy)-4-[3-(trimethylsilyl)propoxy]-2,2,6,6-tetramethylpiperidine The title compound is prepared by reacting the compound prepared in Example 17 with trimethylsilane and hydrogen hexachloroplatinate(IV) in isopropyl alcohol.

EXAMPLE 27

Tetrakis{3-[1-(2-hydroxy-2-methylpropoxy)-2,2,6,6-tetramethylpiperidin-4-yloxy]propyl}-1,3,5,7-tetramethylcyclotetrasiloxane The title compound is prepared by the reaction of the compound prepared in Example 17 with 1,3,5,7-tetramethylcyclotetrasiloxane, hydrogen hexachloroplatinate(IV) in isopropyl alcohol.

EXAMPLE 28

Poly{[3-[1-(2-hydroxy-2-methylpropoxy)-2,2,6,6-tetramethylpiperidin-4-yloxy]propyl]methyl}silane The title compound is prepared by the reaction of the compound prepared in Example 17 with poly(methylsilane) and hydrogen hexachloroplatinate(IV) in isopropyl alcohol.

EXAMPLE 29

Poly}[3-[1-(2-hydroxy-2-methylpropoxy)-2,2,6,6-tetramethylpiperidin-4-yloxy]propyl]methyl}siloxane The title compound is prepared by the reaction of the compound prepared in Example 17 with poly (methylsiloxane) and hydrogen hexachloroplatinate(IV) in isopropyl alcohol.

EXAMPLE 30

Mixture of Bis[1-(2-Hydroxy-2-methylpropoxy)-2,2,6,6-tetramethylpiperidin-4-yl]Glutarate and Bis[1-(2-Hydroxy-2-methylpropoxy)-2,2,6,6-tetramethylpiperidin-4-yl]Adipate A mixture of the compound prepared in Example 16A, DBE-2 dimethyl ester mixture (DuPont), and lithium amide is heated at reflux in xylene. Methanol is distilled from the reaction mixture. The reaction mixture is quenched with dilute mineral acid, and the organic layer is washed with water and dried over anhydrous magnesium sulfate. The xylene solution is evaporated at reduced pressure to afford the title compound mixture.

EXAMPLE 30A

Mixture of Bis[1-(2-Hydroxy-2-methylpropoxy)-2,2,6,6-tetramethylpiperidin-4-yl]Glutarate and Bis[1-(2-Hydroxy-2-methylpropoxy)-2,2,6,6-tetramethylpiperidin-4-yl]Succinate When the procedure of Example 30 is repeated with DBE-9 a dimethyl ester mixture (DuPont), the title mixture is prepared.

EXAMPLE 31

Reaction of Bis(1-oxyl-2,2,6,6-tetramethylpiperidin-4-yl)Sebacate with Neopentyl Alcohol Aqueous hydrogen peroxide is added to a mixture of bis(1-oxyl-2,2,6,6-tetramethylpiperidin-4-yl)sebacate and ferrous chloride in neopentyl alcohol according to the procedure of Example 25.

EXAMPLE 32

Reaction of 1-oxyl-2,2,6,6-tetramethylpiperidin-4-one with Neopentyl Glycol

Aqueous hydrogen peroxide is added to a mixture of 1-oxyl-2,2,6,6-tetramethylpiperidin-4one and ferrous chloride in neopentyl glycol according to the procedure of Example 25.

EXAMPLE 33

Reaction of 4-Octadecanoyloxy-1-oxyl-2,2,6,6-piperidine with tert-Amyl Alcohol

Aqueous hydrogen peroxide is added to a mixture of 4-octadecanoyloxy-1-oxyl-2,2,6,6-tetramethylpiperidine and ferrous chloride in tert-amyl alcohol according to the procedure of Example 25.

EXAMPLE 34

4-Benzoyloxy-1-(2-hydroxycyclohexyloxy)-2,2,6,6-tetramethylpiperidine

Tributyltin hydride is added dropwise to a solution of 2-bromocyclohexanol and excess 4-benzoyloxy-1-oxyl-2,2,6,6-tetramethylpiperidine in chlorobenzene. The mixture is heated to facilitate reaction. The crude reaction mixture is passed through silica gel with heptane and then heptanel-ethyl acetate to afford the title compound as a mixture os cis/trans isomers.

EXAMPLE 35

4-Hydroxy-1-(2-hydroxycyclohexyloxy)-2,2,6,6-tetramethylpiperidine

The title compound is prepared by heating the compound prepared in Example 34 in a solution of potassium hydroxide in methanol.

EXAMPLE 36

Reaction of 4-Benzoyloxy-1-oxyl-2,2,6,6-tetramethylpiperidine with Propylene Glycol Aqueous hydrogen peroxide is added to a mixture of 4-benzoyloxy-1-oxyl-2,2,6,6-tetramethylpiperidine and ferrous chloride tetrahydrate in propylene glycol according to the procedure of Example 25.

EXAMPLE 37

Reaction of 4-Benzoyloxy-1-oxyl-2,2,6,6-tetramethylpiperidine with Trimethylene Glycol Aqueous hydrogen peroxide is added to a mixture of 4-benzoyloxy-1-oxyl-2,2,6,6-tetramethylpiperidine and ferrous chloride tetrahydrate in trimethylene glycol according to the procedure of Example 25.

EXAMPLE 38

Bis[1-(2-hydroxyethoxy)-2,2,6,6-tetramethylpiperidin-4-yl]Sebacate

Tributyltin hydride is added dropwise to a solution of 2-iodoethanol and excess bis(1-oxyl-2,2,6,6-tetramethylpiperidin-4-yl)sebacate in chlorobenzene. The crude reaction mixture is passed through silica gel with heptane and then heptane/ethyl acetate to afford the title compound.

EXAMPLE 39

Reaction of Bis(1-oxyl-2,2,6,6-tetramethylpiperidin-4-yl)Sebacate with Isopropanol Aqueous hydrogen peroxide is added to a mixture of bis(1-oxyl-2,2,6,6-tetramethylpiperidin-4-yl)sebacate and ferrous chloride tetrahydrate in isopropanol according to the procedure of Example 25.

EXAMPLE 40

Reaction of 4-Benzoyloxy-1-oxyl-2,2,6,6-tetramethylpiperidine with 1,4-Butanediol Aqueous hydrogen peroxide is added to a mixture of 4-benzoyloxy-1-oxyl-2,2,6,6-tetramethylpiperidine and ferrous chloride tetrahydrate in 1,4-butanediol according to the procedure of Example 25.

EXAMPLE 41

Reaction of 4-Hexyloxy-1-oxyl-2,2,6,6-tetramethylpiperidine with Pinacol

Aqueous hydrogen peroxide is added to a mixture of 4-hexyloxy-1-oxyl-2,2,6,6-tetramethylpiperidine and ferrous chloride tetrahydrate in pinacol according to the procedure of Example 25.

EXAMPLE 42

Reaction of 1-Oxyl-2,2,6,6-tetramethylpiperidin-4-one with Glycerol

Aqueous hydrogen peroxide is added to a mixture of 1-oxyl-2,2,6,6-tetramethylpiperidin-4-one and ferrous chloride tetrahydrate in glycerol according to the procedure of Example 25.

EXAMPLE 43

Reaction of 4-Hydroxy-1-oxyl-2,2,6,6-tetramethylpiperidine with 2-Ethyl-1-hexanol Aqueous hydrogen peroxide is added to a mixture of 4-hydroxy-1-oxyl-2,2,6,6-tetramethylpiperidine and ferrous chloride tetrahydrate in 2-ethyl-1-hexanol according to the procedure of Example 25.

EXAMPLE 44

1-(2-Hydroxy-2-methylpropoxy)-4-hexadecanoyloxy-2,2,6,6-tetramethylpiperidine

A mixture of the compound prepared in Example 16A, methyl hexadecanoate and lithium amide is heated at reflux in xylene, Methanol is distilled from the reaction mixture. The reaction mixture is quenched with dilute mineral acid, and the organic layer is washed with water and dried over anhydrous magnesium sulfate. The xylene solution is evaporated at reduced pressure to afford the title compound.

EXAMPLE 44A 1-(4-Hexadecanoyloxy-2,2,6,6-tetramethylpiperidin-1-yloxy)-2-hexadecanoyloxy-2-methylpropane The title compound is prepared by the reaction of the compound prepared in Example 16A with excess methyl hexadecanoate and a catalytic amount of lithium amide in xylene.

EXAMPLE 45

Reaction of N,N',N'',N'''-Tetrakis{2,4-bis[N-(1-oxyl-2,2,6,6-tetramethylpiperidin-4-yl]butylamino]-s-triazin-6-yl}-3,3'-ethylenediiminodipropylamine with Cyclohexanol A mixture of N,N',N'',N'''-tetrakis{2,4-bis[N-(1-oxyl-2,2,6,6-tetramethylpiperidin-4-yl]butylamino]-s-triazin-6-y}3,3'-ethylenediiminodipropylamine in cycdohexanol is reacted with aqueous hydrogen peroxide and ferrous chloride tetrahydrate according to the method of Example 4. A white solid melting at 133–175° C. is obtained.

EXAMPLE 46

Reaction of 2,4,6-Tris[N-(1-oxyl-2,2,6,6-tetramethylpiperidin-4-yl]butylamino}-s-triazine with Cyclohexanol A mixture of 2,4,6-tris[N-(1-oxyl-2,2,6,6-tetramethylpiperidin-4-yl]butylamino}-s-triazine and cyclohexanol is reacted with aqueous hydrogen peroxide and ferrous chloride tetrahydrate according to the procedure of Example 4. A light brown oil is obtained.

EXAMPLE 47

Bis[1-(3-hydroxypropoxy)-2,2,6,6-tetramethylpiperidin-4-yl]Sebacate

Tributyltin hydride is added dropwise to a solution of 3-bromo-1-propanol and excess bis(1-oxyl-2,2,6,6-tetramethylpiperidin-4-yl)sebacate in chlorobenzene. The mixture is heated to facilitate reaction. The crude reaction mixture is passed through silica gel with heptane and then heptane/ethyl acetate to afford the title compound.

EXAMPLE 48

Bis[1-(12-hydroxy-1-dodecyloxy)-2,2,6,6-tetramethylpiperidin-4-yl]Sebacate

Tributyltin hydride is added dropwise to a solution of 12-bromo-1-dodecanol and excess bis(1-oxyl-2,2,6,6-tetramethylpiperidin-4-yl)sebacate in chlorobenzene. The mixture is heated to facilitate reaction. The crude reaction mixture is passed through silica gel with heptane and then heptane/ethyl acetate to afford the title compound.

EXAMPLE 49

Bis[1-(2-hydroxypropoxy)-2,2,6,6-tetramethylpiperidin-4-yl]Sebacate

Tributyltin hydride is added dropwise to a solution of 1-bromo-2-propanol and excess bis(1-oxyl-2,2,6,6-tetramethylpiperidin-4-yl)sebacate in chlorobenzene. The mixture is heated to facilitate reaction. The crude reaction mixture is passed through silica gel with heptane and then heptane/ethyl acetate to afford the title compound.

EXAMPLE 50

Reaction of the Product of Example 11 with N,N'-Bis(3-aminopropyl)Ethylenediamine N,N'-Bis(3-aminopropyl)ethylenediamine and the product prepared in Example 11 are reacted in a 1:3.0 to 1:3.5 molar ratio. The product mixture includes N,N',N''-tris{2,4-bis[N-[1-(2-hydroxy-2-methylpropoxy)-2,2,6,6-tetramethylpipeddin4-yl]butylamino]-s-triazin-6-yl}-3,3'-ethylenediiminodipropylamine, N,N',N'''-tris{2,4-bis[N-[1-(2-hydroxy-2-methylpropoxy)-2,2,6,6-tetramethylpipeddin-4-yl]butylamino]-s-triazin-6-yl}-3,3'-ethylenediiminodipropylamine, and N,N',N'',N'''-tetrakis{2,4-bis[N-[1-(2-hydroxy-2-methylpropoxy)-2,2,6,6-tetramethylpiperidin-4-yl]butylamino]-s-triazin-6-yl}-3,3'-ethylenediiminodipropylamine.

EXAMPLE 51

N,N',N'',N'''-Tetrakis{2,4-bis[N-[1-(2-hydroxy-2-methylpropoxy)-2,2,6,6-tetramethylpiperidin-4-yl]butylamino]-s-triazin-6-yl}-3,3'-ethylenediiminodipropylamine The title compound is prepared by the addition of aqueous hydrogen peroxide to a mixture of N,N',N'',N'''-tetrakis{2,4-bis[N-(1-oxyl-2,2,6,6-tetramethylpiperidin-4-yl]butylamino]-s-triazin-6-yl}-3,3'-ethylenediiminodipropylamine, ferrous chloride and tert-butyl alcohol according to the procedure of Example 7.

EXAMPLE 52

Reaction of the Product of Example 11 with N,N'-Bis(3-aminopropyl)Ethylenediamine N,N'-Bis(3-aminopropyl)ethylenediamine and the product prepared in Example 11 are reacted in a 1:4.0 molar ratio. The product mixture includes N,N',N''-tris{2,4-bis[N-[1-(2-hydroxy-2-methylpropoxy)-2,2,6,6-tetramethylpiperidin-4-yl]butylamino]-s-triazin-6-yl}-3,3'-ethylenediiminodipropylamine, N,N',N'''-tris{2,4-bis[N-[1-(2-hydroxy-2-methylpropoxy)-2,2,6,6-tetramethylpipeddin-4-yl]butylamino]-s-triazin-6-yl}-3,3'-ethyienediiminodipropylamine, and N,N',N'',N'''-tetrakis{2,4-bis[N-[1-(2-hydroxy-2-methylpropoxy)-2,2,6,6-tetramethylpiperidin-4-yl]butylamino]-s-triazin-6-yl}-3,3'-ethylenediiminodipropylamine.

EXAMPLE 53A

2-{N-[1-(2-Hydroxy-2-methylpropoxy)-2,2,6,6-tetramethylpiperidin-4-yl]butylamino}-4,6-dichloro-s-triazine The compound prepared in Example 23B is reacted with an equimolar amount of cyanuric chloride and sodium bicarbonate at 0° C. to give the title compound.

EXAMPLE 53B

N,N'-Bis[1-(2-hydroxy-2-methylpropoxy)-2,2,6,6-tetramethylpiperidin-4-yl]-1,6-hexanediamine The title compound is prepared by the hydrogenation at 50 psi of the compound obtained in Example 23A, hexamethylenediamine, methanol and a catalytic amount of 5% platinum on carbon.

EXAMPLE 53C

N,N'-Bis{2-[N-(2-hydroxy-2-methylpropoxy)-2,2,6,6-tetramethylpiperidin-4-yl]butylamino]-4-chloro-s-triazin-6-yl}-N,N'-bis[1-(2-hydroxy-2-methylpropoxy)-2,2,6,6-tetramethylpiperidin-4-yl]-1,6-hexanediamine The title compound is prepared by reaction of the two compounds prepared in Examples 53A and 53B in a 2:1 molar ratio in xylene at 60–80° C. with sodium hydroxide as the acid acceptor.

EXAMPLE 53D

Oligomer of N-{2-[N-[1-(2-hydroxy-2-methylpropoxy)-2,2,6,6-tetramethylpiperidin-4-yl]butylamino]-s-triazin-4-yl}-N,N'-bis[1-(2-hydroxy-2-methylpropoxy)-2,2,6,6-tetramethylpiperidin-4-yl]-1,6-hexanediamine Terminated with 2,4-bis(dibutylamino)-s-triazin-6-yl The compounds prepared in Examples 53B and 53C are mixed together in a 2:1 molar ratio in xylene solution at 100–160° C. with sodium hydroxide as the acid acceptor. The reaction mixture is then treated with 2,4-bis(dibutylamino)-6-chloro-s-triazine under the same conditions to give an oligomeric product having a low number (2, 4, 6, 8) of repeating units terminated by the 2,4-bis(dibutylamino)-s-triazin-6-yl moieties as seen in the structure below.

EXAMPLE 54

Oligomer of N-{2-[N-[1-(2-hydroxy-2-methylpropoxy)-2,2,6,6-tetramethylpipeddin-4-yl]butylamino]-s-triazin-4-yl}-N,N'-bis[1-(2-hydroxy-2-methylpropoxy)-2,2,6,6-tetramethylpiperidin-4-yl]-1,6-hexanediamine Terminated with 2,4-bis(dibutylamino)-s-triazin-6-yl N,N'-Bis(2,2,6,6-tetramethylpiperidin-4-yl)-1,6-hexanediamine and N,N'-bis{2-[N-(2,2,6,6-tetramethylpiperidin-4-yl)butylamino]-4-chloro-s-triazin-6-yl}-N,N'-bis(2,2,6,6-tetramethylpiperidin-4-yl)-1,6-hexanediamine are mixed together in a 2:1 molar ratio in xylene at 100–160° C. with sodium hydroxide as the acid acceptor. The reaction mixture is then treated with 2,4-bis(dibutylamino)-6-chloro-s-triazine under the same conditions. The resulting mixture of oligomers is heated with tert-butyl hydroperoxide and a catalytic amount of molybdenum trioxide in an inert solvent such as 1,2-dichloroethane to form the corresponding N-oxyl compounds. Aqueous hydrogen peroxide in then added to the mixture of the N-oxyl compounds and ferrous chloride tetrahydrate in tert-butyl alcohol according to the procedure of Example 7. The final products is a mixture of oligomers as in Example 53D although the ratios of the individual components may not be the same as in Example 53D.

EXAMPLE 55

Oligomer of N-{2-[N-[1-(2-hydroxy-2-methylpropoxy)-2,2,6,6-tetramethylpiperidin-4-yl]butylamino]-s-triazin-4-yl}-N,N'-bis[1-(2-hydroxy-2-methylpropoxy)-2,2,6,6-tetramethylpiperidin-4-yl]-1,6-hexanediamine Terminated with 2-butylamino-4-{N-[1-(2-hydroxy-2-methylpropoxy)-2,2,6,6-tetramethylpiperidin-4-yl]-butylamino-s-triazin-6-yl The title compound is prepared by heating a mixture of the compounds prepared in Examples 53A and 53B, in a

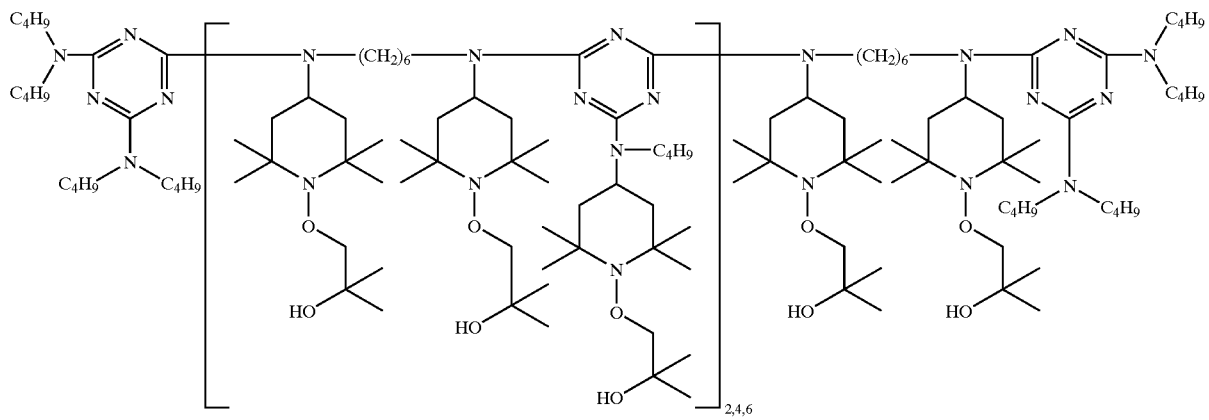

1.33 to 1.0 molar ratio in xylene at 100–160° C. using sodium hydroxide as the acid acceptor. Dibutylamine is then added to the reaction mixture under the same conditions to complete the reaction. The product is a mixture of oligomers that include 1–4 repeating units as seen in the structure below.

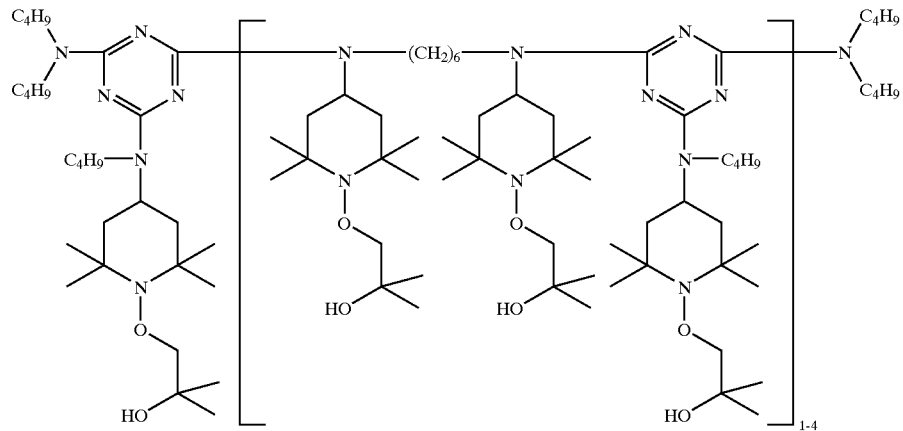

EXAMPLE 56

Oligomer of N-{2-[N-[1-(2-hydroxy-2-methylpropoxy)-2,2,6,6-tetramethylpiperidin-4-yl]butylamino]-s-triazin-4-yl}-N,N'-bis[1-(2-hydroxy-2-methylpropoxy)-2,2,6,6-tetramethylpiperidin-4-yl]-1,6-hexanediamine Terminated with 2-butylamino-4-{N-[1-(2-hydroxy-2-methylpropoxy)-2,2,6,6-tetramethylpiperidin-4-yl]-butylamino-s-triazin-6-yl The title compound is prepared by heating a mixture of the compounds prepared in Examples 53B and 53C, in a 0.5:1 molar ratio in xylene at 100–160° C. using sodium hydroxide as the acid acceptor. Dibutylamine is then added to the reaction mixture under the same conditions to complete the reaction. The product is a mixture of oligomers that include 1, 3, 5 and 7 repeating units as seen in the structure below.

EXAMPLE 57

Oligomer of N-{2-[N-[1-(2-Hydroxy-2-methylpropoxy)-2,2,6,6-tetramethylpiperidin-4-yl]butylamino]-s-triazin-4-yl}-N,N'-bis[1-(2-hydroxy-2-methylpropoxy)-2,2,6,6-tetramethylpiperidin-4-yl]-1,6-hexanediamine Terminated with 2-butylamino-4-{N-[1-(2-hydroxy-2-methylpropoxy)-2,2,6,6-tetramethylpiperidin-4-yl]-butylamino-s-triazin-6-yl N,N'-Bis(2,2,6,6-tetramethylpiperidin-4-yl)-1,6-hexanediamine and N,N'-bis{2-[N-(2,2,6,6-tetramethylpiperidin-4-yl)butylamino]-4-chloro-s-triazin-6-yl}-N,N'-bis(2,2,6,6-tetramethylpiperidin-4-yl)-1,6-hexanediamine are mixed together in a 0.5:1 molar ratio in xylene at 100–160° C. with sodium hydroxide as the acid acceptor. The reaction mixture is then treated with dibutylamine under the same conditions. The resulting mixture of

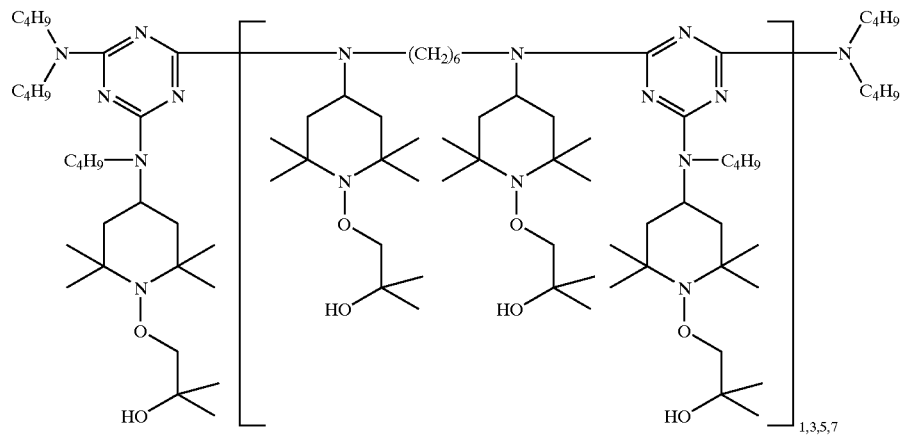

oligomers is treated with tert-butyl hydroperoxide and a catalytic amount of molybdenum trioxide in an inert solvent such as 1,2-dichloroethane to form the corresponding N-oxyl compounds. Aqueous hydrogen peroxide in then added to a mixture of the N-oxyl compounds and ferrous chloride tetrahydrate in tert-butyl alcohol according to the procedure of Example 7. The final product is a mixture of oligomers such as prepared in Example 56 although the

EXAMPLE 58

Oligomer of N-{2-[N-[1-(2-Hydroxy-2-methylpropoxy)-2,2,6,6-tetramethylpiperidin-4-yl]butylamino]-s-triazin-4-yl}-N,N'-bis[1-(2-hydroxy-2-methylpropoxy)-2,2,6,6-tetramethylpiperidin-4-yl]-1,6-hexanediamine Terminated with Acetyl The compounds prepared in Examples 53B and 53C are mixed together in a 2:1 molar ratio in xylene at 100–160° C. using sodium hydroxide as the acid acceptor. After the reaction is complete, the reaction mixture is concentrated at reduced pressure. Acetic anhydride is added to the reaction mixture at room temperature, and the mixture is then heated at 130° C. The crude mixture is cooled and neutralized with potassium carbonate. The reaction mixture is concentrated at reduced pressure. The product is a mixture of oligomers that include 2, 4, and 6 repeating units as seen in the structure below.

ratios of the individual components may not be the same as those in the product of Example 56.

EXAMPLE 59

Oligomer of N-{2-[N-[1-(2-hydroxy-2-methylpropoxy)-2,2,6,6-tetramethylpiperidin-4-yl]butylamino]-s-triazin-4-yl}-N,N'-bis[1-(2-hydroxy-2-methylpropoxy)-2,2,6,6-tetramethylpiperidin-4-yl]-1,6-hexanediamine Terminated with Acetyl Example 54 is repeated except that acetic anhydride is used in place of 2,4-bis(dibutylamino)-6-chloro-s-triazine according to the procedure of Example 58. The final product is a mixture of oligomers as described in Example 58 although the ratios of the components may not be identical to those of the product prepared in Example 58.

EXAMPLE 60

Poly[1-(2-hydroxy-2-methylpropoxy)-2,2,6,6-tetramethylpiperidin-4-yl Methacrylate The title compound is prepared from the free radical polymerization of the compound obtained in Example 16B. The average molecular weight of the polymer is 1500–3000 amu.

EXAMPLE 61

Poly[1-(2-hydroxy-2-methylpropoxy)-2,2,6,6-tetramethylpiperidin-4-yl Acrylate

The title compound is prepared from the free radical polymerization of the compound obtained in Example 21. The average molecular weight of the polymer is 1500–3000 amu.

EXAMPLE 62

1,4-Bis(4-hydroxy-2,2,6,6-tetramethylpiperidin-1-yloxy)-2-butanol

Tributyltin hydride is added dropwise to a solution of 1,4-dibromo-2-propanol and excess 4-hydroxy-1-oxyl-2,2,6,6-tetramethylpiperidine in chlorobenzene. The mixture is heated to facilitate the reaction. The crude reaction mixture is passed through silica gel with heptane and then heptane/ethyl acetate to afford the title compound.

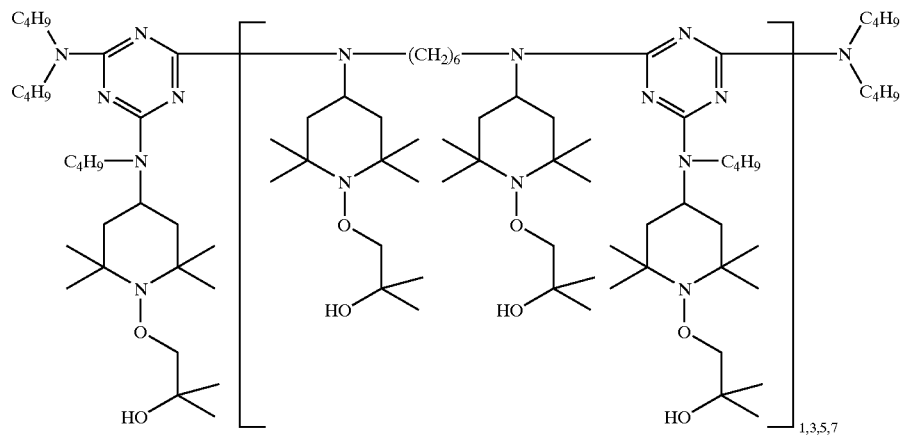

EXAMPLE 63

1,3-Bis(4-hydroxy-2,2,6,6-tetramethylpiperidin-1-yloxy)-2-propanol

Tributyltin hydride is added dropwise to a solution of 1,3dibromo-2-propanol and excess 4-hydroxy-1-oxyl-2,2,6,6-tetramethylpiperidine in chlorobenzene. The mixture is heated to facilitate the reaction. The crude reaction mixture is passed through silica gel with heptane and then heptanel-ethyl acetate to afford the title compound.

EXAMPLE 64

2-Hydroxy-2-methylpropane-1,3-diyl bis{[1-(2-hydroxy-2-methylpropoxy)-2,2,6,6-tetramethylpiperidin-4-yl](1-oxy-2,2,6,6-tetramethylpiperidin-4-yl)Sebacate The title compound is isolated by high pressure liquid chromatography from the crude reaction product obtained in Example 2.

EXAMPLE 65

1,3-Bis(4-octadecanoyloxy-2,2,6,6-tetramethyl piperidin-1-yloxy)-2-methyl-2-propanol Aqueous hydrogen peroxide is added to a mixture of 4-octadecanoyloxy-1-oxyl-2,2,6,6-tetramethylpiperidine and ferrous chloride tetrahydrate in tert-butyl alcohol at 30–50° C. Excess peroxide is decomposed with aqueous sodium sulfite solution. The organic layer is concentrated to obtain a mixture which includes 1-(2-hydroxy-2-methylpropoxy)-4-octadecanoyloxy-2,2,6,6-tetramethylpiperidine and the title compound. The title compound is separated from the mixture by high pressure liquid chromatography.

EXAMPLE 66

1,3-Bis(4-hydroxy-2,2,6,6-tetramethylpiperidin-1-yloxy)-2-methyl-2-propanol

The title compound is isolated by high pressure liquid chromatography from the crude reaction product obtained in Example 16A.

EXAMPLE 67

1,3-Bis(4-oxo-2,2,6,6-tetramethylpiperidin-1-yloxy)-2-methyl-2-propanol

The title compound is isolated by high pressure liquid chromatography from the crude reaction product obtained in Example 23A.

EXAMPLE 68

1-(2-Hydroxy-2-methylpropoxy)-2,2,6,6-tetramethylpiperidin-4-yl Hexanoate

The title compound is prepared by heating a mixture of methyl hexanoate, the compound prepared in Example 16A, lithium amide and xylene at reflux while methanol is removed by distillation.

EXAMPLE 69

4Benzoyloxy-1-(2-hydroxyethoxy)-2,2,6,6-tetramethylpiperidine

Tributyltin hydride is added dropwise to a solution of 2-iodoethanol and 4-benzoyloxy-1-oxyl-2,2,6,6-tetramethylpiperidine in chlorobenzene. The crude reaction mixture is passed through silica gel with heptane and then heptane/ethyl acetate to afford the title compound.

EXAMPLE 70

4-Hydroxy-1-(2-hydroxyethoxy)-2,2,6,6-tetramethylpiperidine

The title compound is prepared by heating a methanolic solution of the compound obtained in Example 69 with potassium hydroxide.

EXAMPLE 71

Poly[4-hydroxy-1-(2-hydroxyethoxy)-2,2,6,6-tetramethylpiperidin-4-yl Succinate]

The title compound is prepared by the reaction of approximately equimolar amounts of dimethyl succinate and the compound prepared in Example 70.

EXAMPLE 72

Poly[4-hydroxy-1-(2-hydroxycyclohexyloxy)-2,2,6,6-tetramethylpiperidin-4-yl Succinate]

The title compound is prepared by the reaction of approximately equimolar amounts of dimethyl succinate and the compound prepared in Example 35.

EXAMPLE 73

1-(2-Hydroxy-2-methylpropoxy)-4-octadecanoyloxy-2,2,6,6-tetramethylpiperidine

A mixture of methyl stearate, the compound prepared in Example 16A and a catalytic amount of lithium amide is heated at reflux in xylene. Methanol is distilled from the reaction mixture. The reaction is quenched with dilute acid. The organic layer is concentrated and the crude product is purified by flash chromatography on silica gel to afford the title compound as a white solid melting at 51–56° C.

EXAMPLE 73A 1-(4-Octadecanoyloxy-2,2,6,6-tetramethylpiperidin-1-yloxy)-2-octadecanoyloxy-2-methylpropane The title compound is prepared by the reaction of the compound prepared in Example 16A with excess methyl stearate and a catalytic amount of lithium amide in xylene.

EXAMPLE 74

4-Hydroxy-1-(2-hydroxy-1-phenethoxy)-2,2,6,6-tetramethylpiperidine

The title compound is prepared by heating a methanolic solution of the compound obtained in Example 10 with potassium hydroxide.

EXAMPLE 75

Poly[4-hydroxy-1-(2-hydroxy-1-phenylethoxy)-2,2,6,6-tetramethylpiperidin-4-yl Succinate]

The title compound is prepared by the reaction of approximately equimolar amounts of dimethyl succinate and the compound obtained in Example 74.

EXAMPLE 76

Stabilization of Thermoplastic Olefins

Molded test specimens are prepared by injection molding thermoplastic olefin (TPO) pellets containing pigments, a phosphite, a phenolic antioxidant or hydroxylamine, a metal stearate, ultraviolet light absorbers or a hindered amine stabilizer or a mixture of UV absorber and hindered amine stabilizer.

Pigmented TPO pellets are prepared from pure pigment or pigment concentrate, coadditives and commercially available TPO by mixing the components in a Superior/MPM 1" single screw extruder with a general all-purpose screw (24:1 L/D) at 400° F. (200° C.), cooled in a water bath and pelletized. The resulting pellets are molded into 60 mil (0.006 inch), 2"×2" plaques at about 375° F. (190° C.) on a BOY 30M Injection Molding Machine.

Pigmented TPO formulation composed of polypropylene blended with a rubber modifier where the rubber modifier is an in-situ reacted copolymer or blended product containing copolymers of propylene and ethylene with or without a ternary component such as ethylidene norbomene are stabilized with a base stabilization system consisting of an N,N-dialkylhydroxylamine or a hindered phenolic antioxidant with or without an organophosphorus compound.

All additive and pigment concentrations in the final formulation are expressed as weight percent based on the resin.

Formulation contained thermoplastic olefin pellets and one or more of the following components:

0.0 to 2.0% pigment,
0.0 to 50.0% talc,
0.0 to 0.1% phosphite,
0.0 to 1.25% phenolic antioxidant,
0.0 to 0.1% hydroxylamine
0.05 to 0.10 calcium stearate,
0.0 to 1.25% UV absorber
0.0 to 1.25% hindered amine stabilizer.

The components are dry-blended in a tumble dryer prior to extrusion and molding.

Test plaques are mounted in metal frames and exposed in an Atlas Ci65 Xenon Arc Weather-Ometer at 70° C. black panel temperature, 0.55 W/m² at 340 nonometers and 50% relative humidity with intermittent light/dark cycles and water spray (Society of Automotive Engineers—SAE J 1960 Test Procedure). Specimens are tested at approximately 625 kilojoule intervals by performing color measurements on an Applied Color Systems spectrophotometer by reflectance mode according to ASTM D 2244-79. Data collected include delta E, L*, a* and b* values. Gloss measurements are conducted on a BYK-Gardner Haze/Gloss Meter at 60° according to ASTM D 523.

UV Exposure Testing

Test speciments exposed to UV radiation exhibit exceptional resistance to photodegration when stabilized with light stabilizer systems comprising a combination of 2-(2-hydroxy-3,5-di-tert-amylphenyl)-2H-benzotriazole (TINUVIN®328, Ciba), the compound of Example 73 and N,N',N",N'"-tetrakis[4,6-bis(butyl-(1,2,2,6,6-pentamethylpiperidin-4-yl)amino)-s-triazin-2-yl]-1,10-diamino-4,7-diazadecane (CHIMASSORB® 119, Ciba). The control sample consists of a stabilizer formulation commonly used in the industry to impart UV stability. All of the samples contain a pigment, Pigment Red 177, and talc.

The test plaques described earlier contain the following (all concentrations are weight percent based on resin):

Polymer substrate is commercially available polyolefin blend POLYTROPE® TPP 518-01 supplied by A. Schulman Inc. Akron, Ohio)

Color package is 0.025% Red 3B -Pigment Red 177, C.I. #65300.

Each plaque contains:
0.2% TINUVIN® 328;
0.1% calcium stearate; and
15% talc.

The Control plaques additionally contain
0.1% IRGANOX® B225 (50:50 blend of IRGANOX® 1010, Ciba (neopentanetetrayl tetrakis(4-hydroxy-3,5-di-tert-butylhydrocinnamate) and IRGAFOS® 168, Ciba [tris-(2,4-di-tert-butylphenyl)phosphite;
0.2% TINUVIN® 770, Ciba [bis(2,2,6,6-tetramethylpiperidin-4-yl)sebacate];
0.2% CHIMASSORB 944, Ciba [polycondensation product of 4,4'-hexamethylene-bis(amino-2,2,6,6-tetramethylpiperidine) and 2,4-dichloro-6-tert-olamino-s-triazine].

The two test plaques (NOR-1 and NOR-2) each contain 0.05% N,N,-dialkylhydroxylamine;
NOR-1 additionally contains
0.2% of CHIMASSORB® 119; and
0.2% of TINUVIN® 123, Ciba, [bis(1-octyloxy-2,2,6,6-tetramethylpiperidin-4-yl)sebacate].
NOR-2 additionally contains
0.2% of CHIMASSORB® 119; and
0.2% of the compound of Example 73.

The results of the UV testing are given in the table below.

| Sample | DE* 0 Kj/m² | DE* 3000 Kj/m² | Gloss Value 0 Kj/m² | Gloss Value 3000 Kj/m² | % Gloss Value 0 Kj/m² | % Gloss Value 3000 Kj/m² |
|---|---|---|---|---|---|---|
| control | 0.0 | 4.7 | 66.6 | 5.4 | 100 | 8.1 |
| NOR-1 | 0.0 | 4.0 | 65.5 | 16.9 | 100 | 25.8 |
| NOR-2 | 0.0 | 3.8 | 64.9 | 45.3 | 100 | 69.8 |

The compound of Example 73 present in test plaques NOR-2 specifically shows greatly improved gloss retention compared to the less effective control system and in fact is also more effective that a related hindered amine compound (TINUVIN® 123) present in test plaques NOR-1. Resistance to color change upon UV exposure is also enhanced.

Polymer blends containing an unsaturated ternary component, such as EPDM blends, are especially benefited with the more efficient instant light stabilizer systems described above.

In all cases, the light stabilized formulations show much greated resistance to photodegradation than unstabilized specimens which fail quickly under the UV exposure conditions outlined above.

EXAMPLE 77

Paintable TPO

Molded test specimens are prepared by injection molding thermoplastic olefin (TPO) pellets containing the instant compounds, pigments and other coadditives as described in Example 76.

The light stable formulations are painted with one-pack paint systems and tested for TPO/paint interactions. Before painting, the test specimens are first washed in accordance with GM998-4801 and dried for 15 minutes at 200° F. (94° C.). Adhesion promoter is applied to the dry film thickness of 0.2–0.4 mils. The samples are dried for five minutes before a 1K basecoat is applied to a film thickness of 1.2–1.4 mils. The painted panels are dried for three minutes, a clearcoat is then applied to a dry film thickness of 1.2–1.5 mils followed by ten minutes flash drying and a 30 minute oven bake at 250° F. (121° C.).

Paint adhesion is measured by Aggressive Adhesion Testing (proprietary test procedure conducted at Technical Finishing, Inc.) and Taber Scuff. Painted panels which retain greater than 80% of the paint finish are considered acceptable. After Aggressive Adhesion Testing, samples with less than 5% paint loss are deemed acceptable.

Samples are tested to evaluate the TPO/paint interactions as follows:

| Formulation* | Taber Scuff Test | Aggresive Adhesion Test | HALS pK$_a$ |
|---|---|---|---|
| A | 100% removed | 6% Loss (fail) | 9.1 |
| B | 0% removed | 4% Loss (pass) | 4.6 |
| C | 0% removed | 3% Loss (pass) | 4.0 |

Formulation A contains 0.2% CHIMASSORB® 944, 0.2% TINUVIN® 328, 500 ppm calcium stearate and 750 ppm N,N-dialkylhydroxylamine in reactor-grade TPO. A also contains 0.2% of bis(2,2,6,6-tetramethylpiperidin-4-yl) sebacate (TINUVIN® 770, pK$_a$ of 9.1).

Formulations B and C contain 0.2% CHIMASSORB® 119, 0.2% TINUVIN® 328, 500 ppm calcium stearate and 750 ppm N,N-dialkylhydroxylamine in reactor-grade TPO. B also contains 0.2% of bis(1-octyloxy-2,2,6,6-tetramethylpiperidin-4-yl)sebacate (TINUVIN® 123, $pK_a$ of 4.6).

C also contains 0.2% of 1-(2-hydroxy-2-methylpropoxy) 4octadecanoyloxy-2,2,6,6-tetramethylpiperidine (compound of Example 73, $pK_a$ of 4.0)

The data in the table indicate that, although formulation A failed in both the Taber Scuff and Aggressive Adhesion Tests, both formulations B and C passed both paint adhesion tests. However, as inspection of the $pk_a$ values attests, the lower the $pk_a$ value (less basic) for the test hindered amine compound the less paint loss results in this Aggressive Adhesion Test. The instant compound of Example 73 having the hydroxyl moiety present has the lowest $pK_a$ value and also the least paint loss even better than the close prior art compound where no hydroxyl moiety is present.

EXAMPLE 78

Stabilization of Polypropylene Molded Articles

Molded test specimens are prepared by injection molding polypropylene pellets containing pigments, a phosphite, a phenolic antioxidant or hydroxylamine, a metal stearate, ultraviolet light absorbers or a hindered amine stabilizers or a mixture of UV absorbers and hindered amine stabilizers.

Pigmented polypropylene pellets are prepared from pure pigment or pigment concentrates, stabilizers, co-additives and commercially available polypropylene by mixing the components in a Superior/MPM 1"single screw extruder with a general all-purpose screw (24:1 L/D) at 475° F. (250° C.), cooled in a water bath and pelletized. The resulting pellets are molded into 60 mil (0.06 inch thick) 2"×2" plaques at about 475° F. (250° C.) on a BOY 30M Injection Molding Machine.

Pigmented polypropylene formulations composed of polypropylene homopolymer or polypropylene copolymer are stabilized with a base stabilization system consisting of an N,N-dialkylhydroxylamine or a hindered phenolic antioxidant with or without an organophosphorous compound.

All additive and pigment concentrations in the final formulations are expressed as weight percent based on the resin.

Formulations contained polypropylene pellets and one or more of the following components;

0.0%–2.0% pigment,
0.0%–50.0% talc,
0.0%–50.0% calcium carbonate,
0.0%–0.1% phosphite,
0.0%–1.25% phenolic antioxidant,
0.0%–0.1% hydroxylamine,
0.05%–0.10% calcium stearate,
0.0%–1.25% UV absorber,
0.0%–1.25% hindered amine stabilizer.

The components are dry blended in a tumble dryer prior to extrusion and molding.

Test plaques are mounted in metal frames and exposed in an Atlas Ci65 Xenon Arc Weather-o-meter at 70° C. black panel temperature, 0.55 W/m$^2$ at 340 nanometers and 50% relative humidity with intermittent lightdark cycles and water spray (Society of Automotive Engineers—SAE J 1960 Test Procedure). Specimens are tested at approximately 625 kilojoule intervals by performing color measurements on an Applied Color Systems spectrophotometer by reflectance mode according to ASTM D 2244-79. Data collected included delta E, L*, a* and b* values. Gloss measurements are conducted on a BYK-GARDNER Haze/Gloss Meter at 60° according to ASTM D523.

UV Exposure Testing

Test specimens exposed to UV radiation exhibit exceptional resistance to photodegradation when stabilized with light stabilizer systems comprised of a combination of Tinuvin 328, the compound of Example 73 and CGL 2020. CGL 2020 is oligomer of N-{[2-(N-2,2,6,6-tetramethylpiperidin-4-yl)butylamino]-s-triazin-4-yl}-N,N'-bis(2,2,6,6-tetramethylpiperidin-4-yl)-1,6-hexanediamine terminated with 2,4-bis(dibutylamino)-s-triazin-yl. The Control sample consists of a stabilizer formulation commonly used in the industry to impart UV stability. All of the samples contain Pigment Red 177.

|  | Red 3B Formulations | | | DE* | | Gloss Values | | % Gloss Retention | |
|---|---|---|---|---|---|---|---|---|---|
|  |  |  |  |  | 3000 |  | 3000 |  | 3000 |
|  | Comp. 1 | Comp. 2 | Comp. 3 | 0 Kj/m$^2$ | Kj/m$^2$ | 0 Kj/m$^2$ | Kj/m$^2$ | 0 Kj/m$^2$ | Kj/m$^2$ |
| Control | 0.14% T 123 | 0.20% CGL 2020 | 0.2% Tin. 328 | 0 | 6.5 | 88% | 24% | 100% | 28% |
| Ex. 73 | 0.10% Ex. 73 | 0.10% CGL 2020 | 0.1% Tin. 328 | 0 | 0.6 | 88% | 77% | 100% | 88% |
| NOR 2 | 0.10% NOR 2 | 0.10% CGL 2020 | 0.1% Tin. 328 | 0 | 8.2 | 87% | 13% | 100% | 14% |

• All formulations are base stabilized with 0.05% dialkylhydroxylamine in the final resin formulation.
• Polymer substrate is a commercially available polypropylene homopolymer - Profax 6501 (commercial supplier Montell Polyolefins).
• Color package is 0.25% Red 3B - Pigment Red 177, C.I. #65300 in the final resin formulation.
• Each formulation contains a hydroxyphenyl benzotriazole UV absorber - Tinuvin 328, 2-(2-hydroxy-3, 5-di-tert-amylphenyl)-2H-benzotriazole.
• NOR 2 is bis(1-cyclohexyloxy-2,2,6,6-tetramethylpiperidin-4-yl)succinate.
• Each formulation contains 0.1% calcium stearate.
• Samples are 60 mil thick 2" × 2" injection molded plaques.
• UV exposures conducted under SAE J 1960 - Exterior Automotive conditions.

All additive and pigment concentrations in the final formulations are expressed as weight percent on the resin.

The formulation containing the subject compound of Example 73 specifically shows greatly improved gloss retention compared to the less effective Control stabilizer system even at a lower total concentration. Resistance to color change upon UV exposure is also significantly enhanced. The subject compound of Example 73 is also significantly more effective in maintaining appearance when compared with another solid N-O-R HALS (NOR 2) of similar molecular at equal concentrations.

In all cases, the light stabilized formulations show much greater resistance to photodegradation than unstabilized specimens which fail quickly under the UV exposure conditions outlined above.

EXAMPLE 79

Polypropylene Fiber

Fiber samples are prepared by extruding fiber-grade polypropylene with the instant compounds, coadditives and pigments. Typical formulations contain the instant compounds at levels from 0.05 to 2.0%, a metal stearate such as calcium stearate at 0.05 to 0.5%, pigments from 0 to 5%, UV absorbers at levels of 0.05 to 2.0%, phosphites at 0 to 0.1%, phenolic antioxidants at 0 to 1.25%, N,N-dialkylhydroxylamines at 0 to 0.1% and optionally other hindered amines at levels of 0 to 2.0%. All additive and pigment concentrations in the final formulations are given as weight percent based on the resin.

Pigment concentrates are prepared from pure pigment and polypropylene (PROFAX®, Hercules) by mixing the two components in a high shear mixer in a ratio of 25% pigment and 75% resin, pressing the resulting resin/pigment mixture on a Wabash Compression molder (Model # 30-1515-4T3) into a thin sheet and dividing the sheet into fine chips for dispersion in polypropylene at reduced concentrations. Alternatively, pigment concentrates areobtained as pigment dispersions in a suitable carrier resin for subsequent blending in fiber at reduced concentrations.

Formulations containing polypropylene, 0.05–0.1% phosphite, 0–1.25% phenolic antioxidant, 0–0.1% dialkylhydroxylamine, 0.05–0.1% calcium stearate, 0–1.25% UV absorber, 0–1.25% hindered amine are dry blended in a tumble dryer, extruded on a Superior/MPM 1" single screw extruder with a general all-purpose screw (24:1 L/D) at 475° F. (246° C.), cooled in a water bath and pelletized. The resulting pellets are spun into fiber at about 475° F. (246° C.) on a HILLS Research Fiber Extruder (Model # REM-3P-24) fitted with a 41 hole, delta configuation spinneret. The spun tow is stretched at a draw ratio of 3.2:1 producing a final denier of 615/41.

Fiber samples are knitted into socks on a Lawson-HemphillFiber Analysis Knitter, cut into appropriate lengths and exposed in an Atlas Ci65 Xenon Arc Weather-C-meter at 89° C. black panel temperature, 0.55 W/m$^2$ at 340 nanometers and 50% relative humidity (Society of Automotive Engineers—SAE J 1885 Test Procedure).

Fiber samples are tested by performing color measurements on an Applied Color Systems spectrophotometer by reflectance mode according to ASTM D 2244-79. Identical, but separate, fiber samples are examined for catastrophic failure and the time to failure is recorded.

The samples containing the instant compounds exhibit good stabilization performance against the deleterious effects of UV light.

EXAMPLE 80

Other socks of propylene fiber as prepared in Example 79 are exposed in a Blue M forced draft oven at 120° C. Failure is determined by the criterion set forth in Example 79. The longer it takes for the catastrophic failure to occur, the more effective is the stabilizing system.

The socks containing the instant compounds exhibit good thermal stabilization efficacy.

EXAMPLE 81

Film grade polyethylene is dry blended with approximately 10% by weight of the test additives, such as the compound of Example 51, and then melt compounded at 200° C. into "Masterbatch" pellets. The fully formulated "Masterbatch" pellets are dry blended with polyethylene resin to get the desired final stabilizer concentrations. Typical formulations contain the instant compounds at levels from 0.05% to 2.0%, a metal stearate such as calcium stearate at 0.05% to 0.5%, a phosphite at 0% to 0.1%, a phenolic antioxidant at 0% to 1.25%, an N,N-dialkylhydroxylamine at 0% to 0.1% and optionally a hindered amine at 0% to 2.0%. The This stabilized fully formulated resin is then blown at 200° C. into a 150 micron thick film on a DOLCI film line.

The blown films are exposed in an Atlas Xenon-Arc WeatherOmeter according to ASTM G26 at 63° C. bpt, 0.35 W/m$^2$ at 340 nm with no spray cycle. Films are tested periodically for any change in elongation using an Instron 112 tensile tester. Failure in this test is determined by observation of the loss of % elongation in the film. The longer it takes for this loss to occur, th more effective is the stabilizer system.

The films containing the instant compound mixture show good light stabilizing efficacy.

EXAMPLE 82

Film grade polyethylene is dry blended with 10% loading of the test additives, such as the compound of Example 51, as described in Example 81, and then melt compounded at 200° C. into fully formulated master batch pellets. The master batch pellets are dry blended with the polyethylene resin to get the final stabilizer concentration. The fully formulated resin is then blown at 200° C. into a 150 micron thick film using a DOLCI film line.

The resulting films are exposed on a greenhouse on galvanized iron backing. Treatment includes applications of pesticides on a regular basis (i.e. sodium N-methyidithiocarbamate, VAPAM every six months and SESMETRIN every month). Performance is measured by monitoring the percent residual elongation. Failure is defined as the time to a 50% loss of original elongation.

The films containing the instant compounds show good resistance to pesticides.

EXAMPLE 83

Master batch pellets prepared as described in Example 81 are dry blended into polyethylene resin to get the final stabilizer cocentration. The fully formulated resin is then blown at 200° C. into a 25 micron thick film using a DOLCI film line.

The resulting films are exposed on a soil to simulate agricultural mulch film conditions. Treatment includes exposure to methyl bromide fumigant for three days at 60 g/m$^3$. Performance is measured by monitoring the time to physical embrittlement.

The films containing the instant compounds show good resistance to fumigants.

EXAMPLE 84

Greenhouse film samples are prepared as described in Example 81, but in addition to the instant compounds also contain a metal stearate or a metal oxide. Typical formulations contain from 0.05 to 2% by weight of the instant hindered amines, 0.05 to 0.5% of a metal stearate such as calcium oxide, and 0.05 to 0.5% of a metal oxide such as zinc oxide or magnesium oxide.

Effectiveness is monitored as described in Example 82. The films containing the instant compounds exhibit good light stability.

EXAMPLE 85

Polypropylene fiber is prepared as described in Example 79. In addition to the instant compounds, selected halogenated flame retardants are also included in the formulation. The flame retardants are tris(3-bromo-2,2-bis(bromomethyl)propyl)phosphate, decabromodiphenyl oxide, ethylene bis-(tetrabromophthalimide), or ethylene bis-(dibromonorbomanedicarboximide).

Using the criterion for light stabilization described in Example 79, the socks knitted from the polypropylene fiber containing the instant compounds exhibit good light stability.

EXAMPLE 86

Molding grade polypropylene is dry blended with test additives and then melt compounded into pellets. In addition to the instant compounds, selected flame retardants are also included. The flame retardants are tris(3-bromo-2,2-bis(bromomethyl)propyl)phosphate, decabromodiphenyl oxide, ethylene bis-(tetrabromophthalimide), or ethylene bis-(dibromonorbomanedicarboximide). The pelletized fully formulated resin is then injection molded into test specimens using a Boy 50M laboratory model injection molder.

Test plaques are mounted in metal frames and exposed in an Atlas Ci65 Xenon Arc Weather-Ometer with intermittent light/dark cycles and water spray following the ASTM G26 test procedure. Specimens are tested at periodic intervals for changes in tensile properties. Failure in this test is determined by the observation of the loss of tensile properties. The longer it takes for the loss in properties to occur, the more effective is the stabilizer system.

The test samples containing the instant compounds exhibit good light stabilization properties.

EXAMPLE 87

Molded test specimens are prepared by injection molding thermoplastic olefin (TPO) pellets as described in Example 76. In addition to the instant compounds, selected flame retardants are also included in the test specimens. The flame retardants are tris(3-bromo-2,2-bis(bromomethyl)propyl)phosphate, decabromodiphenyl oxide, ethylene bis-(tetrabromophthalimide), or ethylene bis-(dibromonorbomanedicarboximide).

The samples including the instant hindered amines exhibit good light stabilizing activity.

EXAMPLE 88

Film grade polyethylene is compounded and blown into film at 200° C. as described in Example 82 using a DOLCI film line. In addition to the instant compounds, selected flame retardants are included in the formulation. The flame retardants are tris(3-bromo-2,2-bis(bromomethyl)propyl)phosphate, decabromodiphenyl oxide, ethylene bis-(tetrabromophthalimide), or ethylene bis-(dibromonorbomanedicarboximide).

When tested for light stabilizing activity as described in Example 82, the films containing the instant compounds exhibit good stabilization.

EXAMPLE 89

Molded test specimens are prepared by injection molding thermoplastic olefin (TPO) pellets containing the instant compounds, pigments and other coadditives as described in Example 77.

The test specimens are painted with one-pack paint systems and tested for TPO/paint interactions. Before painting, the test specimens are first wiped with isopropanol and air blasted to remove any dust. After a five minute flash, these specimens are coated with the adhesion promoter, then the base coat, and then optionally a clear coat. Typical film thickness of these various coatings are 0.1–0.3 mils for the adhesion promoter, 0.6–0.8 mils for the base coat, and 1.2–1.5 mils for the clear coat. After painting, the specimens are cured in an over at 120° C. for 30 minutes.

Samples are tested to evaluate the TPO/paint interactions as follows: In the initial adhesion test, a clear cellophane adhesive tape is used to pull on a 3 mm cross hatched paint surface or; in the humidity test, the painted plaques are exposed for 240 hours at 38° C. in an atmosphere having 98% relative humidity. The blister rating is tested by visual observation according to ASTM D 714.

The samples containing the instant compounds exhibit good TPO/paint interaction properties as determined by the criteria above.

EXAMPLE 90

Thermoplastic Elastomers

Resin materials of the general class known as thermoplastic elastomers, examples of which include, copolymers of styrene with butadiene or isoprene and/or ethylenecobutylene such as SBS, SEBS and SIS, are dry blended with the instant compounds and melt compounded into pellets. Typical formulations contain the instant compounds at levels from 0.05% to 2.0%, a metal stearate such as calcium stearate at 0.05% to 0.5%, pigments from 0% to 5%, UV absorbers at levels of 0.05% to 2.0%, phosphites at 0.0%–0.1%, phenolic antioxidants at 0.0%–1.25%, N,N-dialkylhydroxylamine at 0.0%–0.1%, and optionally other hindered amine stabilizers at levels of 0.0% to 2.0%.

The pelletized fully formulated resin is then processed into a useful article such as blown or cast extrusion into film; injection molded into a molded article; thermoformed into molded articles; extruded into wire and cable housing; or rotational molded into hollow articles.

The materials containing the instant compounds exhibit stability against deleterious effects of UV light and thermal exposure.

EXAMPLE 91

Articles prepared according to Example 90 which additionally contain selected organic pigments as well as the instant compounds also exhibit stability against the deleterious effects of actinic light and thermal exposure.

EXAMPLE 92

Articles prepared according to Example 90 which additionally contain a hindered phenolic antioxidant selected from the group consisting of neopentanetetrayl tetrakis(3,5-di-tert-butyl-4-hydroxyhydrocinnamate, octadecyl 3,5-di-tert-butyl-4-hydroxyhydrocinnamate, 1,3,5-trimethyl-2,4,6-tris(3,5,-di-tert-butyl-4-hydroxybenzyl)benzene, 1,2-bis(3,5-di-tert-butyl-4-hydroxyhydrocinnamoyl)hydrazine, calcium [bis(monoethyl 3,5-ditert-butyl-4-hydroxybenzyl)-phosphonate], 1,3,5-tris(3,5-di-tert-butyl-4-hydroxybenzyl) isocyanurate and 1,3,5-tris(3-hydroxy-4-tert-butyl-2,6-dimethylbenzyl)isocyanurate, as well as the instant compounds also exhibit stability against the deleterious effects of actinic light and thermal exposure.

EXAMPLE 93

Articles prepared according to Example 90 which additionally contain an organophosphomus stabilizer selected from the group consisting of tris(2,4-di-tert-butylphenyl) phosphite, bis(2,4-di-tert-butyl-6-methylphenyl)ethyl phosphite, 2,2',2"-nitrilo[triethyl-tris-(3,3',5,5'-tetra-tert-butyl-1,1'-biphenyl-2,2'-diyl)phosphite], tetrakis(2,4-di-butylphenyl) 4,4'-biphenylenediphosphonite, tris(nonylphenyl)phosphite, bis(2,4-di-tert-butylphenyl) pentaerythrityl diphosphite, 2,2'-ethylidenebis(2,4-di-tert-butylphenyl)fluorophosphite and 2-butyl-2-ethylpropan-1,3-diyl 2,4,6-tri-tert-butylphenyl phosphite as well as the instant compounds of also exhibit stability against the deleterious effects of actinic light and thermal exposure.

EXAMPLE 94

Articles prepared according to Example 90 which additionally contain a benzofuranone stabilizer which is 5,7-di-tert-butyl-3-(3,4-dimethylphenyl)-2H-benzofuran-2-one, as well as the instant compounds also exhibit stability against the deleterious effects of UV light and thermal exposure.

EXAMPLE 95

Articles prepared according to Example 90 which additionally contain a dialkylhydroxylamine stabilizer which is N,N-dialkylhydroxylamine made by the direct oxidation of N,N-di(hydrogenated tallow)amine as well as the instant compounds also exhibit stability against the deleterious effects of actinic light and thermal exposure.

EXAMPLE 96

Articles prepared according to Example 90 which additionally contain other hindered amine stabilizers selected from the group consisting of bis(2,2,6,6-tetramethylpiperidin-4-yl)sebacate, the polycondensation product of 1-(2-hydroxyethyl)-2,2,6,6-tetramethyl-4-hydroxypiperidine and succinic acid, N,N',N",N'"-tetrakis[4,6-bis(butyl-1,2,2,6,6-pentamethylpiperidin-4-yl)amino-s-triazin-2-yl]-1,10-diamino4,7-diazadecane, the polycondensation product of 4,4'-hexamethylenebis(amino-2,2,6,6-tetramethylpiperidine) and 2,4-dichloro-6-tert-octylamino-s-triazine, the polycondensation product of 4,4'-hexamethylenebis(amino-2,2,6,6-tetramethylpiperidine) and 2,4-dichloro-6-morpholino-s-triazine, 2,2,6,6-tetramethylpiperidin-4-yl octadecanoate, 3dodecyl-1-(1-acetyl-2,2,6,6-tetramethylpiperidin-4-yl)-pyrrolidin-2,5dione, 1,3,5tris{N-cyclohexyl-N-[2-(2,2,6,6-tetramethylpiperazin-3-on-4-yl)ethyl]amino}-s-triazine, poly[methyl 3-(2,2,6,6-tetramethylpiperidin-4-yloxy)propyl]siloxane, the polycondensation product of 2,4-dichloro-6-2,2,6,6-tetramethylpipeddin-4-yl)butylamino)-s-triazine and 2,2'ethylene-bis{[2,4-(2,2,6,6-tetramethylpiperidin-4-yl)butylamino-s-triazin- 6-yl] aminotrimethyleneamino} as well as the instant compounds also exhibit stability against the deleterious effects of actinic light and thermal exposure.

EXAMPLE 97

Articles prepared according to Example 90 which additionally contain other N-hydrocarbyloxy substituted hindered amines selected from the group consisting of bis(1-octyloxy-2,2,6,6-tetramethylpiperidin-4-yl)sebacate, bis(1-octyloxy-2,2,6,6-tetramethylpiperidin-4-yl)adipate, bis(1-cyclohexyloxy-2,2,6,6-tetramethylpiperidin-4-yl)adipate, bis(1-cyclohexyloxy-2,2,6,6-tetramethylpiperidin-4-yl) sebacate, and 1-cyclohexyloxy-2,2,6,6-tetramethylpiperidin-4-yl octadecanoate as well as the instant compounds also exhibit stability against the deleterious effects of actinic light and thermal exposure.

EXAMPLE 98

Articles prepared according to Example 90 which additionally contain a o-hydroxyphenyl-2H-benzotriazole, a hydroxyphenyl benzophenone or a o-hydroxyphenyl-s-triazine UV absorber selected from the group consisting of 2-(2-hydroxy-3,5-di-α-cumylphenyl)-2H-benzotriazole, 2-(2-hydroxy-5-methylphenyl)-2H-benzotriazole, Schloro-2-(2-hydroxy-3,5-di-tertbutylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl4-hydroxybenzoate, 2-hydroxy-4-n-octyloxybenzophenone and 2,4-bis(2,4-dimethyphenyl)-6-(2-hydroxy-4-octyloxyphenyl)-s-triazine as well as the instant compounds also exhibit stability against the deleterious effects of UV light and thermal exposure.

EXAMPLE 99

The hindered amine test stabilizers are incorporated into a two-component polyester urethane coating based on a commercially available polyester polyol (DESMOPHEN® 670-80) and commercially available isocyanurate (DESMODUR® N-3390) at a level of 2% by weight based on total resin solids. The coating system is catalyzed with 0.015% dibutyl tin dilaurate based on total resin solids.

Each coating formulation is applied by drawdown onto transparent glass slides approximately 4"×6" to a film thickness of about 2 mils (0.002") in triplicate.

These triplicate glass plates are processed as seen below:

Plate 1—bake for 30 minutes at 180° F. (82° C.); age at room temperature; and observe daily.

Plate 2—allow to air dry (ambient cure); age at room temperature; and observe daily.

Plate 3—allow to air dry for one day; age in a 120° F. (49° C.) oven; observe daily and continue aging at 120° F. (49° C.).

Starting at time zero, all plates are evaluated for visual appearance, noting the development of any cloudiness within the coating and any exudate on the surface of the coating. The results of four days of observation are noted below.

| Sample* | 0 | Day 1 | Day 2 | Day 3 | Day 4 | 18 months |
|---------|-----|-------|-------|-------|-------|-----------|
| Plate 1 | | | | | | |
| A | cl | cl | cl | cl | cl | clear |
| B | sl h | haze | haze | haze | haze | haze |
| C | cl | cl | cl | d | cl | clear |
| Plate 2 | | | | | | |
| A | cl | cl | cl | cl | cl | clear |
| B | sl h | haze | haze | haze | haze | haze |
| C | cl | cl | cl | cl | d | clear |
| Plate 3 | | | | | | |
| A | cl | cl | cl | d | d | clear |
| B | sl h | haze | haze | haze | haze | haze |
| C | cl | cl | cl | cl | cl | clear |

*A is unstabilized.
B contains 2% by weight of bis(1-octyloxy-2,2,6,6-tetramethylpiperidin-4-yl) sebacate (TINUVIN ® 123).
C contains 2% by weight of bis[1-(2-hydroxy-2-methylpropoxy)-2,2,6,6-tetramethylpiperidin-4-yl] sebacate, compound of Example 2.

These data show that the instant compound having a hydroxy moiety present on the group attached to the 1-position of the hindered amine provides excellent solubility and compatibility for the polyester urethane coating that cannot be achieved with the closest prior art compound where said hydroxy moiety is absent.

Experience teaches that, if the instant compounds are soluble and compatible in this particular clearcoat, they will certainly be compatible and soluble in other resin systems.

EXAMPLE 100

Approximately 50 mL of the same stabilized formulated two-component clear coatings described in Example 99 are allowed to gel in a sealed 4 ounce jar. The solidified coatings are visually observed for clarity after solidification. The development of opacity or cloudiness is indicative of an incompatibility between the hindered amine stabilizer and the formulated coating.

| | Solidified coating in jar | | | |
|---|---|---|---|---|
| Sample* | 0 | Day 1 | Day 2 | 18 months |
| A | clear | clear | clear | clear |
| B | clear | cloudy | cloudy | cloudy |
| C | clear | clear | clear | clear |

*A is unstabilized.
B contains 2% by weight of bis(1-octyloxy-2,2,6,6-tetramethylpiperidin-4-yl) sebacate (TINUVIN ® 123).
C contains 2% by weight of bis[1-(2-hyrdoxy-2-methylpropoxy)-2,2,6,6-tetramethylpiperidin-4-yl] sebacate, compound of Example 2.

These data show that the instant compound having a hydroxy moiety present on the group attached to the 1-position of the hindered amine provides excellent solubility and compatibility for the polyester urethane coating that cannot be achieved with the closest prior art compound where said hydroxy moiety is absent.

EXAMPLE 101

1-(2-Hydroxy-2-methylpropoxy)-4-[9-(methoxycarbonyl)nonanoyloxy]-2,2,6,6-tetramethylpiperidine The title compound is prepared by the reaction of the compound prepared in Example 16A with one equivalent or more of dimethyl sebacate and a catalytic amount of lithium amide in xylene.

EXAMPLE 102

1-(2-Hydroxy-2-methylpropoxy)-4-[5-(methoxycarbonyl)pentanoyloxy]-2,2,6,6-tetramethylpiperidine The title compound is made by the procedure of Example 101 where dimethyl sebacate is replaced by an equivalent amount of dimethyl adipate.

EXAMPLE 103

1-(2-Hydroxy-2-methylpropoxy)-4-[3-(methoxycarbonyl)propionyloxy]-2,2,6,6-tetramethylpiperidine The title compound is made by the procedure of Example 101 where dimethyl sebacate is replaced by an equivalent amount of dimethyl succinate.

EXAMPLE 104

1-(2-Hydroxy-2-methylpropoxy)-4-[4-(methoxycarbonyl)butyryloxy]-2,2,6,6-tetramethylpiperidine The title compound is made the procedure of Example 101 where dimethyl sebacate is replaced by an equivalent amount of dimethyl glutarate.

EXAMPLE 105

Condensation Product of 4-Hydroxy-1-(2-hydroxy-2-methylpropoxy)-2,2,6,6-tetramethylpiperidine with Hexamethylene Diisocyanate, and Terminated with Methoxy The title compound is prepared from the reaction of approximately equimolar amounts of the compound prepared in Example 16A with hexamethylene diisocyanate followed by reaction with excess methanol.

EXAMPLE 106

Condensation Product of 4-Hydroxy-1-(2-hydroxyethoxy)-2,2,6,6-tetramethylpiperidine with Hexamethylene Diisocyanate, and Terminated with Methoxy The title compound is prepared from the reaction of approximately equimolar amounts of the compound prepared in Example 70 with hexamethylene diisocyanate, followed by reaction with excess methanol.

EXAMPLE 107

Condensation Product of 4-Hydroxy-1-(2-hydroxy-1-phenethoxy)-2,2,6,6-tetramethylpiperidine with Hexamethylene Diisocyanate, and Terminated with Methoxy The title compound is prepared from the reaction of approximately equimolar amounts of the compound prepared in Example 74 with hexamethylene diisocyanate, followed by reaction with excess methanol.

EXAMPLE 108

Stabilization of a Two-Component Acrylic Urethane Clearcoat

The hindered amine test stabilizers are incorporated into a two-component acrylic urethane coating as described om Example 99. The system is catalyzed with 0.02% by weight of dibutyltin dilaurate based on the total resin solids. The stabilizers are added at the appropriate level to the acrylic polyol portion of the two-component coating which is then combined with the isocyanate component immediately prior to application.

Steel panels 3"×4" primed with an electrocoat primer are then coated with a light blue metallic basecoat, then with the stabilized clearcoat. The basecoat is spray applied to a thickness of 1.0 mil (25 microns) dry film thickness and the stabilized clearcoat is then applied to a thickness of 2.0 mils (50 microns) dry film thickness. The coating is air-dried and aged for two weeks. The panels are then exposed in a Xenon-Arc Weather-Ometer under the following conditions:

Cam 180 cycle: 40 minutes light only; 20 minutes light and front spray; 60 minutes light only; 60 minutes dark and rear spray condensate.

Lamp filters are: quartz inner/borosilicate S outer.

Irradiance: 0.45 watts per square meter.

20° Gloss is measured before exposure and at 500 hour intervals during exposure. Higher gloss retention is desirable.

| | Percent Retention of 20° Gloss | | |
|---|---|---|---|
| Sample* | 4500 hours | 8500 hours | 12000 hours |
| A | 17 | — | — |
| B | 60 | 22 | — |
| C | 47 | 17 | — |
| D | 34 | 22 | — |
| E | 41 | 23 | — |
| F | 75 | 45 | 28 |
| G | 77 | 45 | 27 |

*A is unstabilized.
B contains 1% by weight of bis(1-octyloxy-2,2,6,6-tetramethylpiperidin-4-yl) sebacate (TINUVIN ® 123).
C contains 0.9% by weight of bis[1-(2-hydroxy-2-methylpropoxy)-2,2,6,6-tetramethylpiperidin-4-yl] sebacate, compound of Example 2.
D contains 1.04% by weight of 2,4-bis[N-(1-cyclohexyloxy-2,2,6,6-tetramethylpiperidin-4-yl)-N-butylamino]-6-(2-hydroxyethylamino)-s-triazine.
E contains 1.01% by weight of the compound of Example 12.
F contains 2% by weight of bis(1-octyloxy-2,2,6,6-tetramethylpiperidin-4-yl) sebacate (TINUVIN ® 123).
G contains 1.8% by weight of bis[1-(2-hydroxy-2-methylpropoxy)-2,2,6,6-tetramethylpiperidin-4-yl] sebacate, compound of Example 2.

These data show that the instant hydroxy substituted compounds give comparable 20° Gloss Retention values to NOR compounds at equivalent molar concentrations.

EXAMPLE 109

Stabilization of a Two-Component Acrylic Urethane Clearcoat

A clearcoat as prepared in Example 108 is applied by spin-coating to 1" silicon disks to a dry film thickness of approximately 25 microns. The initial optical film thickness of each disk is measured using a Zeiss interferometer. The disks are then exposed in a Xenon-Arc Weather-Ometer under the following conditions:

Cam 180 cycle: 40 minutes light only; 20 minutes light and front spray; 60 minutes light only; 60 minutes dark and rear spray condensate.

Lamp filters are: quartz inner/quartz outer.

Irradiance: 0.55 watts per square meter.

Optical film thickness is remeasured every 250 hours and film loss is determined for each formulation. The film loss caused by weathering after 3972 and 5561 hours is tabulated in the table below. A lower value for film loss is desirable.

| | Film Loss (in microns) | |
|---|---|---|
| Sample* | 3972 hours | 5561 hours |
| A | 23.3 | complete erosion |
| B | 6.9 | 16.3 |
| C | 6.7 | 17.8 |
| D | 6.3 | 14.3 |
| E | 5.9 | 12.4 |
| F | 6.5 | 16.1 |
| G | 6.6 | 16.7 |

*A is unstabilized.
B contains 1% by weight of bis(1-octyloxy-2,2,6,6-tetramethylpiperidin-4-yl) sebacate (TINUVIN ® 123).
C contains 0.9% by weight of bis[1-(2-hydroxy-2-methylpropoxy)-2,2,6,6-tetramethylpiperidin-4-yl] sebacate, compound of Example 2.
D contains 1.04% by weight of 2,4-bis[N-(1-cyclohexyloxy-2,2,6,6-tetramethylpiperidin-4-yl)-N-butylamino]-6-(2-hydroxyethylamino)-s-triazine.
E contains 1.01% by weight of the compound of Example 12.
F contains 0.78% by weight of 1-octyloxy-2,2,6,6-tetramethyl-4-hydroxypiperidine.
G contains 0.56% by weight of 1-(2-hydroxy-2-methylpropoxy)-2,2,6,6-tetramethyl-4-hydroxy-piperidine, compound of Example 16A.

These data show that the instant hydroxy substituted compounds give comparable resistance to erosion as the closest NOR compounds at equivalent molar concentrations.

EXAMPLE 110

Coatings over Plastic Substrates

A major application for non-basic hindered amines is in the protection of automotive topcoats applied over plastic substrates. However, many low molecular weight, non-reactable light stabilizers migrate into the plastic substrate during drying and cure. As a consequence, a significant portion of the light stabilizer may be lost from the topcoat into the substrate and hence be ineffective in protecting said topcoat.

The extent of migration of hindered amine stabilizers during application and cure of the coating is determined by comparing the concentration of hindered amine in the cured clearcoat applied over a plastic substrate versus the same clearcoat applied over a non-permeable substrate such as glass or steel.

Hindered amine stabilizers under test are incorporated into a flexible thermoset acrylic/melamine clear coating appropriate for use on automotive plastic substrates. The hindered amine is incorporated at a level of 1.5% by weight based on total resins solids.

Each coating formulation is applied by an automatic spray appratus onto automotive grade RIM (Reacting Injection Molded) substrate and TPO (thermoplastic polyolefin). Both substrates are in form of 4"×12" plaques. Each coating is applied to achieve a dry film thickness of approximately 2.0 mils (50 microns). The coatings are cured by baking at 250° F. (121° C.) for 20 minutes.

Triplicate samples of each cured coating formulation are removed from each substrate and cryoground to a fine powder. A known amount of each sample is extracted in refluxing toluene overnight The hindered amine present is analyzed quantitatively by dilution to a known volume and analyzed by HPLC or SFC chromatography. Calibration curves for each test stabilizer compound are developed. The hindered amine content of each extracted coating is determined by this method.

When the instant hindered amine compounds substituted on the N-atom with an -O-E-OH moiety are compared to the corresponding -NOR compounds lacking such a hydroxyl moiety, a higher percent recovery of the instant hindered amine compound from the clearcoat over a plastic substrate is found indicating that much less of the instant hindered amine stabilizer migrates into the plastic substrate allowing for better stabilization of the clear topcoat over such plastic substrates.

EXAMPLE 111

Stabilization of Waterborne Wood Varnish

Waterborne coating comprise a significant and increasing proportion of the coating in use for a wide variety of applications including automotive basecoats, industrial coatings and trade sale coatings. These coatings may be pigmented or transparent. The trends are also towards higher solids formulation which in general depend on light stabilizers to maintain properties on exterior exposure, and towards lower levels of cosolvents. This requires higher solubility of stabilizers in such cosolvents (primarily water) or actual solubility in water.

The test stabilizers are incorporated into a waterborne dispersion by predissolution in a cosolvent blend. The waterborne dispersion is a commercially available acrylic/urethane hydrid resin. The cosolvent blend is a 1:1 mixture of TEXANOL® (2,2,4-trimethyl-1,3-pentanediol, Texaco) and ARCOSOLVE® TPM (tripropylene glycol methyl ether, AtlanticRichfield).

0.45 gram of the test stabilizer is predissolved in 10 g of the cosolvent blend which is then incorporated into the following composition:

| | |
|---|---|
| FLEXTHANE ® 630 (Air Products) | 100.0 |
| Foamaster VF | 0.1 |
| Water | 10.0 |
| TEXANOL/ARCOSOLVE/hindered amine | 10.5 |
| UV absorber (TINUVIN ® 1130, Ciba) | 1.2 |
| BYK 346 | 0.5 |
| MICHEMLUBE ® 162 | 2.0 |

Each coating is brush applied onto 6"×6" sections of cedar and pine boards. The weight of the coating applied is regulated by weighing the coating and brush before and after application and ensuring that the same weight of coating is applied to each section.

The coated board sections are allowed to dry at ambient temperature for two weeks, then evaluated for visual appearance, gloss and Hunter L*, a* and b* color. The sections are exposed on racks at a 45° angle in South Florida for six months before being returned and evaluated for visual appearance, gloss, color change and any other signs of degradation or delamination.

The instant hindered amine compounds substituted on the N-atom with an -O-E-OH moiety provide better stabilization efficacy to the sections in respect to visual appearance, gloss retention, resistance to color change and to delamination than do the corresponding -NOR compounds lacking such a hydroxyl moiety.

EXAMPLE 112

Stabilization of Pigmented Automotive OEM Basecoat

A basecoat pigmented with a mixture of Pigment Red 177 and mica is stabilized with 1% by weight of a hindered amine stabilizer based on the total basecoat solids (pigment plus resin). The basecoat is spray applied at a dry film thickness of 1 mil (25 microns) to primed 4"×12" steel panels, then topcoated with a high solids commercially available automotive clearcoat. The coated panels are cured in an over at 250° F. (121° C.) for 30 minutes. The panels are then exposed in a Xenon-Arc Weather-Ometer under the following conditions:

Cam 180 cycle: 40 minutes light only; 20 minutes light and front spray; 60 minutes light only; 60 minutes dark and rear spray condensate.

Lamp filters are: quartz inneriborosilicate S outer.

Irradiance: 0.55 wafts per square meter.

20° Gloss, Distinctness of Image, Hunter Color Space Values (L*, a*, b* and $\Delta E$) are measured before exposure and after 3000 hours of exposure.

The instant hindered amine compounds substituted on the N-atom with an -O-E-OH moiety provide better stabilization efficacy to the panels in respect to distinctness of image, gloss retention and resistance to color change than do the corresponding -NOR compounds lacking such a hydroxyl moiety.

EXAMPLE 113

ABS Molding Applications

Thermoplastic materials composed of mixtures of copolymers derived from the copolymerization of styrene monomer with acrylonitrile and the copolymerization of stryrene monomer with butadiene, generally referred to as ABS, are dry blended with the instant compounds and melt compounded into pellets. Typical formulations contain the instant compounds at levels from 0.05% to 2.0%, a metal stearate such as calcium stearate at 0.05% to 0.5%, pigments from 0% to 5%, UV absorbers at levels of 0.05% to 2.0%, phosphites at 0.0%–0.1%, phenolic antioxidants at 0.0%–1.25%, N,N-dialkylhydroxylamine at 0.0%–0.1%, and optionally other hindered amine stabilizers at levels of 0.0% to 2.0%.

The pelletized fully formulated resin is then processed into a useful article such as extrusion into sheet, film, profile and pipe; molded into bottles; injection molded into a molded article; thermoformed into molded articles; or rotational molded into hollow articles.

The materials containing the instant compounds exhibit stability against deleterious effects of UV light and thermal exposure.

EXAMPLE 114

$pK_a$ Values

In order to determine the $pk_a$ values of water insoluble materials, organic references with known $pk_a$ values in water are titrated non-aqueously. A plot of the half neutralization potential (HNP) versus the known aqueous $pk_a$ value of the reference material is establed. The HNP of the test material is determined and extrapolated to find the corresponding $pK_a$ value of the test material. Such organic reference materials include 2,2,6,6-tetramethylpiperidine; 4-hydroxy-2,2,6,6-tetramethylpiperidine; 1-hydroxyethyl-4-hydroxy-2,2,6,6-tetramethylpiperidine; triacetoneamine and N-methylaniline.

The reference materials, which are structurally at least peripherally related to the instant test materials and are soluble in both water and 1:1 acetonitrile:chloroform, are used to make a calibration plot in the non-aqueous titration (1:1 acetonitrle:chloroform solvent and 0.1N perchloric acid/dioxane titrant) system. Approximately 0.5 milliequivalents of test material is weighed into a titration beaker. Thirty mL of acetonitrile is added to dissolve the sample. Prior to titration, 30 mL of chloroform is added. Titration is carried out and the HNP is determined. The electrolyte for the reference electrode is 2-(aminomethylpyridine. The electrode is allowed to stand in the solvent system for two hours after filling with the electrolyte to achieve equilibration. All samples are run in duplicate. The $pk_a$ values are seen in the table below.

| Sample* | HPN (mv) | Calculated $pK_a$ |
|---|---|---|
| I | 523 | 3.9 |
| II | 436 | 4.9 |
| III | 513 | 3.8 |
| IV | — | 4.6 |
| V | — | 3.8 |
| VI | — | 4.8 |

*I is the compound of Example 73.
II is 1-cyclohexyloxy-4-ocatadecanoyloxy-2,2,6,6-tetramethylpiperidine.
III is the compound of Example 2.
IV is bis(1-octyloxy-2,2,6,6-tetramethylpiperidin-4-yl) sebacate.
V is the compound of Example 50.
VI is the reaction product of 2,4-bis[N-(1-cyclohexyloxy-2,2,6,6-tetramethylpiperidin-4-yl)butyl-amino]-6-chloro-s-triazine with N,N'-bis(3-aminopropyl)ethylenediamine.

As can be seen from each of the above pairs of related compounds where the individual compounds differ from the other only by whether the 1-position of the piperidine ring is substituted by an -O-R group or by an -O-E-OH, the instant -O-E-OH compounds consisting have a significantly lower $pk_a$ value meaning that said instant compounds are distinguished by consistently lower basicity than the prior art N—OR compounds.

Inspection of the results given in Example 77 shows that this lower basicity and lower $pK_a$ values can be translated into superior performance for the instant compounds compared to the closely related prior art N—OR compounds in preventing paint loss on paintable thermoplastic polyolefins (TPO).

EXAMPLE 115

Flame Retardancy

Fiber grade polypropylene, is dry blended with the test additives and then melt compounded at 234° C. (450° F.) into pellets. All formulations additionally contain melt processing stabilizer system. The pelletized fully formulated resin is then spun at 246° C. (475"F) into fiber using a Hills laboratory model fiber extruder. The spun tow of 41 filaments is stretch at a ratio of 1:3.2 to give a final denier of 615/41.

The fibers are then knitted into socks and on a Lawson-Hemphill Analysis Knitter. Ten replicates of each sample are tested under NFPA701-1996 Vertical bum procedure. The time in seconds for the knitted sock to extinguish after the insult flame is removed is reported as "After Flame". Efficacy as a flame retardant is demonstrated when low After Flame times are observed relative to a blank sample containing no flame retardant. The burning time of the drips from the material and the weight loss are also recorded. The data demonstrates that the instant NOR HALS are effective as flame retardants.

| Additive | After flame (s) | Drip Bum (s) | Weight loss % |
|---|---|---|---|
| BLANK, no FR | 32 | >50 | 63 |
| Compound of Example 73, 1.0% | 0.5 | 12.5 | 36 |

EXAMPLE 116

Flame Retardancy of Polypropylene Thick Sections

Molding grade polypropylene is dry blended with test additives and then melt compounded into pellets. In addition to the instant compound, halogenated flame retardants are included in the formulation. Typical formulations contain the instant compound and a flame iretardants such as: tris(3-bromo-2,2 bis(bromomethyl)propyl)phosphate (FMC PB370); bis(2,3-dibromopropyl ether) of bisphenol A (PE68); decabromodiphenyloxide (DBDPO); ethylene bis-tetrabromophthalimide (SATEX BT-93); ethylene bis-dibromonorbomanedicarboximide (SATEX BN-451). Other formulations may contain $Sb_2O_3$ in addition to the brominated flame retardants. Other formulations may contain phosphorous based flame retardants such as ethylene diamine diphosphate (EDAP). The pelletized fully formulated resin is then compression molded into test specimens using a Wabash Compression Molder.

Test plaques are tested under UL-94 Vertical bum conditions. A minimum of three replicates are tested. The average time in seconds for the test sample to extinguish after a first and second insult flame is removed is reported. Efficacy as a flame retardant is demonstrated when low Flame times are observed. The instant compounds enhance the flame retardancy of a halogenated or phosphate flame retardant tested alone.

EXAMPLE 117

Flame Retardancy in TPO Thick Sections

Molded test specimens were prepared by injection molding thermoplastic olefin (TPO) pellets containing the instant compounds. The TPO formulations may also contain pigments, a phenolic antioxidant, phosphite or hydroxylamine, a metal stearate, ultraviolet light absorbers (UVA) or a hindered amine stabilizers (HALS) or a mixture of UV absorbers and hindered amine stabilizers.

In addition to the instant compound, halogenated flame retardants are included in the formulation. Typical formulations contain the instant compound and a flame retardants such as: tris(3-bromo-2,2 bis(bromomethyl)propyl) phosphate (FMC PB370); bis(2,3-dibromopropyl ether) of bisphenol A (PE68); decabromodiphenyloxide (DBDPO); ethylene bis-tetrabromophthalimide (SATEX BT-93); ethylene bis-dibromonorbomanedi-carboximide (SATEX BN-451). Other formulations may contain $Sb_2O_3$ in addition to the brominated flame retardants. Other formulations may contain phosphorous based flame retardants such as ethylene diamine diphosphate (EDAP).

Test plaques are tested under UL-94 Vertical bum conditions. A minimum of three replicates are tested. The average time in seconds for the test sample to extinguish after a first and second insult flame is removed is reported. The instant compounds enhance the flame retardancy of a halogenated or phosphate flame retardant tested alone.

EXAMPLE 118

Light Stability in Flame Retardant ABS Molding Applications

Molding grade ABS is dry blended with test additives and then melt compounded into pellets. In addition to the instant compounds, selected flame retardants are also included. The flame retardants are tris[3bromo-2,2-bis(bromomethyl) propyl]phosphate, decabromodiphenyl oxide, ethylene bis (tetrabromophthalimide) and ethylene bis (dibromonorbomanedicarboximide). The pelletized fully formulated resin is then injection molded into test specimens using a BOY 50M laboratory model injection molder. Other formulations may contain antimony trioxide ($Sb_2O_3$) in addition to the brominated flame retardants. Other formulation may contain phosphorus based flame retardants such as ethylenediamine diphophate (EDAP).

Test plaques are mounted in metal frame and exposed in an Atlas Ci65 Xenon Arc Weather-O-meter with intermittent light/dark cycles and water spray following the ASTM G26 test procedure. Specimens are tested at periodic intervales for changes in tensile properties and for changes in color. The longer it takes for the loss in properties to occur and the less the color change as measured by ΔE, the more effective is the stabilizer system.

The test samples containing the instant compounds exhibit good retention of tensile properties and minimal color change during the accelerated weathering.

EXAMPLE 119

Light Stability in Flame Retardant HIPS Molding Applications

Molding grade high impact polystyrene is dry blended with test additives and then melt compounded into pellets. In addition to the instant compounds, selected flame retardants are also included. The flame retardants are tris[3bromo-2,2-bis(bromomethyl)propyl]phosphate, decabromodiphenyl oxide, ethylene bis(tetrabromophthalimide) and ethylene bis(dibromonorbomanedicarboximide). The pelletized fully formulated resin is then injection molded into test specimens using a BOY 50M laboratory model injection molder. Other formulations may contain antimony trioxide ($Sb_2O_3$) in addition to the brominated flame retardants. Other formulation may contain phosphorus based flame retardants such as ethylenediamine diphophate (EDAP).

Test plaques are mounted in metal frame and exposed in an Atlas Ci65 Xenon Arc Weather-O-meter with intermittent light/dark cycles and water spray following the ASTM G26 test procedure. Specimens are tested at periodic intervales for changes in tensile properties and for changes in color. The longer it takes for the loss in properties to occur and the less the color change as measured by ΔE, the more effective is the stabilizer system.

The test samples containing the instant compounds exhibit good retention of tensile properties and minimal color change during the accelerated weathering.

EXAMPLE 120

Stabilization of High Solids Acid-catalyzed Thermoset Acrylic Resin Enamel

A high solids (50% by weight) thermoset acrylic resin enamel, catalyzed by 0.8% by weight of dodecylbenzenesulfonic acid, based on the film-forming resin is stabilized by the addition of various instant compounds. The high solids thermoset acrylic resin enamel formulation (Acryloid AT 400 from Rohm and Haas) is based on hydroxyethyl methacrylate, methyl methacrylate, styrene, butyl acrylate and butyl methacrylate and a melamine curing agent.

Pieces of steel sheeting 4"×12" (9.16 cm×30.48 cm), coated with a primer based on polyester/epoxy resin, are then coated with a $TiO_2$-pigmented base coat based on a binder of 70% of monomers such as hydroxyethyl acrylate, styrene, acrylonitrile, butyl acrylate and acrylic acid with 30% of a melamine resin and an acid catalyst and finally with a clear finishing enamel. The base coat is sprayed onto the sheet to a thickness of about 0.8 mil (0.0203 mm) and air dried for three minutes. The clear finishing enamel is then sprayed onto the sheet to a thickness of about 2.0 mil. After 15 minutes air-drying, the coated sheets are baked for 30 minutes at 121° C.

The stabilizers under test are added to the thermoset acrylic resin finishing enamel in a concentration of 1% by weight before the enamel is coated onto the base coat.

The coated sheets, after storage for three weeks in an air-conditioned room (23° C./50% relative humidity), are subjected to weathering for 2000 hours according to SAE J1920 in a Xenon arc Weather-Ometer. In this apparatus, samples are subjected to weathering in repeated cycles of 180 minutes. The effectiveness of the stabilization is measured by the retention of 20° gloss after weathering.

The sheets stabilized by the instant compounds exhibit good retention of 20° gloss after weathering under extreme weather conditions.

EXAMPLE 121

The samples prepared in Example 120 are also evaluated on the basis of Knoop Hardness (ASTM D1474-68) on baked and overbaked samples; on the distinction of image (DOI); on Hunter Associates Apparatus; on 20° gloss (ASTM D-523-80); and on cracking based on visual observation.

The samples stabilized by the instant compounds exhibit a pattern of greater retention of 20° gloss and DOI, and a longer absence of severe cracking after exposure.

EXAMPLE 122

The thermoset acrylic enamel of Example 120 is formulated to include 3% by weight of a benzotriazole UV absorber and 1.5% by weight of an instant hindered amine test compound. The enamel is coated over a white base coat or over a silver metallic base coat. Baking is conducted at 121° C. normal bake or at 82° C. automotive low bake repair temperature.

The coated panels are exposed in a Xenon arc exposure apparatus and 20° gloss and distinction of image (DOI) values are determined.

The samples stabilized by the instant compounds exhibit a pattern of greater retention of 20° gloss and DOI.

EXAMPLE 123

Two thermoset acrylic enamles are formulated to include 3% by weight of a benzotriazole UV absorber and 1% by weight of an instant hindered amine test stabilizer.

The thermoset acrylic enamels are based on a binder of 70% of monomers such as hydroxyethyl acrylate, styrene, acrylonitrile, butyl acrylate and acrylic acid with 30% of a melamine resin and an acid catalyst such as p-toluenesulfonic acid, dinonylnaphthalenedisulfonic acid, dodecylbenzenesulfonic acid or phenyl acid phosphate.

Pieces of steel sheeting 4"×12" (9.16 cm×30.48 cm), coated with a primer based on polyester/epoxy resin, are then coated with a base coat and finally with a clear finishing enamel. The base coat is sprayed onto the sheet to a thickness of about 0.8 mil (0.0203 mm) and air dried for three minutes. The clear finishing enamel is then sprayed onto the sheet to a thickness of about 2.0 mil. After 15 minutes air-drying, the coated sheets are baked for 30 minutes at 121° C.

The coated panels are exposed in a Xenon arc exposure apparatus and 20° gloss and distinction of image (DOI) values are determined.

The samples stabilized by the instant compounds exhibit a pattern of greater retention of 20° gloss and DOI.

EXAMPLE 124

A white polyester/melamine based oil-free alkyl coil coating is utilized in this example. The fully formulated paint is applied over a primed steel sheet using a wire wound rod to give 0.6–0.8 mil dry film. The panels are baked for about 90 seconds at 220° C., removed from the oven and immediately quenched in water. The coated panels are exposed in a Xenon Arc Weather-Ometer, and in South Florida at an angle of 45° S to the sun. 20° gloss values are determined.

The samples stabilized by the instant compounds exhibit a pattern of greater retention of 20° gloss.

EXAMPLE 125

The thermoset acrylic enamel of Example 124 including 0.8% dodecylbenzenesulfonic acid is formulated to include varying concentrations of benzotriazole or s-triazine UV absorbers and the instant hindered amine test compounds. The enamel is coated over a silver metallic base coat pursuant to the procedure of Example 124 and baking is conducted for 30 minutes at 121° C. the normal backe temperature.

The coated panels are exposed in a Xenon arc Weather-Ometer and the time to the 50% loss of 20° gloss is determined.

The samples stabilized by the instant compounds and a UV absorber exhibit an excellent retention of 20° gloss and a much longer time till 50% loss in 20° gloss is observed.

EXAMPLE 126

A thermoset acrylic enamel based on a binder of 70% of monomers such as hydroxyethyl acrylate, styrene, acrylonitrile, butyl acrylate and acrylic acid with 30% of a melamine resin and an acid catalyst such as p-toluenesulfonic acid, dinonylnaphthalenedisulfonic acid or dodecylbenzenesulfonic acid is formulated. Commercially available 9.16 cm×30.48 cm Uniprime panels are used as the substrate. The panels are coated with a silver metallic base coat and then with a clear finishing enamel. The base coat is stabilized with 1% of a benzotriazole UV absorber and 1% of an instant hindered amine test compound (based on solid resin) and is sprayed onto the panel to a thickness of about 0.6–0.8 mil and air dried for three minutes. The clear coat including the above-noted stabilizers is then sprayed to a thickness of 1.7–2.0 mils and after 10 minutes of air drying, the coated panels are baked for 30 minutes at 121° C. The coated panels are then exposed in a Xenon arc apparatus and the 20° gloss values are determined.

The samples stabilized by the instant compounds and a UV absorber exhibit excellent retention of 20° gloss.

EXAMPLE 127

A water-borne acrylic melamine enamel is formulated as seen below:

|  | Parts Resin Solids |
| --- | --- |
| Synthacryl VSW 6483 | 30 |
| (acrylic dispersion from Hoechst) |  |
| Synthacyl VSW 6484 | 42 |
| (50% acrylic resin in butyl diglycol, Hoechst) |  |
| Maprenal MF 915 | 25 |
| (70% melamine resin in isobutanol) |  |
| Maprenal MF 927 | 3 |
| (melamine resin) | 100 |

A water-based base coat/clear coat enamel is prepared by spray applying a 0.6–0.8 mil thick film of commercial silver metallic waterbome base coat (from BASF) over an epoxy primed coil coated aluminum panel. This material is baked at 80° C. for five minutes and then clear coated with 1.6–1.8 mil of the waterbome enamel. The system is baked at 80° C. for ten minutes and then at 140° C. for a further 30 minutes. Prior to application of the clear coating, instant test and light stabilizers dissolved in a minumum amount of butyl glycol acetate are added to the paint. The coated panels are exposed in a Xenon arc apparatus for 975 hours. The distinction of image (DOI) retention of the panels is measured.

The samples stabilized by the instant compounds exhibit greater retention of DOI values.

EXAMPLE 128

Stabilization of Tung Oil Phenolic Varnish

Pieces of 1.27 cm×20.32 cm×30.48 cm western red cedar panels having a fine radial cut are used to test a commercially available tung oil phenolic varish (supplied by McCloskey). One half of each panel is coated with two coats of unstabilized varnish. An equal amount of varnish containing 5% by weight (based on resin solids) of test stabilizers is applied to the other half of the panel in two coats. After storage for two weeks at ambient temperature, the wood panels are exposed outdoors at an angle of 45° S for a period of eight months. The 60° gloss of each half of the panel is measured at the top, middle and bottom portion of the panel and averaged according to ASTM D 523. Due to the lack of homogeneity of wood substrates, the gloss retention of the same varnish tends to differ slightly from panel to panel. Thus, the application of an unstabilized control varnish to every panel allows for a more meaningful measurement of the improvement in gloss due to the presence of the instant test compound.

The panels stabilized by the instant compounds show excellent gloss retention after long exposure.

EXAMPLE 129

Stabilization of an Aromatic Urethane Varnish

A sample of commercial aromatic urethane varnish (Flecto-Varathane #90) is tested by the same method described in Example 128. After outdoor exposure at an angle of 45° S for a period of five months, the 60° gloss retention values of unstabilized and stabilized portions of the panels are determined.

The panels stabilized by the instant compounds show excellent gloss retention.

EXAMPLE 130

Stabilization of a White Two-Component Polyester Urethane Gloss Enamel

A white polyester is formulated as shown below:

|  | Parts |
| --- | --- |
| Component I | |
| Desmophen 670-90 (polyester glycol, Mobay) | 132.4 |
| Titanium Dioxide | 198.6 |
| Cellosolve Acetate | 98.9 |
| Sand Mill | |
| Desmophen 670-90 | 94.98 |
| Flow Aid | 0.28 |
| Tertiary Amine | 0.015 |
| Cellosolve Acetate | 332.6 |
| Component II | |
| Desmodur N-100 (polyisocyanate, Mobay) | 93.9 |
| Cellosolve Acetate | 58.7 |

This material is spray applied at a dry film thickness of 1.5–2.0 mil onto Bonderite 40 cold rolled steel panels that have been previously primed with a commerical epoxy polyamide maintenance primer (Sherwin-Williams Tile Clad II). Prior to application, the instant test compounds are added to the paint. After ambient storage for two weeks, three panels of each formulation are exposed outdoors at an angle of 45° S for a period of nine months. Thereafter, 20° gloss retention is determined by ASTM D 523-80 at the top, middle and bottom portions of each panel. Thus, the average values for nine gloss retention measurements for each triplicate set of panels are obtained.

The panels stabilized by the instant compounds show excellent gloss retention.

EXAMPLE 131

Stabilization of Acrylic Alkyd Refinish Enamel

A commercially available acrylic alkyd enamel pigments with non-leafing aluminum pigment and tinted a light blue is stabilized with a benzotriazole UV absorber and an instant hindered amine test compound and is then spray applied onto Bonderite 40 panels primed with an alkyd primer. After the coating is allowed to cure at room temperature for 14 days, the panels are exposed outdoors at an angle of 45° S for a period of eight months. The 20° gloss of the exposed panels is measured.

The panels stabilized by the instant compounds show excellent gloss retention.

EXAMPLE 132

Stabilization of a Medium Oil Alkyd Enamel

A medium oil alkyd enamel pigmented with a non-leafing aluminum pigment and tinted light blue is stabilized with a benzotriazole UV absorber and an instant hindered amine test compound and is then sprayed applied onto cold rolled steel panels primed with an epoxy primer. After the coating is allowed to cure at room temperature for two weeks, the panels are exposed for accelerated weathering in a Xenon Arc Weather-Ometer for 840 hours. The 20° gloss values of the panels are determined before and after exposure.

The panels stabilized by the instant compounds show excellent gloss retention.

EXAMPLE 133

Electrocoat Composition

A typical E-coat composition is prepared by adding the diglyicidyl ether of bisphenol A, polyethylene oxide diol, bisphenol A and xylene to a flask and heating to 135° C. The catalyst dimethylbenzylamine in xylene is added and the temperature maintained at 143° C. for two hours. The weight per epoxy (WPE) is measured and a previously prepared crosslinker composed of 2,4-toluenediisocyanate, trimethylolpropane blocked with an alcohol is then added and temperature reduced to 100° C. The remaining epoxy groups are then capped with two different secondary amines, namely diketimine of diethylenetriamine and methylethanolamine, in phenyl cellosolve. The temperature is maintained for one hour at 110° C. and the crosslinker hexamethylenediisocyanate blocked with an alcohol is added. The temperature is maintained near 100° C. for 30 minutes and the resin mixture is added to deionized water, surfactant and lactic acid to give a resin emulsion.

To this resin emulsion is added the instant hindered amine compound, additional epoxy resin, carbon black, dibutyltin oxide catalyst, titanium dioxide, lead silicate, water and UV absorber. After dispersion using a sand mill to achieve proper fineness, the mixture is incorporated into an electrocoat bath with water for electrocoating onto a metal substrate.

The steel coating electrocoated with the above E-coat resin composition to a thickness of 23–30 $\mu$m and cured for 20 minutes at a temperature of 176–201° C. A pigmented resin layer is coated thereover at a thickness of 20–51 $\mu$m using an acrylic coating composition in an organic solver, pigments and a UV absorber. The coated panels are then baked at 121–129° C. to cure the pigmented layer.

The panels are then exposed outdoors for four months. The panels containing the instant hindered amine compound, particularly when used with a UV absorber, provided excellent resistance to delamination of the E-coat layer from the metal substrate.

EXAMPLE 134

Abrasion-Resistant Coating Compositions

A solution in isopropanol of 50% (by weight) of 1,6-hexanediol, 10% 3-methacryloyloxypropyltrimethoxysilane and 40% colodial silica (in form of a 34% aqueous dispersion) is vacuum stripped to remove volatiles and combined with an instant hindered amine compound, a benzotriazole UV absorber and 2,4,6-trimethylbenzoyidiphenylphosphine photoinitiator. These compositions show no gelation on storage.

The compositions above are applied by roller coating to a 15 mil film of bisphenol A polycarbonate and the coated films are passed under a mercury lamp at 43° C. at a line speed of 610 cm/min. The compositions are cured to a colorless and optically clear coatings over the polycarbonate substrate.

The coatings as measured by the Taber Abrasion Test (ASTM D 1044) are abrasion resistant.

The test specimens are also subjected to accelerated aging tests using an Atas Ci35A Xenon Arc Weather-Ometer. The results show that the coatings containing the instant hindered amine compound exhibit excellent resistance to yellowness and haze formation.

EXAMPLE 135

Coating over Polycarbonate

A two-component polyester urethane coating is stabilized by the addition of an instant hindered amine compound. The high-solids polyester polyol (Desmophen 670-80, Bayer) is crosslinked with an isocyanate based resin (Desmodue N-3390, Bayer). The coating is catalyzed with 0.015% by weight of dibutyltin dilaurate catalyst.

Plaques of polycarbonate-based plastic substrate (Xenoy) 4"×6" are coated with the formulated clear coat at a thickness of approximately 1.5 mils. The coating is spray applied to the substrate and then baked at 82° C. for 20 minutes.

After storage for one week at room temperature, each plaque is cut into 2"×3" strips with five replicates being made for each formulation. Each strip is placed into a 8-oz jar along with 2 mL of distilled water and sealed. All samples are placed in an over at 54° C. A crosshatch adhesion test is performed once a week on at least two of the replicate samples until the sample failed (5% adhesion loss) or until 40 days elapses.

The samples containing the instant hindered amine compounds exhibit excellent resistance to delamination.

What is claimed is:

1. A composition which comprises (a) an organic polymer subject to the adverse effects of heat, oxygen and light, and (b) an effective stabilizing amount of a compound of formula (29) which is the condensation product of a dialkyl ester or diisocyanate with a hydroxy substituted N-alkoxy derivative of 4-hydroxy-2,2,6,6-tetramethylpiperidine as described in formula (29)

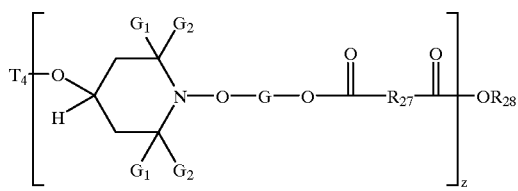

wherein
$G_1$ and $G_2$ are independently alkyl of 1 to 4 carbon atoms, or $G_1$ and $G_2$ together are pentamethylene;
z is an integer such that the compound has a molecular weight of 1000 to 4000 amu;
G is a straight or branched chain alkylene of 1 to 18 carbon atoms, cycloalkylene of 5 to 8 carbon atoms, cycloalkenylene of 5 to 8 carbon atoms, alkenylene of 3 to 18 carbon atoms, a straight or branched chain alkylene of 1 to 4 carbon atoms substituted by phenyl or by phenyl substituted by one or two alkyl of 1 to 4 carbon atoms, with the proviso that in formula (29) successive hindered amine moieties can be oriented in either a head to head or head to tail fashion;

$T_4$ is hydrogen or

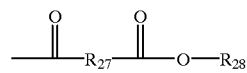

$R_{27}$ is a straight or branched chain alkylene of 1 to 18 carbon atoms, cycloalkylene or cycloalkenylene of 5 to 8 carbon atoms, phenylene or —NH-alkylene-NH— of 2 to 18 carbon atoms including 5-amino-1-aminomethyl-1,3,3-trimethylcyclohexane and —NH-xylylene-NH—; and $R_{28}$ is alkyl of 1 to 4 carbon atoms,

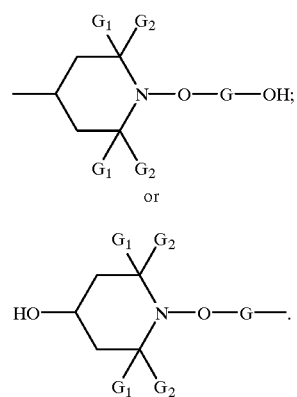

2. A composition according to claim 1 wherein component (a) is a theermoplastic polyolefin, polyester, polyester urethane, polyesther urethane or a water-borne coating.

3. A composition according to claim 1 wherein component (a) is selected from the group consisting of polypropylene, thermoplastic polyolefin, low density polyethylene, medium density polyethylene, high density polyethylene, linear low density polyethylene, poly(butene-1), ethylene/vinyl acetate copolymer, ethylene/propylene copolymer, copolymers of ethylene or propylene with other alpha-olefins, copolymers of acrylonitrile-butadiene-styrene (ABS), copolymers of acrylonitrile and styrene that are impact modified with ethylene-propylene rubber or ethylene/propylene/alpha-olefin rubber or butyl acrylate rubber, blends of ABS and polycarbonate, blends of ABS and poly(vinyl chloride) (PVC), poly(vinyl chloride), copolymers of styrene and butadiene (HIPS), copolymers of styrene and butadiene that also contain ethylene-propylene rubber or ethylene/propylene/alpha-olefin rubber or butyl acrylate rubber, thermoplastic elastomers and thermoplastic vulcanizates.

4. A composition according to claim 1 wherein component (a) is a polyester or polyether urethane or water-borne coating.

5. A composition according to claim 1 which additionally contains an effective stabilizing amount of at least one coadditive stabilizer selected from the group consisting of the phenolic antioxidants, metal stearates, metal oxides, organophosphorus compounds, furanone antioxidants, hydroxylamines, UV absorbers, non-NOR hindered amines, NOR hindered amines and mixtures thereof.

6. A composition according to claim 1 which additionally contains a filler.

7. A composition according to claim 6 wherein the filler is calcium carbonate, clay, talc, mica or glass.

8. A composition according to claim 1 wherein component (a) is an agricultural film which is exposed to pesticides.

9. A composition according to claim 1 wherein component (a) is an agricultural film exposed to pesticides, and component (b) additionally contains a metal stearate and zinc oxide.

10. A composition according to claim 1 wherein component (a) is a polyolefin film, fiber or thick section, ABS, high impact polystyrene (HIPS), thermoplastic polyolefin, thermoplastic elastomer or thermoplastic vulcanizate which additionally contains a halogenated flame retardant.

11. A composition according to claim 10 wherein the flame retardant is tris[3-bromo-2,2-bis(bromomethyl) propyl]phosphate, decabromodiphenyl oxide, ethylene bis (tetrabromophthalimide) or ethylene bis (dibromonorbomanedicarboximide).

12. A composition according to claim 10 wherein component (a) is polypropylene fiber.

13. A composition according to claim 1 wherein component (a) is polypropylene, polyethylene, thermoplastic polyolefin (TPO), ABS or high impact polystyrene (HIPS), and component (b) is an effective synergistic mixture of
  (i) a compound of formula (29) according to claim 1; and
  (ii) a flame retardant selected from the group consisting of the halogenated, phosphorus, boron, silicon and antimony compounds, metal hydroxides, metal hydrates, metal oxides and mixtures thereof.

14. A composition according to claim 13 wherein component (a) is polypropylene, polyethylene or thermoplastic polyolefin (TPO).

15. A composition according to claim 1 wherein component (a) is a paintable thermoplastic olefin (TPO).

16. A composition according to claim 5 wherein the coadditive stabilizer is a hindered phenolic antioxidant selected from the group consisting of neopentanetetrayl tetrakis(3,5-di-tert-butyl-4-hydroxyhydrocinnamate, octadecyl 3,5-di-tert-butyl-4-hydroxyhydrocinnamate, 1,3,5-trimethyl-2,4,6-tris(3,5,-di-tert-butyl-4-hydroxybenzyl) benzene, 1,2-bis(3,5-di-tert-butyl)-4-hydroxyhydrocinnamoyl)hydrazine, calcium [bis (monoethyl 3,5-ditert-butyl-4-hydroxybenzyl)-phosphonate], 1,3,5-tris(3,5-di-tert-butyl-4-hydroxybenzyl) isocyanurate and 1,3,5-tris(3-hydroxy-4-tert-butyl-2,6-dimethylbenzyl)isocyanurate; or is an organophosphorus stabilizer selected from the group consisting of tris(2,4-di-tert-butylphenyl)phosphite, bis(2,4-di-tert-butyl-6-methylphenyl)ethyl phosphite, 2,2',2"-nitrilo[triethyl-tris-(3,3',5,5'-tetra-tert-butyl-1,1'-biphenyl-2,2'-diyl)phosphite], tetrakis(2,4-di-butylphenyl) 4,4'-biphenylenediphosphonite, tris(nonylphenyl)phosphite, bis(2,4-di-tert-butylphenyl) pentaerythrityl diphosphite, 2,2'-ethylidenebis(2,4-di-tert-butylphenyl)fluorophosphite and 2-butyl-2-ethylpropan-1,3-diyl 2,4,6-tri-tert-butylphenyl phosphite; or is 5,7-di-tert-butyl-3-(3,4-dimethylphenyl)-2H-benzofuran-2-one; or is N,N-dialkylhydroxylamine made by the direct oxidation of N,N-di(hydrogenated tallow)amine; or is a hindered amine selected from the group consisting of bis(2,2,6,6-tetramethylpiperidin-4-yl)sebacate, the polycondensation product of 1-(2-hydroxyethyl)-2,2,6,6-tetramethyl-4-hydroxypiperidine and succinic acid, N,N',N",N'"-tetrakis[4,6-bis(butyl-1,2,2,6,6-pentamethylpiperidin-4-yl)amino-s-triazin-2-yl]-1,10diamino-4,7-diazadecane, the polycondensation product of 4,4'-hexamethylenebis(amino-2,2,6,6-tetramethylpiperidine) and 2,4-dichloro-6-tert-octylamino-s-triazine, the polycondensation product of 4,4'-hexamethylene-bis(amino-2,2,6,6-tetramethylpiperidine) and 2,4-dichloro-6morpholino-s-triazine, the polycondensation product of 4,4'-hexamethylenebis(amino-1,2,2,6,6-pentamethylpiperidine) and 2,4-dichloro-6-morpholino-s-triazine, 2,2,6,6-tetramethylpiperidin-4-yl octadecanoate, 3-dodecyl-1-(1-acetyl-2,2,6,6-tetramethylpiperidin-4-yl)-pyrrolidin-2,5-dione, 1,3,5-tris{N-cyclohexyl-N-[2-(2,2,6,6-tetramethylpiperazin-3-on-4-yl)ethyl]amino}s-triazine, poly[methyl 3-(2,2,6,6-tetramethylpiperidin-4-yloxy)propyl]siloxane, the polycondensation product of 2,4-dichloro-6-(2,2,6,6-tetramethylpiperidin-4-yl)butylamino)-s-triazine, 2,2'ethylene-bis{[2,4-(2,2,6,6-tetramethylpiperidin-4-yl)butylamino-s-triazin-6-yl] aminotrimethyleneamino}, oligomer of N-{[2-(N-2,2,6,6-tetramethylpiperidin-4-yl)butylamino]-s-triazin-4-yl-N,N'-bis(2,2,6,6-tetramethylpiperidin-4-yl)-1,6-hexanediamine terminated with 2,4-bis(dibutylamino)-s-triazin-6-yl, N,N',N"-tris{2,4-bis[N-(1,2,2,6,6-pentamethylpiperidin-4-yl) butylamino]-s-triazin-6-yl}3,3'-ethylenediiminodipropylamine, N,N',N'"-tris{2,4-bis[N-(1,2,2,6,6-pentamethylpiperidin-4-yl)butyl-amino]-s-triazin-6-yl}-3,3'-ethylenediiminodipropylamine and N,N',N",N'"-tetrakis{2,4-bis[N-(1,2,2,6,6-pentamethylpiperidin-4-yl) butylamino]-s-triazin-6-yl}-3,3'-ethylenediiminodipropylamine; or is another N-hydrocarbyloxy substituted hindered amines selected from the group consisting of bis(1-octyloxy-2,2,6,6-tetramethylpiperidin-4-yl)sebacate, bis(1-octyloxy-2,2,6,6-tetramethylpiperidin-4-yl)adipate, bis(1-cyclohexyloxy-2,2,6,6-tetramethylpiperidin-4-yl) adipate, bis(1-cyclohexyloxy-2,2,6,6-tetramethylpiperidin-4-yl)sebacate, 1-cyclohexyloxy-2,2,6,6-tetramethylpiperidin-4-yl octadecanoate, N,N',N"-tris{2,4-bis[N-(1-cyclohexyloxy-2,2,6,6-tetramethylpiperidin-4-yl)butylamino]-s-triazin-6-yl}-3,3'-ethylenediiminodipropylamine, N,N',N'"-tris{2,4-bis[N-(1-cyclohexyloxy-2,2,6,6-tetramethylpiperidin-4-yl) butylamino]-s-triazin-6-yl}-3,3'-ethylenediiminodipropylamine and N,N',N",N'"-tetrakis{2,4-bis[N-(1-cyclohexyloxy-2,2,6,6-tetramethylpiperidin-4-yl)butylamino]-s-triazin-6-yl}3,3'-ethylenediiminodipropylamine; or is a UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5di-tert-amylphenyl)-2H-benzotriazole, 2-(2-hydroxy-3-α-cumyl-5tert-octylphenyl)-2H-benzotriazole, 2,4-di-tert-butylphenyl 3,5-di-tert-butyl4-hydroxybenzoate, 2-hydroxy-4-n-octyloxybenzophenone, 2,4-bis(2,4-dimethyphenyl)-6-(2-hydroxy-4-octyloxyphenyl)-s-triazine, oligomer of N-{2-[(1-propoxy-2,2,6,6-tetramethylpiperidin-4-yl)butylamino]-s-triazin-4-yl}-N,N'-bis(1-propoxy-2,2,6,6-tetramethylpiperidin-4-yl)-1,6-hexanediamine terminated with 2,4-bis(dibutylamino)-s-triazin-6-yl, the condensation product of 2-morpholino-4,6-dichloro-s-triazine with N,N'-bis(1,2,2,6,6-pentamethylpiperidin-yl-1,6-hexanediamine; or mixtures thereof.

17. A composition according to claim 16 wherein the coadditive stabilizer is neopentanetetrayl tetrakis(3,5-di-tert-butyl-4-hydroxyhydrocinnamate, tris(2,4-di-tert-butyl-phenyl)phosphite, N,N-dialkylhydroxylamine made by the direct oxidation of N,N-di(hydrogenated tallow)amine, N,N',N",N'"-tetrakis[4,6-bis(butyl-1,2,2,6,6-pentamethylpiperidin-4-yl)amino-s-triazin-2-yl]-1,10-diamino4,7-diazadecane, the polycondensation product of 4,4'-hexamethylenebis(amino-2,2,6,6-tetramethylpiperidine) and 2,4-dichloro-6-tert-octylaminos-triazin, the polycondensation product of 4,4'-hexamethylenebis(amino-2,2,6,6-tetramethylpiperidine) and 2,4-dichloro-6-morpholino-s-triazine, the polycondensation product of 4,4'-hexamethylenebis(amino-1,2,2,6,6-pentamethylpiperidine) and 2,4-dichloro4-morpholino-s-triazine, oligomer of N-{[2-(N-2,2,6,6-tetramethylpiperidin-4-yl)butylamino]-s-triazin-4-yl}-N,N'-bis(2,2,6,6-tetramethylpiperidin-4-yl)-1,6-hexanediamine terminated with 2,4-bis(dibutylamino)-s-triazin-6-yl, N,N',N"-tris{2,4-bis[N-(1,2,2,6,6-pentamethylpiperidin-4-yl)butylamino]-s-triazin-6-yl}-3,3'-ethylenediiminodipropylamine, N,N',N'''-tris(2,4-bis[N-(1,2,2,6,6-pentamethylpiperidin-4-yl)butylamino]-s-triazin-4-yl}-3,3'-ethylenediiminodipropylamine and N,N',N'',N''''-tetrakis}2,4-bis[N-(1,2,2,6,6-pentamethylpiperidin-4-yl)butylamino]-s-triazin-4-yl}-3,3'-ethylenediiminodipropylamine, oligomer of N-{2-[(1-propoxy-2,2,6,6-tetramethylpiperidin-4-yl)butylamino]-s-triazin-4-yl}-N,N'-bis(1-propoxy-2,2,6,5tetramethylpiperidin-4-yl)-1,6-hexanediamine terminated with 2,4-bis(dibutylamino)-s-triazin-6-yl, or the condensation product of 2-morpholino-4,6-dichloro-s-triazine with N,N'-bis(1,2,2,6,6-pentamethylpiperidin-4-yl)-1,6-hexanediamine.

18. A composition according to claim 16 which additionally contains 2-(2-hydroxy-3,5-di-tert-amylphenyl)-2H-benzotriazole, 2,4-di-tert-butylphenyl 3,5-d-tert-butyl-4-hydroxybenzoate, 2-hydroxy-4-n-octyloxybenzophenone, 2-(2-hydroxy-3-tert-butyl-5-methylphenyl)-2H-benzotriazole or mixtures thereof.

19. A composition according to claim 5 wherein the coadditive stabilizer is a UV absorber selected from the group consisting of
(a) 5-trifluoromethyl-2-(2-hydroxy-3-α-cumyl-5-tert-octylpenyl)-2H-benzotraizole;
(b) 5-trifluoromethyl-2-(2-hydroxy-5-tert-octylphenyl)-2H-benzotriazole;
(c) 5-trifluoromethyl-2-(2-hydroxy-3,5-di-tert-octylphenyl)-2H-benzotriazole;
(d) 2,2'-methylene-bis[6-(5-trifluoromethyl-2H-benzotriazol-2-yl)-4-tert-octylphenol];
(e) methylene-2-[4-tert-octyl-6-(2H-benzotriazol-2-yl)phenol]2'-[4-tert-octyl-6-(5-trifluoromethyl-2H-benzotriazol-2-yl)phenol];
(f) 3-(5-trifluoromethyl-2H-benzotriazol-2-yl)-5-tert-butyl-4-hydroxyhydrocinnamic acid;
(g) methyl 3-(5-trifluoromethyl-2H-benzotriazol-2-yl)-5-tert-butyl-4-hydroxyhydrocinnamate;
(h) isooctyl 3-(5-trifluoromethyl-2H-benzotriazol-2-yl)-5-tert-butyl-4-hydroxyhydrocinnamate;
(i) 5-trifluoromethyl-2-[2-hydroxy-5-(3-hydroxypropyl)phenyl]-2H-benzotriazole;
(j) 5-trifluoromethyl-2-[2-hydroxy-5-(3-acryloyloxypropyl)phenyl]-2H-benzotriazole;
(k) 5-trifluoromethyl-2-[2-hydroxy-5-(3-methacryloyloxypropyl)phenyl]-2H-benzotriazole;
(l) 5-trifluoromethyl-2-[2-hydroxy-5-(3-acrylylaminopropyl)phenyl]-2H-benzotriazole;
(m) 5-trifluoromethyl-2-[2-hydroxy-5-(3-methacrylylaminopropyl)phenyl]-2H-benzotriazole;
(n) 5-trifluoromethyl-2-(2-hydroxy-3-α-cumyl-5-tert-butylphenyl)-2H-benzotriazole;
(o) 5-trifluoromethyl-2-(2-hydroxy-3-α-cumyl-5-nonylphenyl)-2H-benzotriazole;
(p) 5-trifluoromethyl-2-[2-hydroxy-3-α-cumyl-5-(2-hydroxyethyl)phenyl]-2H-benzotriazole;
(q) 5-trifluoromethyl-2-[2-hydroxy-3-α-cumyl-5-(3-hydroxypropyl)phenyl]-2H-benzotriazole;
(r) 5-trifluoromethyl-2-(2-hydroxy-3,5-di-tert-amylphenyl)-2H-benzotriazole;
(s) 5-trifluoromethyl-2-(2-hydroxy-3,5-di-tert-butylphenyl)-2H-benzotriazole;
(t) 5-trifluoromethyl-2-(2-hydroxy-3-dodecyl-5-methylphenyl)-2H-benzotriazole;
(u) 5trifluoromethyl-2-[2-hydroxy-3-tert-butyl-5-(3-hydroxypropyl)phenyl]-2H-benzotriazole;
(v) 5-trifluoromethyl-2-[2-hydroxy-3-tert-butyl-5-(2-hydroxyethyl)phenyl]-2H-benzotriazole;
(w) 5-trifluoromethyl-2-[2-hydroxy-5-(2-hydroxyethyl)phenyl]-2H-benzotriazole;
(x) 5-trifluoromethyl-2-(2-hydroxy-3,5-di-α-cumylphenyl)-2H-benzotriazole;
(y) 5-fluoro-2-(2-hydroxy-3,5-di-α-cumylphenyl)-2H-benzotriazole;
(z) 5-butylsulfonyl-2-(2-hydroxy-3,5-di-α-cumylphenyl)-2H-benzotriazole;
(aa) 5-butylsulfonyl-2-(2-hydroxy-3,5-di-tert-butylphenyl)-2H-benzotriazole;
(bb) 5-butylsulfonyl-2-(2-hydroxy-3,5-di-tert-octylphenyl)-2H-benzotriazole; and
(cc) 5-phenylsulfonyl-2-(2-hydroxy-3,5-di-tert-butylphenyl)-2H-benzotriazole.

20. A composition according to claim 1 which is a stabilized stoving lacquer wherein component (a) is an acid catalyzed resin based on hot crosslinkable, acrylic, acrylic melamine, polyester, polyurethane, polyamide or alkyd resin.

21. A composition according to claim 20 which additionally contains a UV absorber.

22. A composition according to claim 20 which is an enamel of high solids content for industrial finishes.

23. A composition according to claim 20 which is a finishing enamel for automobiles.

24. A composition according to claim 1 which is a stabilized ambient curable composition wherein component (a) is a resin selected from the group consisting of unmodified or modified alkyd resin, acrylic resin, acrylic alkyd resin, polyester resin or crosslinkable epoxide resin.

25. A composition according to claim 24 wherein the resin is selected from the group consisting of unmodified alkyl, acrylic, acrylic alkyd or polyester resins; said resins modified with silicon, isocyanates, isocyanurates, ketimines or oxazolidines; crosslinked epoxy resins; and epoxy-crosslinked acrylic and polyester resins.

26. A composition according to claim 24 which is an enamel of high solids content for industrial finishes.

27. A composition according to claim 24 which is a finishing enamel for automobiles.

28. A composition according to claim 1 which is a curable electrocoat composition wherein component (a) is an amino-group containing resin having functional groups that are reactive with an isocyanate and an aromatic polyisocyanate crosslinking agent.

29. A composition according to claim 1 which is a non-gelling liquid coating composition wherein component (a) comprises (A) at least one acrylic monomer, (B) silica and (C) at least one initiator for ultraviolet radication-induced curing of said composition.

30. A composition according to claim 29 which contains a silyl acrylate, a polyfunctional acrylate, silica and a photoinitiator.

31. A composition according to claim 1 where in the compound of formula (29), $G_1$ and $G_2$ are each methyl.

32. A composition according to claim 1 where in the compound of formula (29),
   $R_{27}$ is ethylene, trimethylene, tetramethylene, octamethylene, 1,6-diaminohexane or 5-amino-1-aminomethyl-1,3,3-trimethylcyclohexane;
   z is an integer such that the molecular weight of the compound is 1500–3000 amu;
   $R_{28}$ is methyl or ethyl; and
   G is ethylene, 1,2-cyclohexanediyl, 1,3-cyclohexanediyl, 1,4-cyclohexanediyl, —CH($C_6H_5$)$CH_2$— or —$CH_2$C($CH_3$)$_2$—.

33. A composition according to claim 1 where in the compound of formula (29),
   $R_{27}$ is ethylene, trimethylene, tetramethylene or octamethylene;
   z is an integer such that the molecular weight of the compound is 1500 to 2000 amu; and
   $R_{28}$ is methyl.

34. A composition according to claim 1 where in the compound of formula (29), -G-O- is —$CH_2$C($CH_3$)$_2$—O—.

35. A composition according to claim 1 wherein the compound of formula (29) is (m) condension product of 4-hydroxy-1-(2-hydroxy-2-methylpropoxy)-2,2,6,6-tetramethylpiperidine with hexamethylene diisocyanate and terminated with methoxy;

(n) condension product of 4-hydroxy-1-(2-hydroxyethoxy)-2,2,6,6-tetramethylpiperidine with hexamethylene diisocyanate and terminated with methoxy; or (o) condension product of 4-hydroxy-1-(2-hydroxy-2-phenethoxy)-2,2,6,6-tetramethylpiperidine with hexamethylene diisocyanate and terminated with methoxy.

* * * * *